(12) United States Patent
Mugan et al.

(10) Patent No.: US 11,298,113 B2
(45) Date of Patent: Apr. 12, 2022

(54) DEVICE FOR NEEDLE BIOPSY WITH INTEGRATED NEEDLE PROTECTION

(71) Applicant: COVIDIEN LP, Mansfield, MA (US)

(72) Inventors: John Mugan, Moycullen (IE); Brian Murphy, Knocknacarra (IE); John McWeeney, Brighton, MA (US)

(73) Assignee: Covidien LP, Mansfield, MA (US)

( * ) Notice: Subject to any disclaimer, the term of this patent is extended or adjusted under 35 U.S.C. 154(b) by 819 days.

(21) Appl. No.: 15/886,293

(22) Filed: Feb. 1, 2018

(65) Prior Publication Data

US 2018/0235585 A1    Aug. 23, 2018

Related U.S. Application Data

(63) Continuation of application No. 14/630,742, filed on Feb. 25, 2015, now Pat. No. 9,913,630, which is a
(Continued)

(51) Int. Cl.
*A61B 10/04* (2006.01)
*A61B 10/02* (2006.01)
(Continued)

(52) U.S. Cl.
CPC .......... *A61B 10/04* (2013.01); *A61B 10/0266* (2013.01); *A61B 10/0283* (2013.01);
(Continued)

(58) Field of Classification Search
CPC . A61B 10/04; A61B 10/0266; A61B 10/0283; A61B 2090/0801;
(Continued)

(56) References Cited

U.S. PATENT DOCUMENTS 3,612,050 A    10/1971  Sheridan
3,666,808 A     5/1972  Meek
(Continued)

FOREIGN PATENT DOCUMENTS

EP    0704189 A1    4/1996
EP    0739640 A1    4/1996
(Continued)

OTHER PUBLICATIONS

Creganna Needle Brochure, Published Jan. 16, 2008.
(Continued)

*Primary Examiner* — Rene T Towa
(74) *Attorney, Agent, or Firm* — Holland & Hart LLP

(57) ABSTRACT

A device for needle biopsy is presented. The device includes a handle member having proximal and distal portions. A proximal handle member is disposed to the proximal portion of the handle member and a distal handle member is disposed to the distal portion of the handle member. A sheath lumen is disposed within the handle member and extends from the distal portion of the handle member. A needle housing member is partially disposed to the proximal portion of the handle member and a needle is disposed within the sheath lumen. A plurality of protrusions is disposed upon the needle. A needle protection member is partially disposed to the distal portion of the needle housing member. The needle protection member includes a needle protection hub and a needle protection shaft.

20 Claims, 35 Drawing Sheets

Related U.S. Application Data continuation of application No. 12/607,636, filed on Oct. 28, 2009, now Pat. No. 8,968,210, which is a continuation-in-part of application No. 12/243,367, filed on Oct. 1, 2008, now Pat. No. 9,186,128.

(51) Int. Cl.
  *A61B 17/00* (2006.01)
  *A61B 17/34* (2006.01)
  *A61B 90/00* (2016.01)

(52) U.S. Cl.
  CPC .............. *A61B 2010/045* (2013.01); *A61B 2017/00424* (2013.01); *A61B 2017/00477* (2013.01); *A61B 2017/3413* (2013.01); *A61B 2090/0801* (2016.02); *A61B 2090/3925* (2016.02)

(58) Field of Classification Search
  CPC ...... A61B 2090/3925; A61B 2010/045; A61B 2017/00424; A61B 2017/00477; A61B 2017/3413
  See application file for complete search history.

(56) References Cited

U.S. PATENT DOCUMENTS

| | | | |
|---|---|---|---|
| 4,098,660 A | 6/1978 | McLaughlin | |
| 4,249,541 A | 2/1981 | Pratt | |
| 4,356,828 A | 11/1982 | Jamshidi | |
| 4,467,816 A | 8/1984 | Schluter et al. | |
| 4,655,226 A | 4/1987 | Lee | |
| 4,819,637 A | 4/1989 | Dormandy, Jr. et al. | |
| 4,838,280 A | 6/1989 | Haaga | |
| 4,857,057 A | 8/1989 | Sanagi | |
| 4,861,341 A | 8/1989 | Woodburn | |
| 4,893,635 A | 1/1990 | de Groot et al. | |
| 4,903,523 A | 2/1990 | Flynn | |
| 4,966,162 A | 10/1990 | Wang | |
| 4,995,866 A | 2/1991 | Amplatz et al. | |
| 5,054,310 A | 10/1991 | Flynn | |
| 5,057,085 A | 10/1991 | Kopans | |
| 5,111,829 A | 5/1992 | Alvarez de Toledo | |
| 5,131,393 A | 7/1992 | Ishiguro et al. | |
| 5,167,239 A | 12/1992 | Cohen et al. | |
| 5,215,528 A | 6/1993 | Purdy et al. | |
| 5,257,628 A | 11/1993 | Ishiguro et al. | |
| 5,266,359 A | 11/1993 | Spielvogel | |
| 5,277,199 A | 1/1994 | DuBois et al. | |
| 5,281,408 A | 1/1994 | Unger | |
| 5,320,627 A | 6/1994 | Sorensen et al. | |
| 5,333,613 A | 8/1994 | Tickner et al. | |
| 5,368,036 A | 11/1994 | Tanaka et al. | |
| 5,376,075 A | 12/1994 | Haughton | |
| 5,380,292 A | 1/1995 | Wilson | |
| 5,419,310 A | 5/1995 | Frassica et al. | |
| 5,456,673 A * | 10/1995 | Ziegler | A61B 17/3421 600/104 |
| 5,458,112 A | 10/1995 | Weaver | |
| 5,470,308 A | 11/1995 | Edwards et al. | |
| 5,471,988 A | 12/1995 | Fujio et al. | |
| 5,480,389 A | 1/1996 | McWha et al. | |
| 5,490,521 A | 2/1996 | Davis et al. | |
| 5,526,822 A | 6/1996 | Burbank et al. | |
| 5,595,724 A | 1/1997 | Grier | |
| 5,601,588 A | 2/1997 | Tonomura et al. | |
| 5,607,389 A | 3/1997 | Edwards et al. | |
| 5,609,850 A | 3/1997 | Deutsch et al. | |
| 5,636,255 A | 6/1997 | Ellis | |
| 5,681,348 A | 10/1997 | Sato | |
| 5,688,490 A | 11/1997 | Tournier et al. | |
| 5,695,491 A | 12/1997 | Silverstein | |
| 5,775,333 A | 7/1998 | Burbank et al. | |
| 5,779,686 A * | 7/1998 | Sato | A61B 10/06 604/110 |
| 5,800,445 A | 9/1998 | Ratcliff et al. | |
| 5,801,057 A | 9/1998 | Smart et al. | |
| 5,810,806 A | 9/1998 | Ritchart et al. | |
| 5,810,835 A | 9/1998 | Ryan et al. | |
| 5,848,978 A | 12/1998 | Cecchi | |
| 5,888,201 A | 3/1999 | Stinson et al. | |
| 5,902,310 A | 5/1999 | Foerster et al. | |
| 5,919,172 A | 7/1999 | Golba, Jr. | |
| 5,921,933 A | 7/1999 | Sarkis et al. | |
| 5,928,164 A | 7/1999 | Burbank et al. | |
| 5,938,635 A | 8/1999 | Kuhle | |
| 5,941,890 A | 8/1999 | Voegele et al. | |
| 5,944,673 A | 8/1999 | Gregoire et al. | |
| 5,947,964 A | 9/1999 | Eggers et al. | |
| 5,964,740 A | 10/1999 | Ouchi | |
| 5,967,988 A | 10/1999 | Briscoe et al. | |
| 5,968,022 A | 10/1999 | Saito | |
| 5,980,469 A | 11/1999 | Burbank et al. | |
| 6,019,733 A | 2/2000 | Farascioni | |
| 6,045,497 A | 4/2000 | Schweich, Jr. et al. | |
| 6,077,248 A | 6/2000 | Zumschlinge | |
| 6,080,115 A | 6/2000 | Rubinstein | |
| 6,106,473 A | 8/2000 | Violante et al. | |
| 6,106,524 A | 8/2000 | Eggers et al. | |
| 6,117,108 A | 9/2000 | Woehr et al. | |
| 6,126,633 A | 10/2000 | Kaji et al. | |
| 6,133,316 A | 10/2000 | Ostensen et al. | |
| 6,149,598 A | 11/2000 | Tanaka | |
| 6,161,034 A | 12/2000 | Burbank et al. | |
| 6,168,779 B1 | 1/2001 | Barsky et al. | |
| 6,171,249 B1 | 1/2001 | Chin et al. | |
| 6,174,291 B1 | 1/2001 | McMahon et al. | |
| 6,179,809 B1 | 1/2001 | Khairkhahan et al. | |
| 6,193,692 B1 | 2/2001 | Harris et al. | |
| 6,221,622 B1 | 4/2001 | Love | |
| 6,228,039 B1 | 5/2001 | Binmoeller | |
| 6,228,049 B1 | 5/2001 | Schroeder et al. | |
| 6,231,515 B1 | 5/2001 | Moore et al. | |
| 6,261,302 B1 | 7/2001 | Voegele et al. | |
| 6,273,861 B1 | 8/2001 | Bates et al. | |
| 6,280,399 B1 | 8/2001 | Rossin et al. | |
| 6,287,304 B1 | 9/2001 | Eggers et al. | |
| 6,312,428 B1 | 11/2001 | Eggers et al. | |
| 6,323,335 B1 | 11/2001 | Huang | |
| 6,328,701 B1 | 12/2001 | Terwilliger | |
| 6,333,155 B1 | 12/2001 | Lockhart et al. | |
| 6,334,067 B1 | 12/2001 | Brabrand | |
| 6,336,812 B1 | 1/2002 | Cooper et al. | |
| 6,337,994 B1 | 1/2002 | Stoianovici et al. | |
| 6,338,968 B1 | 1/2002 | Hefti | |
| 6,340,563 B1 | 1/2002 | Finkelstein et al. | |
| 6,340,565 B1 | 1/2002 | Oliner et al. | |
| 6,340,568 B2 | 1/2002 | Hefti | |
| 6,344,316 B1 | 2/2002 | Lockhart et al. | |
| 6,344,317 B2 | 2/2002 | Urnovitz | |
| 6,347,240 B1 | 2/2002 | Foley et al. | |
| 6,347,241 B2 | 2/2002 | Burbank et al. | |
| 6,350,244 B1 | 2/2002 | Fisher | |
| 6,350,274 B1 | 2/2002 | Li | |
| 6,350,583 B1 | 2/2002 | Cohen et al. | |
| 6,351,660 B1 | 2/2002 | Burke et al. | |
| 6,355,033 B1 | 3/2002 | Moorman et al. | |
| 6,355,275 B1 | 3/2002 | Klein | |
| 6,355,424 B1 | 3/2002 | Lorincz et al. | |
| 6,356,782 B1 | 3/2002 | Sirimanne et al. | |
| 6,361,499 B1 | 3/2002 | Bates et al. | |
| 6,361,948 B1 | 3/2002 | Tricoli et al. | |
| 6,364,526 B2 | 4/2002 | Ivan et al. | |
| 6,365,362 B1 | 4/2002 | Terstappen et al. | |
| 6,365,712 B1 | 4/2002 | Kelly | |
| 6,368,280 B1 | 4/2002 | Cermak et al. | |
| 6,368,292 B1 | 4/2002 | Ogden et al. | |
| 6,368,792 B1 | 4/2002 | Billing-Medel et al. | |
| 6,368,795 B1 | 4/2002 | Hefti | |
| 6,368,799 B1 | 4/2002 | Chee | |
| 6,369,195 B1 | 4/2002 | An et al. | |
| 6,371,904 B1 | 4/2002 | Sirimanne et al. | |
| 6,371,917 B1 | 4/2002 | Ferrara et al. | |
| 6,372,431 B1 | 4/2002 | Cunningham et al. | |

(56) References Cited

U.S. PATENT DOCUMENTS

| | | |
|---|---|---|
| 6,372,444 B1 | 4/2002 | Powers et al. |
| 6,374,135 B1 | 4/2002 | Bucholz |
| 6,375,634 B1 | 4/2002 | Carroll |
| 6,375,953 B1 | 4/2002 | Srivastava et al. |
| 6,376,258 B2 | 4/2002 | Hefti |
| 6,379,671 B1 | 4/2002 | Colpitts |
| 6,379,672 B1 | 4/2002 | Srivastava et al. |
| 6,383,484 B1 | 5/2002 | Achen et al. |
| 6,383,491 B1 | 5/2002 | Srivastava et al. |
| 6,383,492 B1 | 5/2002 | Srivastava et al. |
| 6,383,493 B1 | 5/2002 | Srivastava et al. |
| 6,387,056 B1 | 5/2002 | Kieturakis |
| 6,387,374 B1 | 5/2002 | Srivastava et al. |
| 6,387,629 B1 | 5/2002 | Schneider et al. |
| 6,391,306 B1 | 5/2002 | Srivastava et al. |
| 6,391,542 B1 | 5/2002 | Anderson et al. |
| 6,391,543 B2 | 5/2002 | Billing-Medel et al. |
| 6,394,965 B1 | 5/2002 | Klein |
| 6,395,480 B1 | 5/2002 | Hefti |
| 6,398,737 B2 | 6/2002 | Moore et al. |
| 6,399,069 B1 | 6/2002 | Srivastava et al. |
| 6,399,070 B1 | 6/2002 | Srivastava et al. |
| 6,399,371 B1 | 6/2002 | Falduto et al. |
| 6,402,701 B1 | 6/2002 | Kaplan et al. |
| 6,403,095 B1 | 6/2002 | Srivastava et al. |
| 6,405,733 B1 | 6/2002 | Fogarty et al. |
| 6,407,125 B1 | 6/2002 | Fernandez-Pol |
| 6,409,664 B1 | 6/2002 | Kattan et al. |
| 6,410,028 B1 | 6/2002 | Srivastava |
| 6,410,229 B1 | 6/2002 | Lockhart et al. |
| 6,413,751 B1 | 7/2002 | Benkovic et al. |
| 6,416,484 B1 | 7/2002 | Miller et al. |
| 6,421,559 B1 | 7/2002 | Pearlman |
| 6,423,081 B1 | 7/2002 | Lee et al. |
| 6,423,313 B1 | 7/2002 | Esmon et al. |
| 6,423,489 B1 | 7/2002 | Anderson et al. |
| 6,423,494 B1 | 7/2002 | Jin et al. |
| 6,423,503 B1 | 7/2002 | Mikolajczyk et al. |
| 6,426,195 B1 | 7/2002 | Zhong et al. |
| 6,426,367 B1 | 7/2002 | Das |
| 6,427,081 B1 | 7/2002 | Burbank et al. |
| 6,427,089 B1 | 7/2002 | Knowlton |
| 6,428,463 B1 | 8/2002 | Ravins et al. |
| 6,428,479 B1 | 8/2002 | Aksnes et al. |
| 6,428,487 B1 | 8/2002 | Burdorff et al. |
| 6,432,035 B1 | 8/2002 | Ravins et al. |
| 6,432,053 B1 | 8/2002 | Fecht et al. |
| 6,432,065 B1 | 8/2002 | Burdorff et al. |
| 6,432,700 B1 | 8/2002 | Henderson et al. |
| 6,434,415 B1 | 8/2002 | Foley et al. |
| 6,436,054 B1 | 8/2002 | Viola et al. |
| 6,436,120 B1 | 8/2002 | Meglin |
| 6,436,394 B1 | 8/2002 | Henderson et al. |
| 6,436,404 B1 | 8/2002 | Srivastava et al. |
| 6,436,411 B1 | 8/2002 | Riordan et al. |
| 6,440,086 B1 | 8/2002 | Hohenberg |
| 6,440,147 B1 | 8/2002 | Lee et al. |
| 6,440,151 B1 | 8/2002 | Cragg et al. |
| 6,440,153 B2 | 8/2002 | Cragg et al. |
| 6,443,960 B1 | 9/2002 | Brabrand et al. |
| 6,445,767 B1 | 9/2002 | Karellas |
| 6,447,477 B2 | 9/2002 | Burney et al. |
| 6,447,534 B2 | 9/2002 | Cragg et al. |
| 6,447,780 B1 | 9/2002 | Srivastava et al. |
| 6,447,781 B1 | 9/2002 | Srivastava |
| 6,447,997 B1 | 9/2002 | Los et al. |
| 6,448,020 B1 | 9/2002 | Toftgard et al. |
| 6,450,973 B1 | 9/2002 | Murphy |
| 6,455,027 B1 | 9/2002 | Barsky et al. |
| 6,455,048 B1 | 9/2002 | Srivastava et al. |
| 6,455,251 B1 | 9/2002 | Waldman |
| 6,459,925 B1 | 10/2002 | Nields et al. |
| 6,461,615 B1 | 10/2002 | Srivastava |
| 6,463,319 B1 | 10/2002 | Bucholz |
| 6,464,648 B1 | 10/2002 | Nakamura |
| 6,465,181 B2 | 10/2002 | Billing-Medel et al. |
| 6,465,183 B2 | 10/2002 | Wober |
| 6,468,985 B1 | 10/2002 | Huang |
| 6,470,217 B1 | 10/2002 | Fenn et al. |
| 6,471,659 B2 | 10/2002 | Eggers et al. |
| 6,471,678 B1 | 10/2002 | Alvarez de Toledo |
| 6,471,700 B1 | 10/2002 | Burbank et al. |
| 6,471,709 B1 | 10/2002 | Fawzi et al. |
| 6,472,518 B1 | 10/2002 | Ribot et al. |
| 6,475,732 B1 | 11/2002 | Shayesteh et al. |
| 6,475,789 B1 | 11/2002 | Cech et al. |
| 6,477,426 B1 | 11/2002 | Fenn et al. |
| 6,482,182 B1 | 11/2002 | Carroll et al. |
| 6,482,599 B1 | 11/2002 | Mikolajczyk et al. |
| 6,485,308 B1 | 11/2002 | Goldstein |
| 6,485,436 B1 | 11/2002 | Truckai et al. |
| 6,485,905 B2 | 11/2002 | Hefti |
| 6,488,636 B2 | 12/2002 | Bryan et al. |
| 6,489,097 B2 | 12/2002 | Hirose et al. |
| 6,489,113 B1 | 12/2002 | Traish |
| 6,490,467 B1 | 12/2002 | Bucholz et al. |
| 6,491,699 B1 | 12/2002 | Henderson et al. |
| 6,491,702 B2 | 12/2002 | Heilbrun et al. |
| 6,492,115 B1 | 12/2002 | Guida et al. |
| 6,494,844 B1 | 12/2002 | Van Bladel et al. |
| 6,494,859 B2 | 12/2002 | Love et al. |
| 6,494,879 B2 | 12/2002 | Lennox et al. |
| 6,495,130 B1 | 12/2002 | Henderson et al. |
| 6,496,717 B2 | 12/2002 | Cox et al. |
| 6,497,706 B1 | 12/2002 | Burbank et al. |
| 6,500,622 B2 | 12/2002 | Bruchez, Jr. et al. |
| 6,500,938 B1 | 12/2002 | Au-Young et al. |
| 6,505,125 B1 | 1/2003 | Ho |
| 6,506,156 B1 | 1/2003 | Jones et al. |
| 6,506,607 B1 | 1/2003 | Shyjan |
| 6,507,748 B2 | 1/2003 | Selland |
| 6,508,755 B1 | 1/2003 | Ravins et al. |
| 6,508,789 B1 | 1/2003 | Sinnott et al. |
| 6,509,458 B1 | 1/2003 | Afar et al. |
| 6,509,514 B1 | 1/2003 | Kneteman et al. |
| 6,514,248 B1 | 2/2003 | Eggers et al. |
| 6,514,251 B1 | 2/2003 | Ni et al. |
| 6,514,685 B1 | 2/2003 | Moro |
| 6,514,695 B1 | 2/2003 | Barsky et al. |
| 6,517,498 B1 | 2/2003 | Burbank et al. |
| 6,521,211 B1 | 2/2003 | Unger et al. |
| 6,524,800 B2 | 2/2003 | Lockhart et al. |
| 6,527,731 B2 | 3/2003 | Weiss et al. |
| 6,530,888 B2 | 3/2003 | Smith et al. |
| 6,535,756 B1 | 3/2003 | Simon et al. |
| 6,537,761 B1 | 3/2003 | Shayesteh et al. |
| 6,538,119 B2 | 3/2003 | Billing-Medel et al. |
| 6,540,694 B1 | 4/2003 | Van Bladel et al. |
| 6,540,695 B1 | 4/2003 | Burbank et al. |
| 6,544,236 B1 | 4/2003 | Cragg et al. |
| 6,544,544 B2 | 4/2003 | Hunter et al. |
| 6,546,787 B1 | 4/2003 | Schiller et al. |
| 6,548,257 B2 | 4/2003 | Lockhart et al. |
| 6,551,255 B2 | 4/2003 | Van Bladel et al. |
| 6,551,784 B2 | 4/2003 | Fodor et al. |
| 6,552,164 B1 | 4/2003 | Colpitts et al. |
| 6,552,181 B1 | 4/2003 | Dean et al. |
| 6,554,779 B2 | 4/2003 | Viola et al. |
| 6,558,407 B1 | 5/2003 | Ivanko et al. |
| 6,558,916 B2 | 5/2003 | Veerapandian et al. |
| 6,562,562 B1 | 5/2003 | Casu' et al. |
| 6,564,087 B1 | 5/2003 | Pitris et al. |
| 6,564,806 B1 | 5/2003 | Fogarty et al. |
| 6,566,078 B1 | 5/2003 | Raitano et al. |
| 6,566,079 B2 | 5/2003 | Hefti |
| 6,567,214 B2 | 5/2003 | Lorincz |
| 6,567,689 B2 | 5/2003 | Burbank et al. |
| 6,568,941 B1 | 5/2003 | Goldstein |
| 6,572,551 B1 | 6/2003 | Smith et al. |
| 6,572,578 B1 | 6/2003 | Blanchard |
| 6,577,904 B1 | 6/2003 | Zhang et al. |
| 6,579,891 B1 | 6/2003 | Fernandez-Pol |
| 6,580,938 B1 | 6/2003 | Acker |
| 6,582,368 B2 | 6/2003 | Holdaway et al. |

(56) References Cited

U.S. PATENT DOCUMENTS

| | | |
|---|---|---|
| 6,582,426 B2 | 6/2003 | Moorman et al. |
| 6,585,968 B2 | 7/2003 | Little et al. |
| 6,586,713 B2 | 7/2003 | Essenfeld et al. |
| 6,587,578 B2 | 7/2003 | Godik et al. |
| 6,589,240 B2 | 7/2003 | Hinchliffe |
| 6,592,508 B1 | 7/2003 | Ravins et al. |
| 6,592,530 B1 | 7/2003 | Farhadi |
| 6,599,247 B1 | 7/2003 | Stetten |
| 6,602,659 B1 | 8/2003 | Waldman et al. |
| 6,604,404 B2 | 8/2003 | Paltieli et al. |
| 6,605,294 B2 | 8/2003 | Sawhney |
| 6,607,561 B2 | 8/2003 | Brannon |
| 6,608,191 B1 | 8/2003 | Anderson et al. |
| 6,608,310 B2 | 8/2003 | Soluri et al. |
| 6,610,016 B1 | 8/2003 | Violante et al. |
| 6,610,499 B1 | 8/2003 | Fulwyler et al. |
| 6,610,839 B1 | 8/2003 | Morin et al. |
| 6,612,991 B2 | 9/2003 | Sauer et al. |
| 6,613,740 B1 | 9/2003 | Gozes et al. |
| 6,614,921 B1 | 9/2003 | Chung et al. |
| 6,617,110 B1 | 9/2003 | Chech et al. |
| 6,617,137 B2 | 9/2003 | Dean et al. |
| 6,623,437 B2 | 9/2003 | Hinchliffe et al. |
| 6,626,832 B1 | 9/2003 | Paltieli et al. |
| 6,626,848 B2 | 9/2003 | Neuenfeldt |
| 6,626,850 B1 | 9/2003 | Chau et al. |
| 6,626,903 B2 | 9/2003 | McGuckin, Jr. et al. |
| 6,626,930 B1 | 9/2003 | Allen et al. |
| 6,627,414 B2 | 9/2003 | Billing-Medel et al. |
| 6,627,461 B2 | 9/2003 | Chapman et al. |
| 6,629,959 B2 | 10/2003 | Kuracina et al. |
| 6,631,204 B1 | 10/2003 | Smith |
| 6,632,183 B2 | 10/2003 | Bowman et al. |
| 6,638,234 B2 | 10/2003 | Burbank et al. |
| 6,638,719 B1 | 10/2003 | Gunderson et al. |
| 6,638,727 B1 | 10/2003 | Hung et al. |
| 6,645,731 B2 | 11/2003 | Terstappen et al. |
| 6,647,285 B2 | 11/2003 | Da Silva et al. |
| 6,649,420 B1 | 11/2003 | Cantor |
| 6,652,520 B2 | 11/2003 | Moorman et al. |
| 6,652,859 B1 | 11/2003 | Afar et al. |
| 6,653,080 B2 | 11/2003 | Bruchez et al. |
| 6,653,129 B1 | 11/2003 | Bander et al. |
| 6,654,120 B2 | 11/2003 | Ban |
| 6,654,629 B2 | 11/2003 | Montegrande |
| 6,656,132 B1 | 12/2003 | Ouchi |
| 6,659,105 B2 | 12/2003 | Burbank et al. |
| 6,660,834 B2 | 12/2003 | Billing-Medel et al. |
| 6,662,041 B2 | 12/2003 | Burbank et al. |
| 6,663,560 B2 | 12/2003 | MacAulay et al. |
| 6,666,811 B1 | 12/2003 | Good |
| 6,670,122 B2 | 12/2003 | Rosenow et al. |
| 6,673,023 B2 | 1/2004 | Pflueger |
| 6,673,914 B1 | 1/2004 | Hoon |
| 6,675,037 B1 | 1/2004 | Tsekos |
| 6,676,610 B2 | 1/2004 | Morton et al. |
| 6,676,658 B2 | 1/2004 | Burbank et al. |
| 6,676,935 B2 | 1/2004 | Henderson et al. |
| 6,676,984 B1 | 1/2004 | Sharp et al. |
| 6,677,157 B1 | 1/2004 | Cohen |
| 6,678,545 B2 | 1/2004 | Bucholz |
| 6,678,552 B2 | 1/2004 | Pearlman |
| 6,679,851 B2 | 1/2004 | Burbank et al. |
| 6,680,178 B2 | 1/2004 | Harris et al. |
| 6,689,062 B1 | 2/2004 | Mesallum |
| 6,689,065 B2 | 2/2004 | Aksnes et al. |
| 6,689,067 B2 | 2/2004 | Sauer et al. |
| 6,689,071 B2 | 2/2004 | Burbank et al. |
| 6,689,072 B2 | 2/2004 | Kaplan et al. |
| 6,689,073 B2 | 2/2004 | Quay |
| 6,689,744 B2 | 2/2004 | Gao et al. |
| 6,689,787 B1 | 2/2004 | McKearn et al. |
| 6,690,371 B1 | 2/2004 | Okerlund et al. |
| 6,690,966 B1 | 2/2004 | Rava et al. |
| 6,690,976 B2 | 2/2004 | Fenn et al. |
| 6,692,467 B2 | 2/2004 | McFarlane |
| 6,692,724 B1 | 2/2004 | Yang et al. |
| 6,692,736 B2 | 2/2004 | Yu et al. |
| 6,695,779 B2 | 2/2004 | Sauer et al. |
| 6,697,665 B1 | 2/2004 | Rava et al. |
| 6,699,205 B2 | 3/2004 | Fulton, III et al. |
| 6,702,749 B2 | 3/2004 | Paladini et al. |
| 6,702,761 B1 | 3/2004 | Damadian et al. |
| 6,702,831 B2 | 3/2004 | Lee et al. |
| 6,703,216 B2 | 3/2004 | Parsons et al. |
| 6,705,994 B2 | 3/2004 | Vortman et al. |
| 6,709,408 B2 | 3/2004 | Fisher |
| 6,709,816 B1 | 3/2004 | Huang et al. |
| 6,712,773 B1 | 3/2004 | Viola |
| 6,712,785 B2 | 3/2004 | Morton et al. |
| 6,714,808 B2 | 3/2004 | Klimberg et al. |
| 6,716,179 B2 | 4/2004 | Burbank et al. |
| 6,722,371 B1 | 4/2004 | Fogarty et al. |
| 6,723,052 B2 | 4/2004 | Mills |
| 6,723,106 B1 | 4/2004 | Charles et al. |
| 6,723,498 B1 | 4/2004 | Shyjan et al. |
| 6,725,080 B2 | 4/2004 | Melkent et al. |
| 6,725,083 B1 | 4/2004 | Burbank et al. |
| 6,725,095 B2 | 4/2004 | Fenn et al. |
| 6,726,651 B1 | 4/2004 | Robinson et al. |
| 6,728,334 B1 | 4/2004 | Zhao |
| 6,730,042 B2 | 5/2004 | Fulton et al. |
| 6,730,045 B2 | 5/2004 | Finer |
| 6,731,966 B1 | 5/2004 | Spigelman et al. |
| 6,733,969 B2 | 5/2004 | Mack |
| 6,738,663 B2 | 5/2004 | Schroeppel et al. |
| 6,746,844 B2 | 6/2004 | Oliner et al. |
| 6,749,588 B1 * | 6/2004 | Howell ............... A61M 5/3273 604/110 |
| 6,750,015 B2 | 6/2004 | Horwitz et al. |
| 6,752,154 B2 | 6/2004 | Fogarty et al. |
| 6,752,767 B2 | 6/2004 | Turovskiy et al. |
| 6,752,768 B2 | 6/2004 | Burdorff et al. |
| 6,752,769 B2 | 6/2004 | Alberico |
| 6,753,138 B1 | 6/2004 | Schneider et al. |
| 6,758,848 B2 | 7/2004 | Burbank et al. |
| 6,764,449 B2 | 7/2004 | Lee et al. |
| 6,764,495 B2 | 7/2004 | Lee et al. |
| 6,766,186 B1 | 7/2004 | Hoyns et al. |
| 6,767,704 B2 | 7/2004 | Waldman et al. |
| 6,768,925 B2 | 7/2004 | Fenn et al. |
| 6,770,066 B1 | 8/2004 | Weaver et al. |
| 6,770,070 B1 | 8/2004 | Balbierz |
| 6,770,435 B1 | 8/2004 | Billing-Medel et al. |
| 6,770,770 B1 | 8/2004 | Baumann et al. |
| 6,773,903 B2 | 8/2004 | Bova |
| 6,776,757 B2 | 8/2004 | Larson et al. |
| 6,780,984 B2 | 8/2004 | Wang et al. |
| 6,785,410 B2 | 8/2004 | Vining et al. |
| 6,786,870 B2 | 9/2004 | Miyaki et al. |
| 6,788,977 B2 | 9/2004 | Fenn et al. |
| 6,790,185 B1 | 9/2004 | Fisher et al. |
| 6,797,477 B2 | 9/2004 | Guida et al. |
| 6,805,669 B2 | 10/2004 | Swanbom |
| 6,805,869 B2 | 10/2004 | Guo |
| 6,806,712 B2 | 10/2004 | Akgun |
| 6,807,444 B2 | 10/2004 | Tu et al. |
| 6,808,878 B1 | 10/2004 | Gray et al. |
| 6,818,184 B2 | 11/2004 | Fulwyler et al. |
| 6,818,750 B2 | 11/2004 | Reed |
| 6,819,785 B1 | 11/2004 | Vining et al. |
| 6,821,725 B1 | 11/2004 | Carrasco et al. |
| 6,824,780 B1 | 11/2004 | Devaux et al. |
| 6,824,974 B2 | 11/2004 | Pisharody et al. |
| 6,824,995 B1 | 11/2004 | Wu |
| 6,827,692 B2 | 12/2004 | Castellacci |
| 6,831,059 B2 | 12/2004 | Donovan |
| 6,832,111 B2 | 12/2004 | Tu et al. |
| 6,833,373 B1 | 12/2004 | McKearn et al. |
| 6,833,438 B1 | 12/2004 | Afar et al. |
| 6,835,183 B2 | 12/2004 | Lennox et al. |
| 6,835,572 B1 | 12/2004 | Mountford et al. |
| 6,838,243 B2 | 1/2005 | Lai et al. |
| 6,840,952 B2 | 1/2005 | Saker et al. |

(56) References Cited

U.S. PATENT DOCUMENTS

| | | |
|---|---|---|
| 6,841,350 B2 | 1/2005 | Ogden et al. |
| 6,843,980 B2 | 1/2005 | Green |
| 6,844,153 B2 | 1/2005 | Waldman et al. |
| 6,846,320 B2 | 1/2005 | Ashby et al. |
| 6,846,650 B2 | 1/2005 | Recipon et al. |
| 6,846,911 B2 | 1/2005 | Kelly |
| 6,847,841 B1 | 1/2005 | El Hatw |
| 6,849,080 B2 | 2/2005 | Lee et al. |
| 6,850,588 B2 | 2/2005 | Arenson et al. |
| 6,852,528 B2 | 2/2005 | Yu et al. |
| 6,855,517 B2 | 2/2005 | Salceda et al. |
| 6,855,554 B2 | 2/2005 | Fritsche et al. |
| 6,858,412 B2 | 2/2005 | Willis et al. |
| 6,858,598 B1 | 2/2005 | McKearn et al. |
| 6,858,711 B2 | 2/2005 | McGall et al. |
| 6,859,049 B2 | 2/2005 | Khatchatrian et al. |
| 6,860,855 B2 | 3/2005 | Shelby et al. |
| 6,860,860 B2 | 3/2005 | Viola |
| 6,863,676 B2 | 3/2005 | Lee et al. |
| 6,864,224 B1 | 3/2005 | Sedivy et al. |
| 6,866,630 B2 | 3/2005 | Larson et al. |
| 6,866,993 B1 | 3/2005 | Williamson |
| 6,866,994 B2 | 3/2005 | Morton |
| 6,867,016 B1 | 3/2005 | Billing-Medel et al. |
| 6,867,753 B2 | 3/2005 | Chinthammit et al. |
| 6,871,086 B2 | 3/2005 | Nevo et al. |
| 6,872,184 B2 | 3/2005 | Brannon |
| 6,872,185 B2 | 3/2005 | Fisher |
| 6,872,389 B1 | 3/2005 | Faris |
| 6,875,182 B2 | 4/2005 | Wardle et al. |
| 6,875,184 B2 | 4/2005 | Morton et al. |
| 6,883,194 B2 | 4/2005 | Corbeil et al. |
| 6,883,958 B2 | 4/2005 | Mayer |
| 6,884,578 B2 | 4/2005 | Warrington et al. |
| 6,884,605 B2 | 4/2005 | Hermonat et al. |
| 6,887,210 B2 | 5/2005 | Quay |
| 6,888,919 B2 | 5/2005 | Graf |
| 6,890,308 B2 | 5/2005 | Islam |
| 6,890,309 B2 | 5/2005 | Fisher |
| 6,890,311 B2 | 5/2005 | Love et al. |
| 6,890,749 B2 | 5/2005 | Billing-Medel et al. |
| 6,893,818 B1 | 5/2005 | Afar et al. |
| 6,893,868 B2 | 5/2005 | Packard et al. |
| 6,894,026 B1 | 5/2005 | Quay |
| 6,899,696 B2 | 5/2005 | Morton et al. |
| 6,900,015 B2 | 5/2005 | Avihingsanon et al. |
| 6,900,049 B2 | 5/2005 | Yu et al. |
| 6,901,278 B1 | 5/2005 | Notelovitz |
| 6,904,305 B2 | 6/2005 | Tsekos |
| 6,904,309 B2 | 6/2005 | Derendorf et al. |
| 6,905,475 B2 | 6/2005 | Hauschild et al. |
| 6,908,440 B2 | 6/2005 | Fisher |
| 6,913,882 B2 | 7/2005 | Glynne et al. |
| 6,914,130 B2 | 7/2005 | Gao et al. |
| 6,916,800 B2 | 7/2005 | McKearn et al. |
| 6,916,918 B2 | 7/2005 | Yu et al. |
| 6,918,881 B2 | 7/2005 | Miller et al. |
| 6,919,176 B2 | 7/2005 | Yang et al. |
| 6,920,347 B2 | 7/2005 | Simon et al. |
| RE38,776 E | 8/2005 | Bauer |
| 6,923,809 B2 | 8/2005 | Eggers et al. |
| 6,924,094 B1 | 8/2005 | Gingeras et al. |
| 6,925,389 B2 | 8/2005 | Hitt et al. |
| 6,926,893 B1 | 8/2005 | Hansen |
| 6,927,032 B2 | 8/2005 | Lockhart et al. |
| 6,933,105 B2 | 8/2005 | Jin |
| 6,936,014 B2 | 8/2005 | Vetter et al. |
| 6,936,416 B2 | 8/2005 | Zhu et al. |
| 6,936,687 B1 | 8/2005 | Komoriya et al. |
| 6,942,985 B2 | 9/2005 | Waldman |
| 6,943,236 B2 | 9/2005 | Xu et al. |
| 6,944,505 B2 | 9/2005 | Zhang et al. |
| 6,945,942 B2 | 9/2005 | Van Bladel et al. |
| 6,947,584 B1 | 9/2005 | Avila et al. |
| 6,949,357 B2 | 9/2005 | Billing-Medel et al. |
| 6,953,691 B2 | 10/2005 | Reed et al. |
| 6,954,667 B2 | 10/2005 | Treado et al. |
| 6,955,653 B2 | 10/2005 | Eggers |
| 6,965,793 B2 | 11/2005 | Treado et al. |
| 6,994,712 B1 | 2/2006 | Fisher et al. |
| D518,175 S | 3/2006 | Hardin, Jr. et al. |
| 7,014,610 B2 | 3/2006 | Koulik |
| 7,025,765 B2 | 4/2006 | Balbierz et al. |
| 7,067,111 B1 | 6/2006 | Yang et al. |
| 7,067,274 B2 | 6/2006 | Fairbrother et al. |
| 7,070,816 B2 | 7/2006 | Newmark et al. |
| 7,072,704 B2 | 7/2006 | Bucholz |
| 7,074,600 B2 | 7/2006 | Dean et al. |
| 7,077,842 B1 | 7/2006 | Cosman |
| 7,079,132 B2 | 7/2006 | Sauer et al. |
| 7,081,340 B2 | 7/2006 | Baker et al. |
| 7,083,547 B2 | 8/2006 | LaStayo et al. |
| 7,083,985 B2 | 8/2006 | Hefti et al. |
| 7,087,393 B2 | 8/2006 | Billing-Medel et al. |
| 7,089,121 B1 | 8/2006 | Wang |
| 7,090,845 B2 | 8/2006 | Fong et al. |
| 7,090,862 B2 | 8/2006 | Barrett-Reis et al. |
| 7,091,047 B2 | 8/2006 | Serrero |
| 7,094,233 B2 | 8/2006 | Desinger |
| 7,101,663 B2 | 9/2006 | Godfrey et al. |
| 7,101,862 B2 | 9/2006 | Cochrum et al. |
| 7,108,969 B1 | 9/2006 | Warrington et al. |
| 7,115,368 B2 | 10/2006 | Powers et al. |
| 7,118,876 B2 | 10/2006 | Tyner et al. |
| 7,118,910 B2 | 10/2006 | Unger et al. |
| 7,122,011 B2 | 10/2006 | Clifford et al. |
| 7,122,653 B2 | 10/2006 | Cohen et al. |
| 7,125,836 B2 | 10/2006 | Woodward |
| 7,125,969 B1 | 10/2006 | Benz et al. |
| 7,128,877 B2 | 10/2006 | Quay et al. |
| 7,128,893 B2 | 10/2006 | Leamon et al. |
| 7,129,048 B2 | 10/2006 | Bruchez et al. |
| 7,131,951 B2 | 11/2006 | Angel |
| 7,135,333 B1 | 11/2006 | Waldman et al. |
| 7,139,601 B2 | 11/2006 | Bucholz et al. |
| 7,141,019 B2 | 11/2006 | Pearlman |
| 7,144,950 B2 | 12/2006 | Bazan et al. |
| 7,153,700 B1 | 12/2006 | Pardee et al. |
| 7,156,814 B2 | 1/2007 | Williamson, IV et al. |
| 7,156,815 B2 | 1/2007 | Leigh et al. |
| 7,160,292 B2 | 1/2007 | Moorman et al. |
| 7,161,057 B2 | 1/2007 | Kneteman et al. |
| 7,169,114 B2 | 1/2007 | Krause |
| 7,172,558 B2 | 2/2007 | Olson, Jr. |
| 7,172,739 B2 | 2/2007 | Maughan |
| 7,175,839 B1 | 2/2007 | Hiserodt |
| 7,183,251 B1 | 2/2007 | Russo et al. |
| D538,933 S | 3/2007 | Andrade |
| 7,186,522 B2 | 3/2007 | Lapen et al. |
| 7,189,206 B2 | 3/2007 | Quick et al. |
| 7,189,207 B2 | 3/2007 | Viola |
| 7,190,378 B2 | 3/2007 | Sauer et al. |
| 7,192,570 B2 | 3/2007 | Maecke et al. |
| 7,195,774 B2 | 3/2007 | Carvalho et al. |
| 7,195,868 B2 | 3/2007 | Iartchouk et al. |
| 7,195,911 B2 | 3/2007 | Cech et al. |
| 7,196,182 B2 | 3/2007 | Reed et al. |
| 7,198,896 B2 | 4/2007 | Rush et al. |
| 7,199,234 B2 | 4/2007 | Morin et al. |
| 7,204,988 B2 | 4/2007 | Cheung |
| 7,207,985 B2 | 4/2007 | Duong et al. |
| 7,208,146 B2 | 4/2007 | Denney, Jr. |
| 7,208,267 B2 | 4/2007 | Salceda et al. |
| 7,211,398 B2 | 5/2007 | Astle et al. |
| 7,214,489 B2 | 5/2007 | Bazan et al. |
| 7,217,276 B2 | 5/2007 | Henderson et al. |
| 7,217,394 B2 | 5/2007 | Studer |
| 7,218,959 B2 | 5/2007 | Alfano et al. |
| 7,220,258 B2 | 5/2007 | Myhr |
| 7,220,891 B2 | 5/2007 | Barsky et al. |
| 7,223,238 B2 | 5/2007 | Swanbom |
| 7,223,380 B2 | 5/2007 | Yang et al. |
| 7,223,540 B2 | 5/2007 | Pourmand et al. |
| 7,223,542 B2 | 5/2007 | Raitano et al. |

(56) References Cited

U.S. PATENT DOCUMENTS

| | | |
|---|---|---|
| 7,226,731 B1 | 6/2007 | Chuaqui et al. |
| 7,227,009 B2 | 6/2007 | Craik et al. |
| 7,229,413 B2 | 6/2007 | Violante et al. |
| 7,229,417 B2 | 6/2007 | Foerster et al. |
| 7,229,439 B2 | 6/2007 | Burbank et al. |
| 7,229,604 B2 | 6/2007 | Yang et al. |
| 7,229,774 B2 | 6/2007 | Chinnaiyan et al. |
| 7,231,015 B2 | 6/2007 | Kumakhov |
| 7,235,047 B2 | 6/2007 | MacAulay et al. |
| 7,236,816 B2 | 6/2007 | Kumar et al. |
| 7,241,736 B2 | 7/2007 | Hunter et al. |
| 7,244,619 B2 | 7/2007 | Contreras et al. |
| 7,245,748 B2 | 7/2007 | Degani et al. |
| 7,245,958 B1 | 7/2007 | Navab et al. |
| 7,247,426 B2 | 7/2007 | Yakhini et al. |
| 7,250,180 B2 | 7/2007 | Arellano |
| 7,250,264 B2 | 7/2007 | Fong et al. |
| 7,250,551 B2 | 7/2007 | Tsai et al. |
| 7,251,352 B2 | 7/2007 | Sauer et al. |
| 7,251,568 B2 | 7/2007 | Pittman et al. |
| 7,252,935 B2 | 8/2007 | Sidransky |
| 7,252,946 B2 | 8/2007 | Szasz |
| 7,252,948 B2 | 8/2007 | Gingeras et al. |
| 7,258,973 B2 | 8/2007 | Astle et al. |
| 7,261,712 B2 | 8/2007 | Burbank et al. |
| 7,261,875 B2 | 8/2007 | Li et al. |
| 7,262,288 B1 | 8/2007 | Cech et al. |
| 7,264,947 B2 | 9/2007 | Gozes et al. |
| 7,270,956 B2 | 9/2007 | Bazan et al. |
| 7,271,187 B2 | 9/2007 | Neuberger et al. |
| 7,274,810 B2 | 9/2007 | Reeves et al. |
| 7,314,481 B2 | 1/2008 | Karpiel |
| 7,356,828 B2 | 4/2008 | Townsend et al. |
| 7,608,056 B2 | 10/2009 | Kennedy, II |
| 8,109,953 B1 | 2/2012 | King, III et al. |
| D657,461 S | 4/2012 | Schembre et al. |
| 8,162,958 B2 | 4/2012 | Takahashi et al. |
| 8,187,203 B2 | 5/2012 | McClellan |
| 8,262,680 B2 | 9/2012 | Swain et al. |
| 8,328,772 B2 | 12/2012 | Kinast et al. |
| 8,357,193 B2 | 1/2013 | Phan et al. |
| 8,361,041 B2 | 1/2013 | Fang et al. |
| 8,454,632 B2 | 6/2013 | Binmoeller et al. |
| 8,486,010 B2 | 7/2013 | Nomura |
| D690,009 S | 9/2013 | Schembre et al. |
| 8,968,210 B2 | 3/2015 | Mugan et al. |
| 9,186,128 B2 | 11/2015 | Mugan et al. |
| 2001/0007925 A1 | 7/2001 | Ritchart et al. |
| 2001/0023322 A1 | 9/2001 | Esposito et al. |
| 2001/0047183 A1 | 11/2001 | Privitera et al. |
| 2001/0056218 A1 | 12/2001 | Hogendijk et al. |
| 2002/0035324 A1 | 3/2002 | Sirimanne et al. |
| 2002/0082519 A1 | 6/2002 | Miller et al. |
| 2002/0156395 A1 | 10/2002 | Stephens et al. |
| 2002/0169418 A1 | 11/2002 | Menz et al. |
| 2003/0078502 A1 | 4/2003 | Miyaki et al. |
| 2003/0093007 A1 | 5/2003 | Wood |
| 2003/0105488 A1 | 6/2003 | Chu |
| 2003/0139752 A1 | 7/2003 | Pasricha et al. |
| 2003/0163142 A1 | 8/2003 | Paltieli et al. |
| 2003/0181823 A1 | 9/2003 | Gatto |
| 2003/0195436 A1 | 10/2003 | Van Bladel et al. |
| 2003/0204137 A1 | 10/2003 | Chesbrough et al. |
| 2003/0208134 A1 | 11/2003 | Secrest et al. |
| 2003/0208219 A1 | 11/2003 | Aznolan et al. |
| 2003/0212394 A1 | 11/2003 | Pearson et al. |
| 2003/0233101 A1 | 12/2003 | Lubock et al. |
| 2004/0073219 A1 | 4/2004 | Skiba et al. |
| 2004/0077948 A1 | 4/2004 | Violante et al. |
| 2004/0153005 A1 | 8/2004 | Krueger |
| 2004/0167429 A1 | 8/2004 | Roshdieh et al. |
| 2004/0236212 A1 | 11/2004 | Jones et al. |
| 2004/0249395 A1 | 12/2004 | Mikkaichi et al. |
| 2004/0260199 A1 | 12/2004 | Hardia, Jr. et al. |
| 2004/0260274 A1 | 12/2004 | Hardin et al. |
| 2005/0021003 A1 | 1/2005 | Caso et al. |
| 2005/0022493 A1 | 2/2005 | Olinger et al. |
| 2005/0061697 A1 | 3/2005 | Moberg |
| 2005/0090801 A1 | 4/2005 | Racz et al. |
| 2005/0113715 A1 | 5/2005 | Schwindt et al. |
| 2005/0143753 A1 | 6/2005 | Whitmore et al. |
| 2005/0159676 A1 | 7/2005 | Taylor et al. |
| 2005/0192535 A1 | 9/2005 | Takagi et al. |
| 2005/0197623 A1 | 9/2005 | Leeflang et al. |
| 2005/0228311 A1 | 10/2005 | Beckman et al. |
| 2005/0228312 A1 | 10/2005 | Surti |
| 2005/0228413 A1 | 10/2005 | Binmoeller et al. |
| 2005/0251111 A1 | 11/2005 | Saito et al. |
| 2005/0256426 A1 | 11/2005 | Brugge |
| 2005/0272975 A1 | 12/2005 | Mcweeney et al. |
| 2006/0052750 A1 | 3/2006 | Lenker et al. |
| 2006/0100654 A1 | 5/2006 | Fukuda et al. |
| 2006/0116605 A1 | 6/2006 | Nakao |
| 2006/0142789 A1 | 6/2006 | Lehman et al. |
| 2006/0155210 A1 | 7/2006 | Beckman et al. |
| 2006/0155246 A1* | 7/2006 | Higuchi ............ A61B 17/3401 604/165.01 |
| 2006/0167416 A1 | 7/2006 | Mathis et al. |
| 2006/0189891 A1 | 8/2006 | Waxman et al. |
| 2006/0235298 A1 | 10/2006 | Kotmel et al. |
| 2006/0247530 A1 | 11/2006 | Hardin et al. |
| 2006/0258955 A1 | 11/2006 | Hoffman et al. |
| 2006/0264919 A1 | 11/2006 | Schaaf |
| 2007/0023304 A1 | 2/2007 | Joyce et al. |
| 2007/0032741 A1 | 2/2007 | Hibner et al. |
| 2007/0038089 A1 | 2/2007 | Hatano et al. |
| 2007/0055173 A1 | 3/2007 | Delonzor et al. |
| 2007/0056360 A1 | 3/2007 | Grant et al. |
| 2007/0060837 A1 | 3/2007 | Cho et al. |
| 2007/0118049 A1 | 5/2007 | Viola |
| 2007/0123799 A1 | 5/2007 | Meireles |
| 2007/0123800 A1 | 5/2007 | Nishtala et al. |
| 2007/0149893 A1 | 6/2007 | Heske et al. |
| 2007/0177009 A1 | 8/2007 | Bayer et al. |
| 2007/0179403 A1 | 8/2007 | Heske et al. |
| 2007/0185411 A1 | 8/2007 | Hibner |
| 2007/0213633 A1 | 9/2007 | McClellan |
| 2007/0213634 A1 | 9/2007 | Teague |
| 2007/0260258 A1 | 11/2007 | Sommerich |
| 2007/0299306 A1 | 12/2007 | Parasher et al. |
| 2008/0058637 A1 | 3/2008 | Fischell et al. |
| 2008/0097344 A1 | 4/2008 | McKinnon et al. |
| 2008/0097572 A1 | 4/2008 | Sheldon et al. |
| 2008/0146962 A1 | 6/2008 | Ritchie et al. |
| 2008/0147010 A1 | 6/2008 | Nakajima et al. |
| 2008/0200912 A1 | 8/2008 | Long |
| 2008/0294111 A1 | 11/2008 | Tal et al. |
| 2008/0300462 A1 | 12/2008 | Intoccia et al. |
| 2008/0319341 A1 | 12/2008 | Taylor |
| 2009/0054773 A1* | 2/2009 | Shizuka ............ A61B 18/1492 600/439 |
| 2009/0069679 A1 | 3/2009 | Hibi |
| 2009/0099414 A1 | 4/2009 | Goto et al. |
| 2009/0177114 A1 | 7/2009 | Chin et al. |
| 2009/0182200 A1 | 7/2009 | Golden et al. |
| 2009/0264794 A1 | 10/2009 | Kodama |
| 2009/0312645 A1 | 12/2009 | Weitzner et al. |
| 2010/0081965 A1 | 4/2010 | Mugan et al. |
| 2010/0121218 A1 | 5/2010 | Mugan et al. |
| 2010/0274085 A1 | 10/2010 | Mugan et al. |
| 2011/0054381 A1 | 3/2011 | Van Dam |
| 2011/0071350 A1 | 3/2011 | Van Dam et al. |
| 2011/0137394 A1 | 6/2011 | Lunsford et al. |
| 2011/0152886 A1 | 6/2011 | Sato et al. |
| 2012/0029278 A1 | 2/2012 | Sato et al. |
| 2012/0116248 A1 | 5/2012 | McWeeney et al. |
| 2012/0136426 A1 | 5/2012 | Phan et al. |
| 2012/0157880 A1 | 6/2012 | Haselby et al. |
| 2012/0172896 A1 | 7/2012 | Takahashi et al. |
| 2012/0245486 A1 | 9/2012 | Melchiorr et al. |
| 2012/0253228 A1 | 10/2012 | Schembre et al. |
| 2012/0296257 A1 | 11/2012 | Van Dam et al. |
| 2013/0041286 A1 | 2/2013 | Theobald et al. |
| 2013/0110141 A1 | 5/2013 | Chmura |

(56) References Cited

U.S. PATENT DOCUMENTS

| | | |
|---|---|---|
| 2013/0131547 A1 | 5/2013 | Hardert et al. |
| 2013/0131548 A1 | 5/2013 | McGhie et al. |
| 2013/0253546 A1 | 9/2013 | Sander et al. |
| 2013/0253550 A1 | 9/2013 | Beisel et al. |
| 2013/0310833 A1 | 11/2013 | Brown et al. |
| 2013/0325038 A1 | 12/2013 | Sato |
| 2014/0005478 A1 | 1/2014 | Kennedy, II et al. |
| 2014/0088684 A1 | 3/2014 | Paskar |

FOREIGN PATENT DOCUMENTS

| | | |
|---|---|---|
| EP | 0738501 A1 | 10/1996 |
| EP | 1923003 A1 | 9/2006 |
| EP | 1870051 A1 | 12/2007 |
| EP | 2030574 A2 | 3/2009 |
| EP | 2367481 A2 | 9/2011 |
| EP | 09818508 | 9/2011 |
| JP | 06189965 H | 7/1994 |
| JP | 7116169 H | 5/1995 |
| JP | 8-38482 A | 3/1996 |
| JP | 9-135836 A | 5/1997 |
| JP | 2009122067 A | 5/1997 |
| JP | 200213604 A | 5/2002 |
| JP | 2004181095 | 2/2004 |
| JP | 2005058431 | 3/2005 |
| JP | 2007-513692 A | 5/2007 |
| JP | 20073132538 | 5/2007 |
| JP | 3132538 | 6/2007 |
| WO | 86/005324 A1 | 9/1986 |
| WO | 92/000039 A1 | 1/1992 |
| WO | 9204062 A1 | 3/1992 |
| WO | 00/009178 A1 | 2/2000 |
| WO | 00/33909 A1 | 6/2000 |
| WO | 00/046626 A1 | 8/2000 |
| WO | 2004/066828 A2 | 8/2004 |
| WO | 2004/066829 A2 | 8/2004 |
| WO | 2004/073509 A1 | 9/2004 |
| WO | 2004107988 A2 | 12/2004 |
| WO | 2005/020905 A2 | 3/2005 |
| WO | 2005/081032 A1 | 9/2005 |
| WO | 2005/081033 A1 | 9/2005 |
| WO | 2005096953 A2 | 10/2005 |
| WO | 2005096963 A2 | 10/2005 |
| WO | 2005/112797 A1 | 12/2005 |
| WO | 2005/120345 A2 | 12/2005 |
| WO | 2006/014011 A1 | 2/2006 |
| WO | 2006/028281 A1 | 3/2006 |
| WO | 2006/057443 A1 | 6/2006 |
| WO | 2006/064972 A1 | 6/2006 |
| WO | 2007/021904 A2 | 2/2007 |
| WO | 2007/021904 A3 | 2/2007 |
| WO | 2007/081039 A2 | 7/2007 |
| WO | 2007/081041 A1 | 7/2007 |
| WO | 2007/081050 A1 | 7/2007 |
| WO | 2007/081056 A1 | 7/2007 |
| WO | 2007138674 A1 | 12/2007 |
| WO | 2008/020157 A1 | 2/2008 |
| WO | 2008/020439 A2 | 2/2008 |
| WO | 2008/024684 A2 | 2/2008 |
| WO | 2008/044013 A2 | 4/2008 |
| WO | 2010/039955 A2 | 4/2010 |
| WO | 2010/062895 A2 | 6/2010 |
| WO | 2012112202 A1 | 8/2012 |
| WO | 2013074653 A1 | 5/2013 |

OTHER PUBLICATIONS

Iglesias-Garcia, 2011, Feasibility and Yield of a New EUS Histology Needle: Results from a Multicenter, Pooled, Cohort Study, Gastrointestinal Endoscopy 73(6); 909-915.

Washita, 2013, High Single-Pass Diagnostic Yield of a new 25-Guage Core Biopsy Needle for EUS-Guided FNa biopsy in Solic Pancreatic Lesions, Gastrointestinal Endoscopy 77(6); 909-915.

Kaheleh, 2013, Endoscopic Ultrasonography guided biliary drainage: Summary of consortium meeting, May 7, 2011, Chicago, World Journal of Gastroenterology, 19(9); 1372-1379.

Khashab, 2013, EUS-Guided biliary drainage by using a standardized approach for malignant biliary obstructions: Rendezvous Versus Direct Transluminal techniques, Gastrointestinal Endoscopy; 1-8.

Park, 2011, EUS-guided Biliary Drainage with Transluminal stenting after Failed ERCP: predictors of Adverse Events and long-term Results, Gastrointestinal Endoscopy 74(6); 1276-1284.

Park, 2013, Prospective Evaluation of a Treatment Algorithm with Enhanced Guidewire Manipulation Protocol for EUS-Guided Biliary Drainage after failed ERCP, Gastrointestinal Endoscopy 78(1); 92-101.

Pelaez-Luna, 2008, Interventional EUS Guided Cholangiography. First Description in Mexico of a Novel, Secure and Feasible Technique. A Case Report, Caso Clinico.

Patent Examination Report No. 1 for Patent App. No. 2012339659, dated Sep. 22, 2016, from Australian Government IP Australia.

Notice of Allowance for JP 2014-542405 dated Oct. 6, 2016 from the Japanese Patent Office.

Notice of Reasons for Rejection, dated Jun. 17, 2016, for Japanese Patent App. No. 2014-542405, from Japanese Patent Office.

Canadian Office Action for App. No. 2,744,612 from the Canadian Intellectual Property Office dated Oct. 27, 2016.

Examiner's Report for Canadian App. No. 2,995,281 dated Oct. 19, 2018.

Notice of Reasons for Rejection for JP App No. 2014-236354 dated Dec. 9, 2015.

Examination Report from Canadian Intellectual Property Office for App. No. 2,899,073 dated May 6, 2016.

International Search Report and Written Opinion issued in PCT/US2011/060981, dated Jun. 11, 2012.

International Search Report and Written Opinion issued in PCT/US2009/065705 dated Jul. 7, 2010.

International Search Report for PCT/US2009/059226 dated Apr. 28, 2010.

International Search Report for PCT/US2008/088431 dated Jul. 27, 2009.

International Search Report and Written Opinion issued in PCT/US2012/065049 dated May 2, 2013.

International Search Report and Written Opinion issued in PCT/JP2007053498 dated Mar. 20, 2007.

International Search Report for PCT/US2004/040221 dated Jun. 13, 2005.

International Search Report for PCT/US2012/065049 dated Feb. 22, 2013.

Examination Report for App. No. 09829751.8 dated Feb. 10, 2015.

Office Action for Canadian App. No. 2,739,391 dated Dec. 7, 2015.

Translation of Office Action for Japanese App. No. 2014-236354 dated Dec. 9, 2015.

Examination Report for App. No. 09829751.8 dated Sep. 17, 2015.

Examination Report dated Nov. 25, 2020 Application No. 09818508.5—Covidien LP.

\* cited by examiner

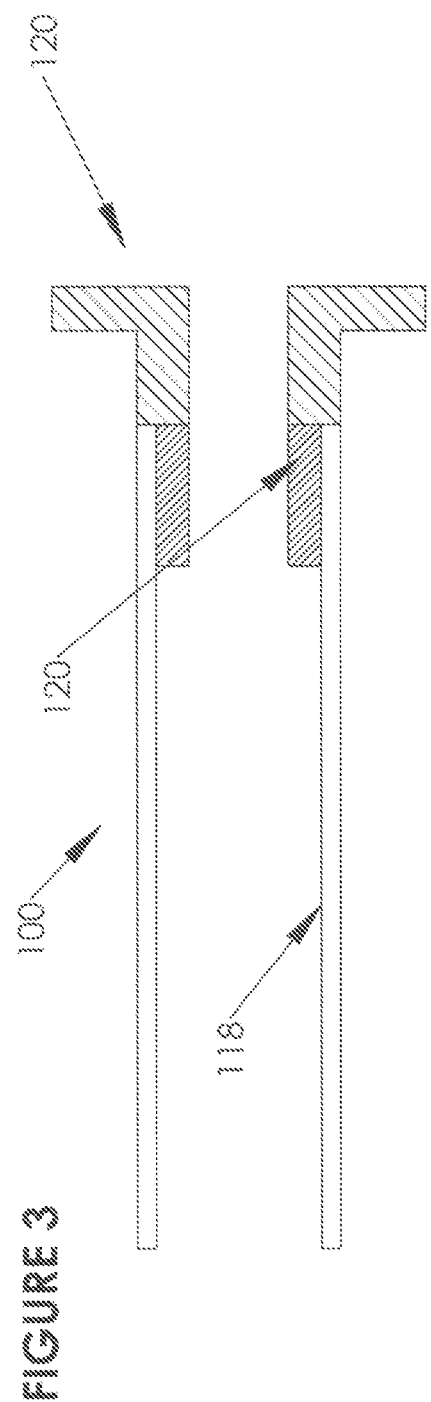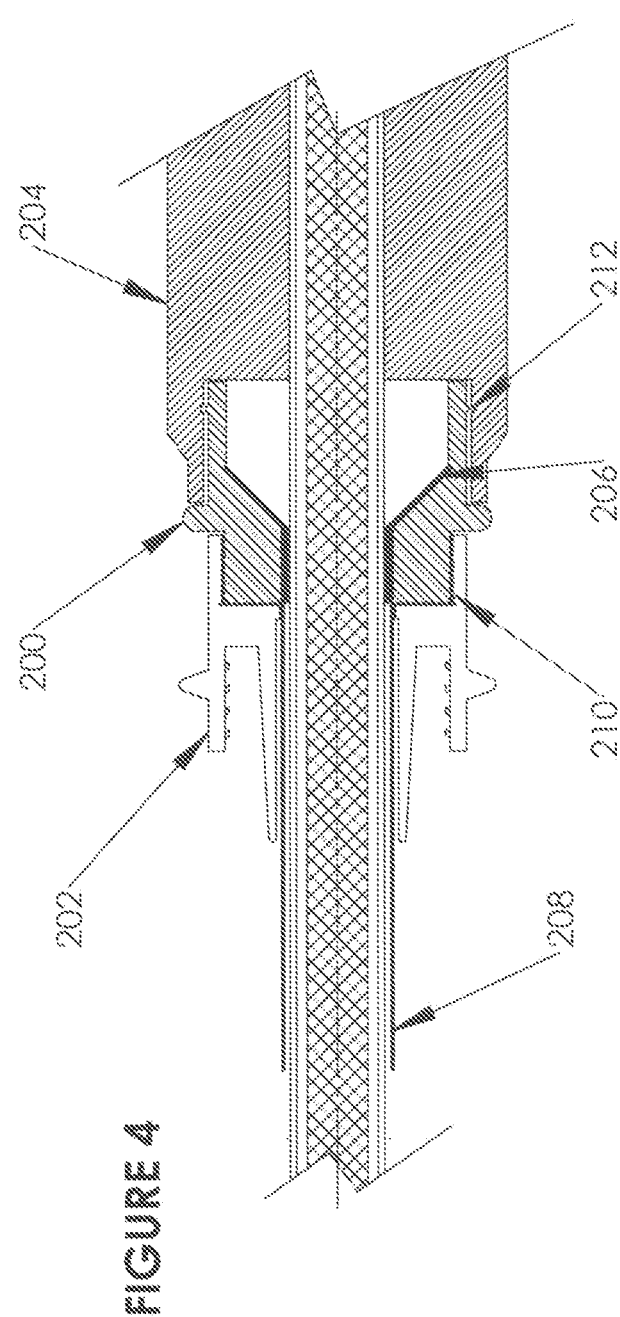

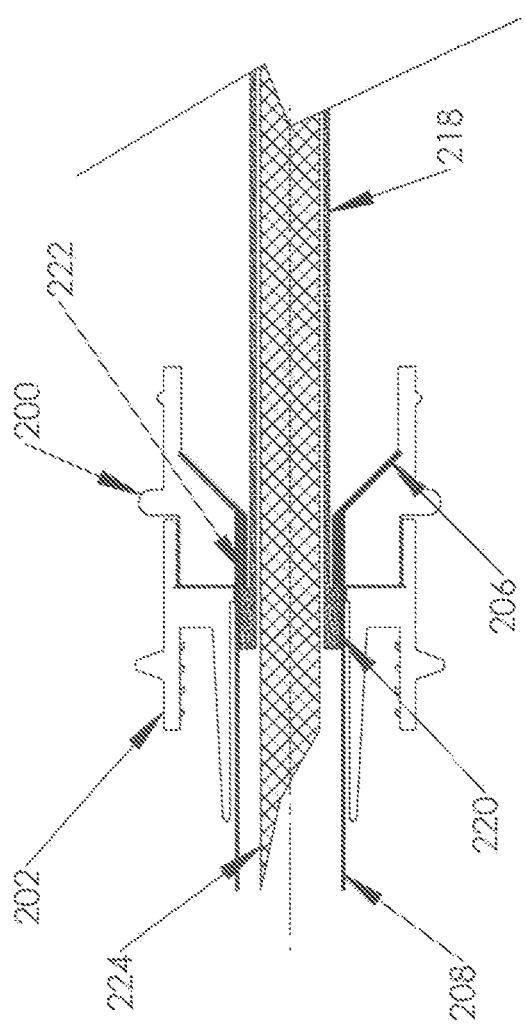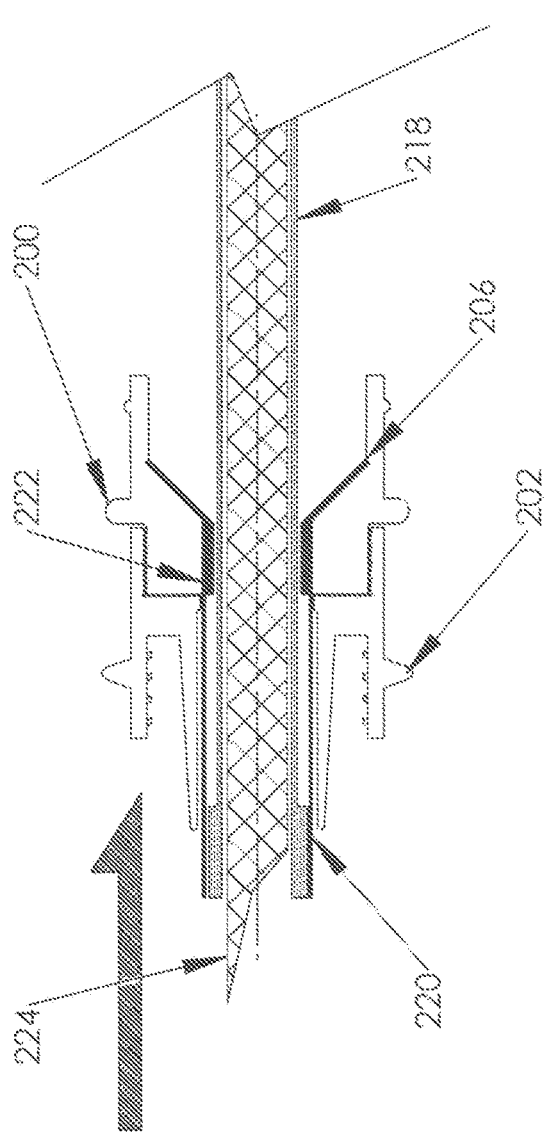

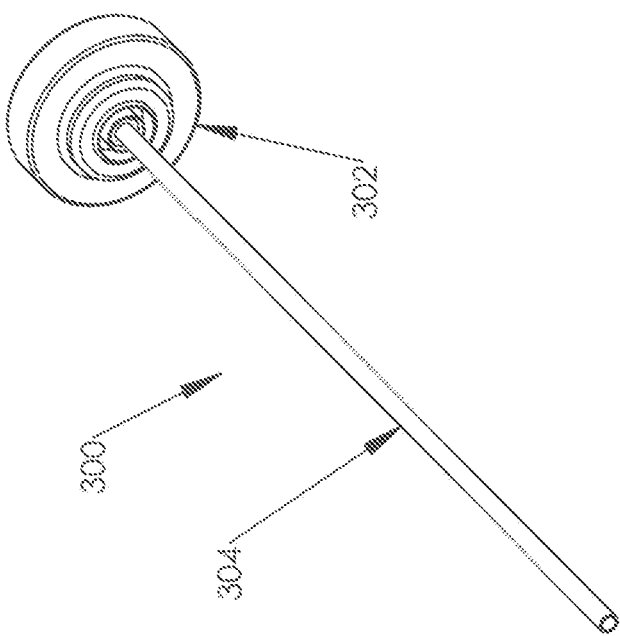

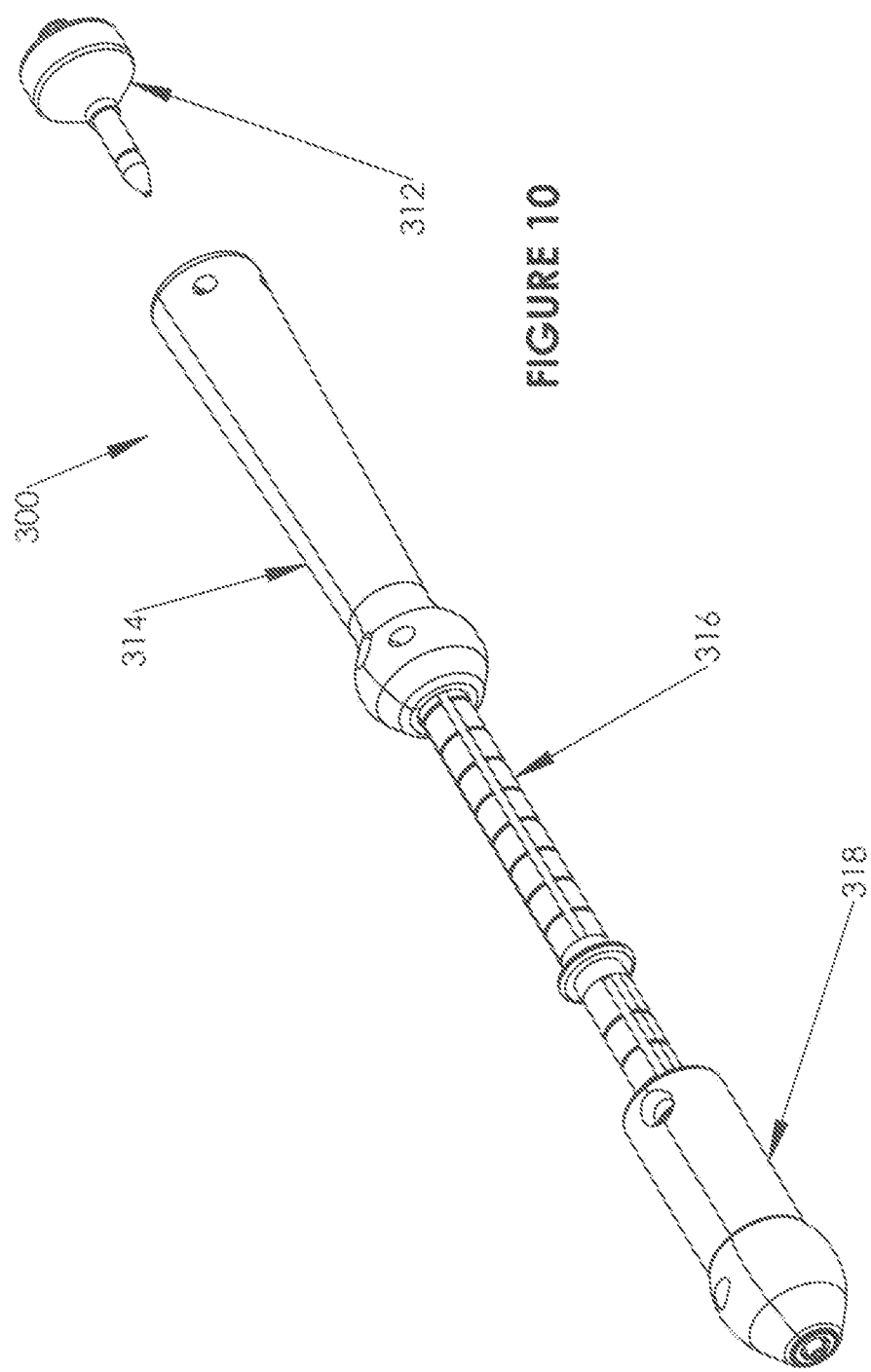

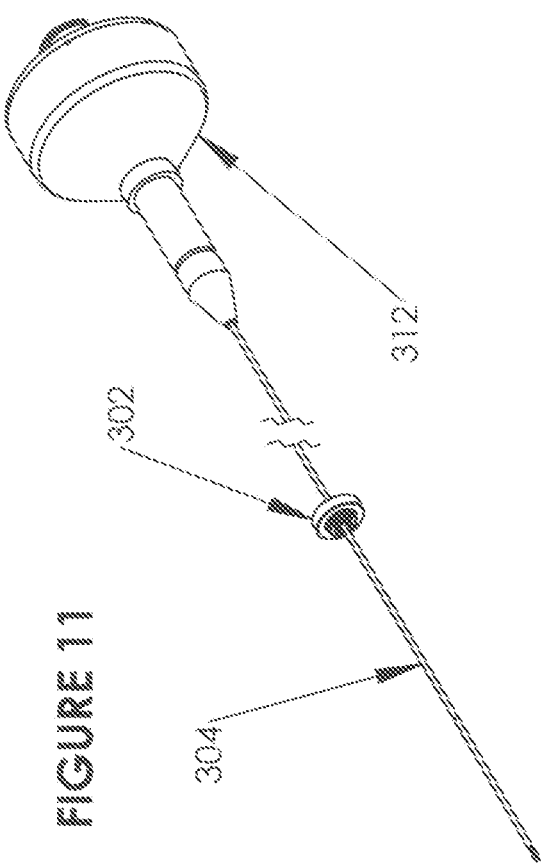

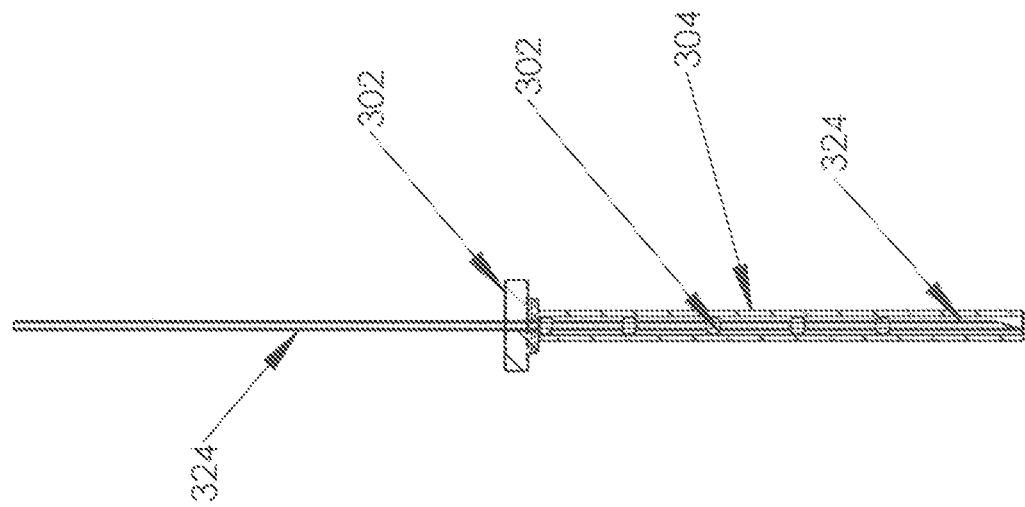
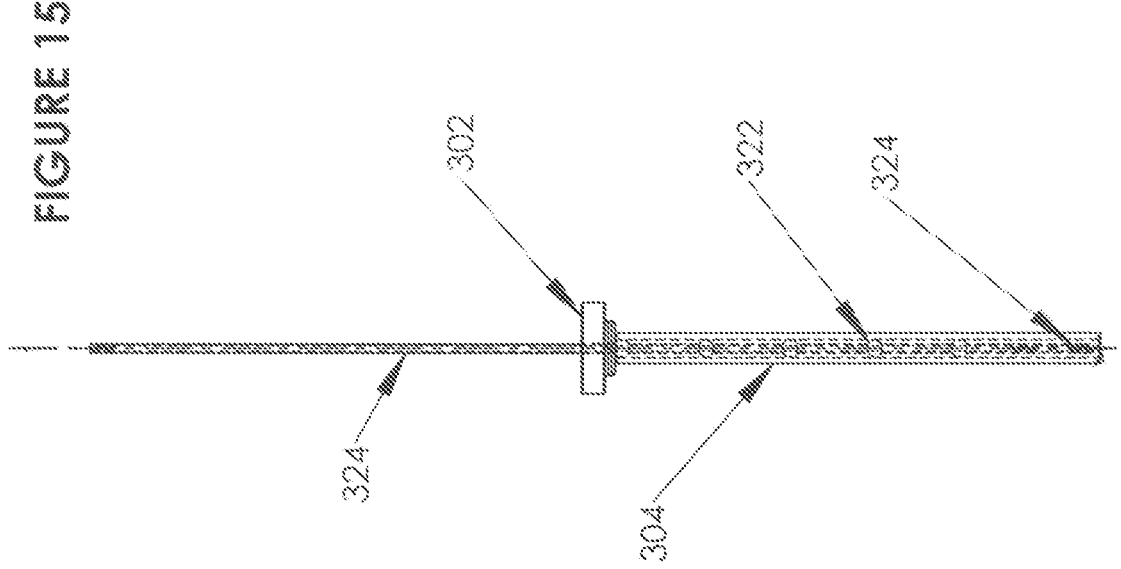

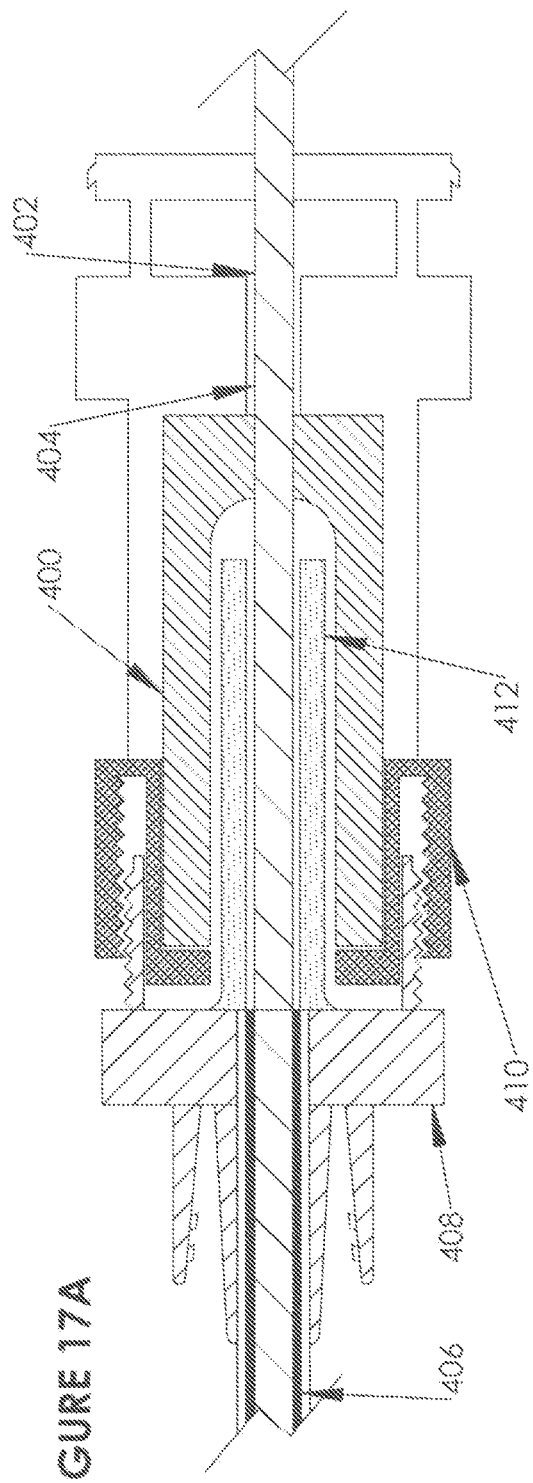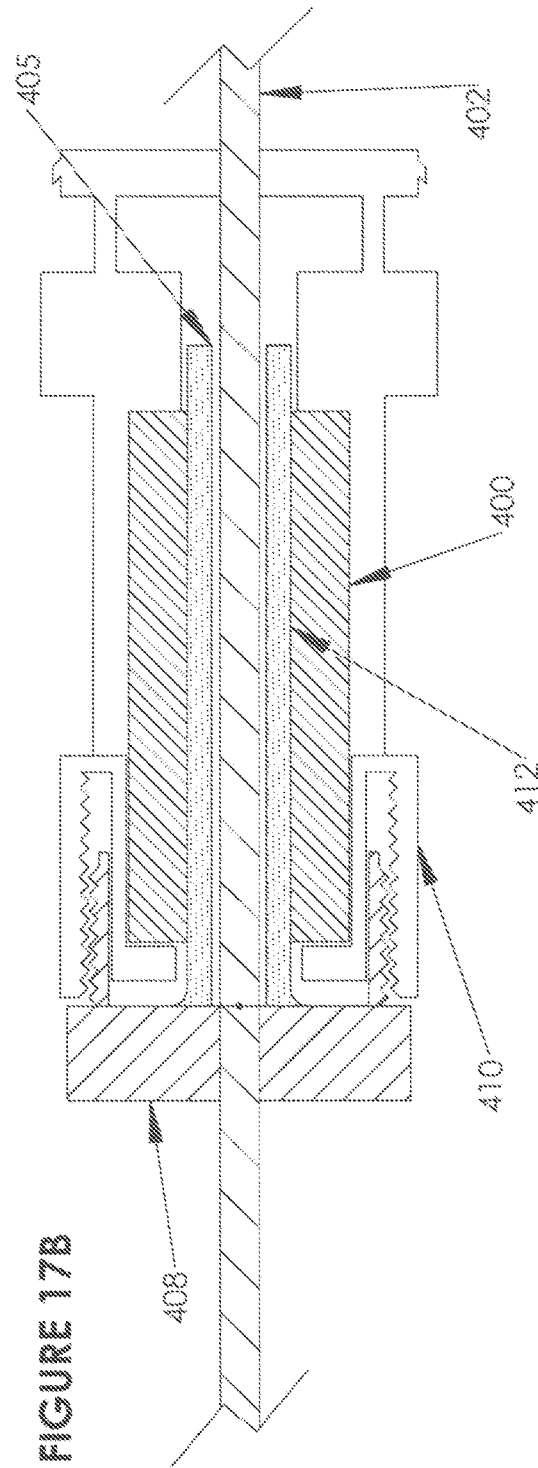

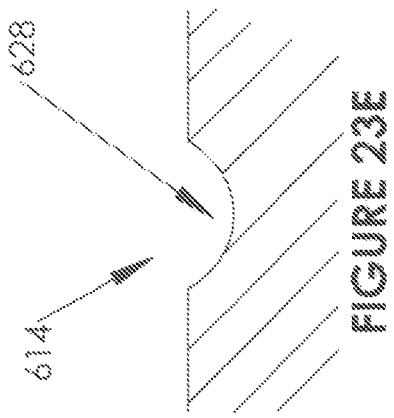
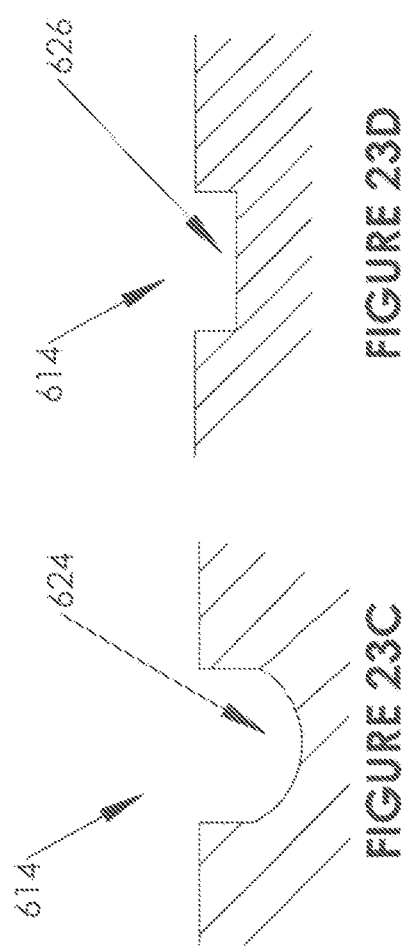
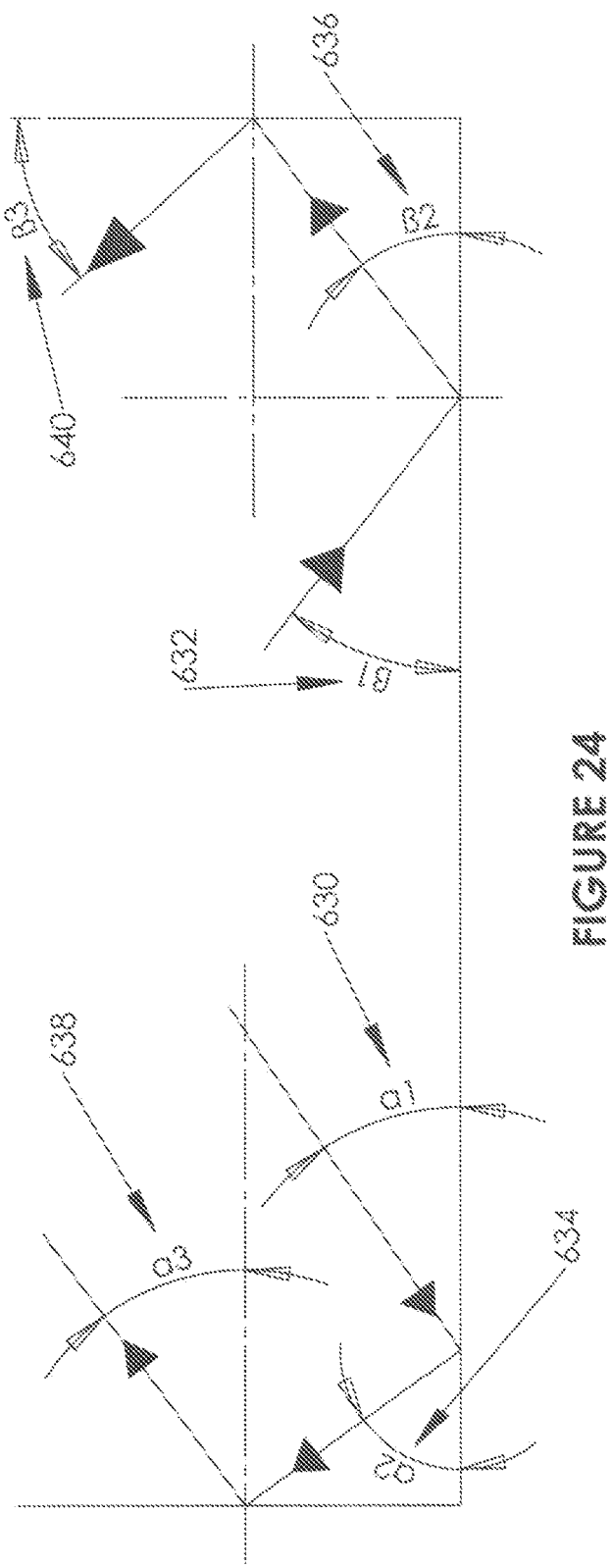

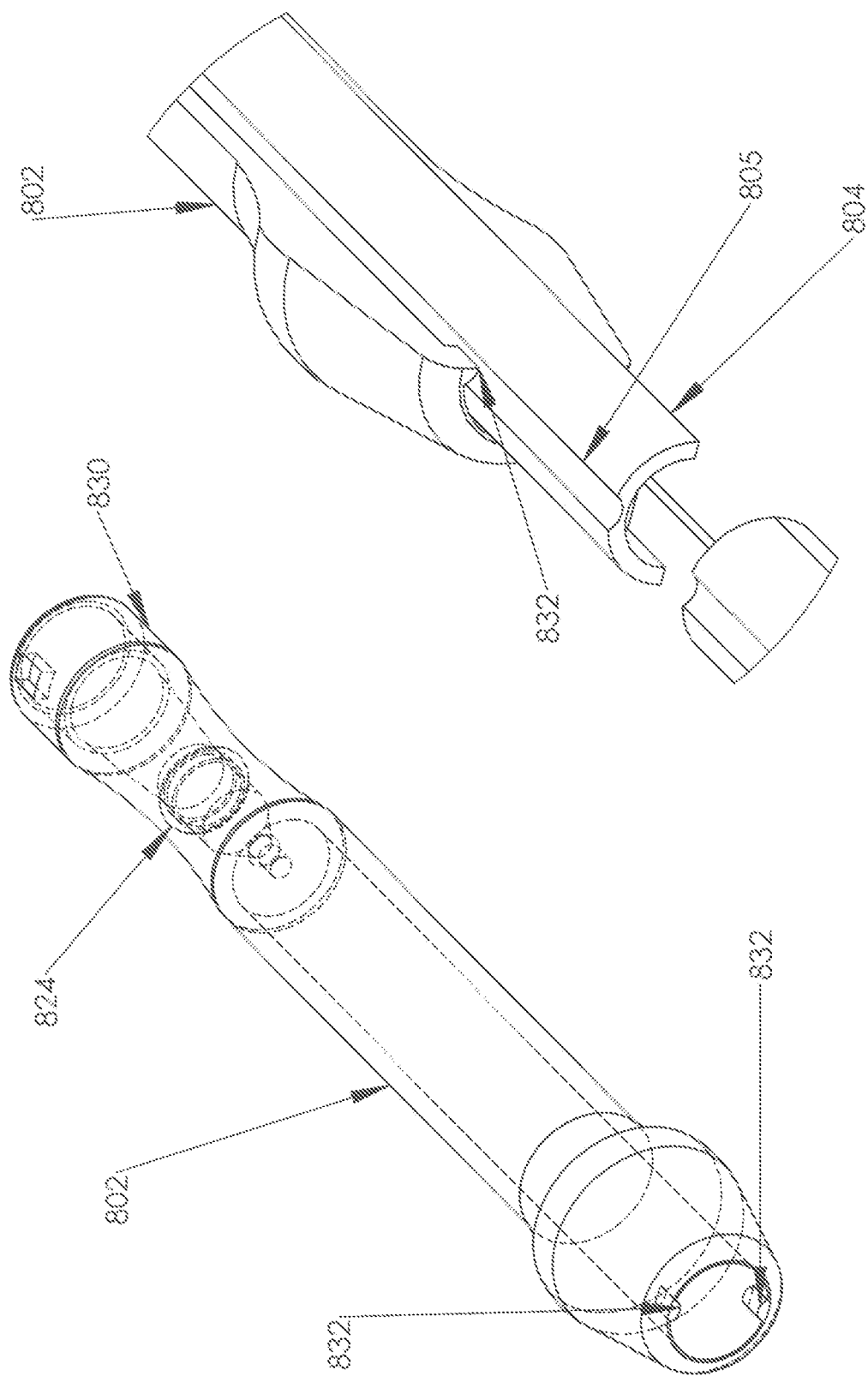

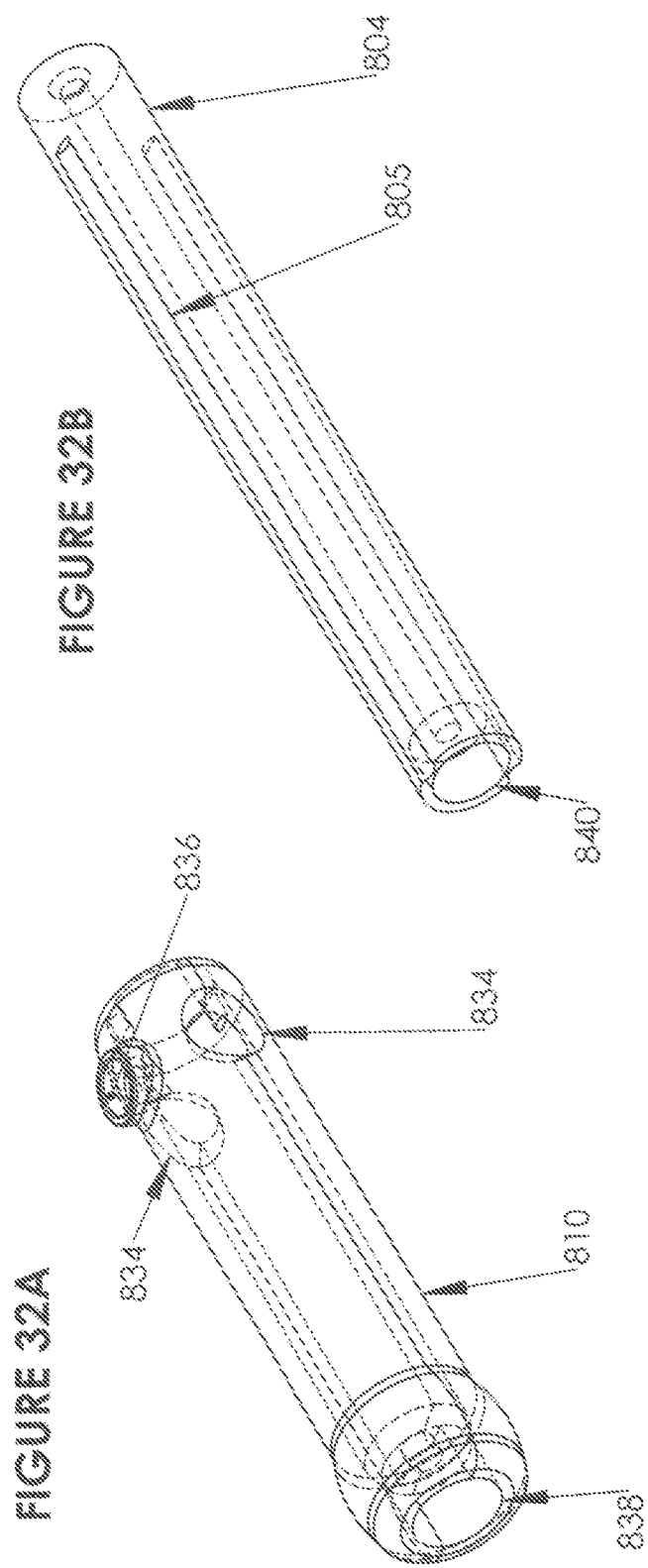
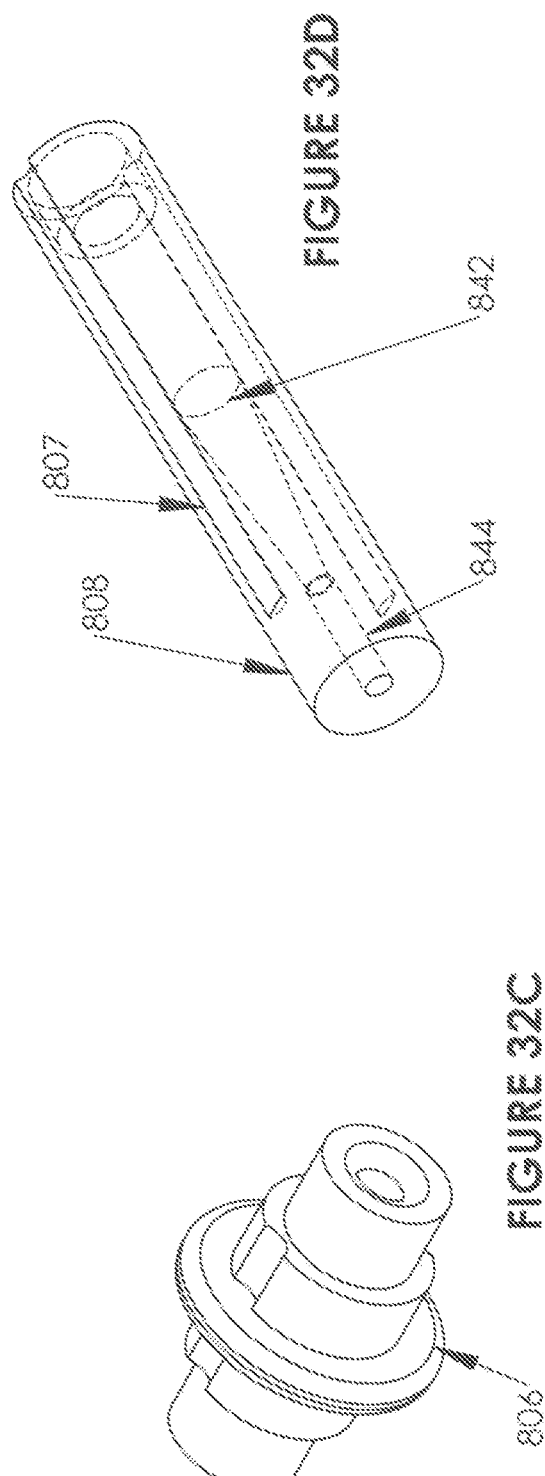
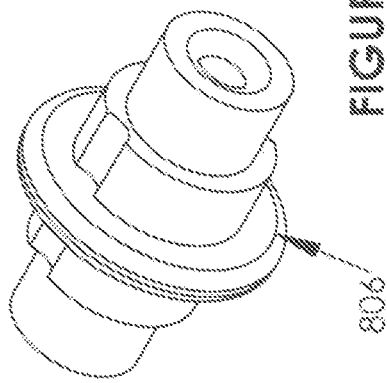

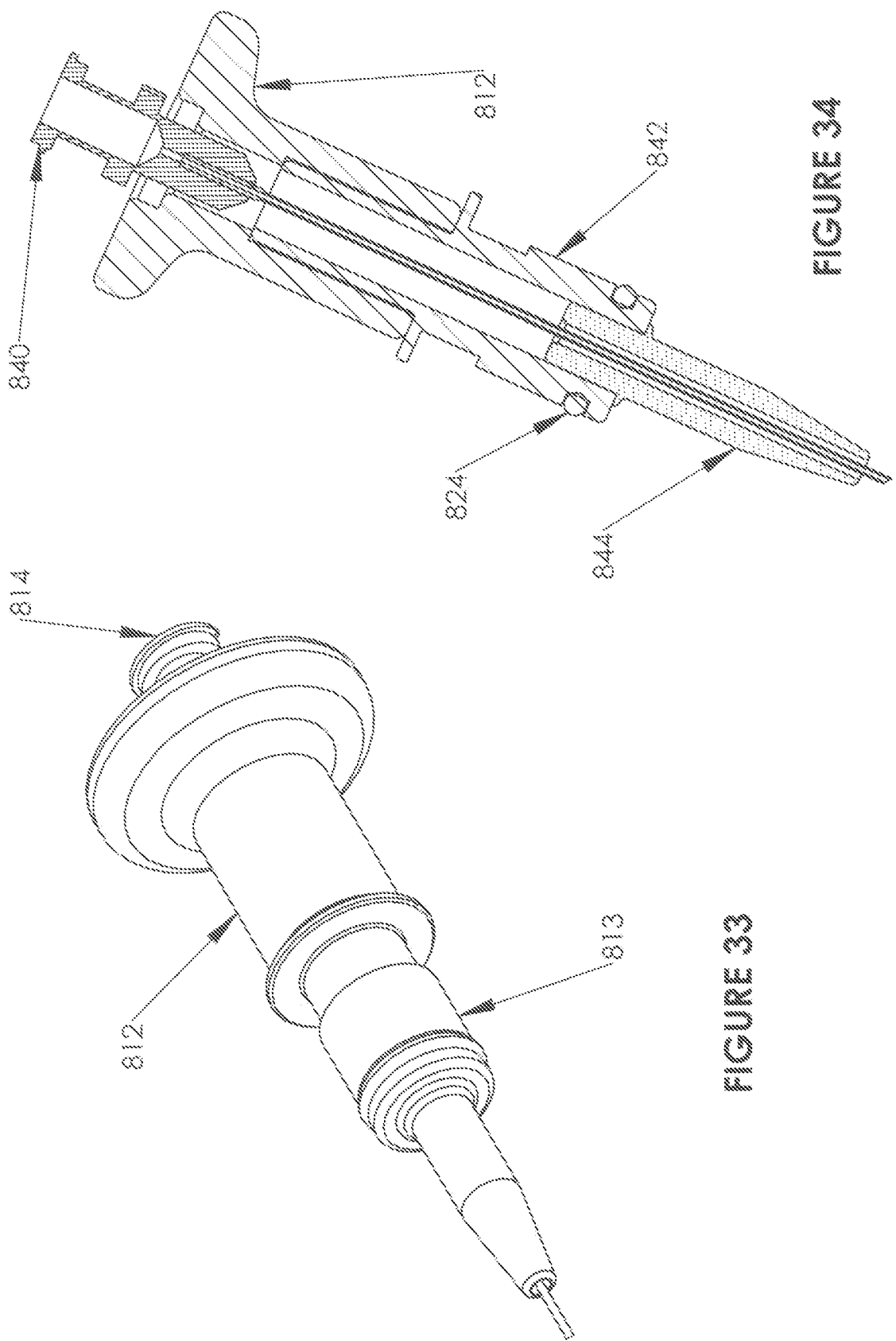

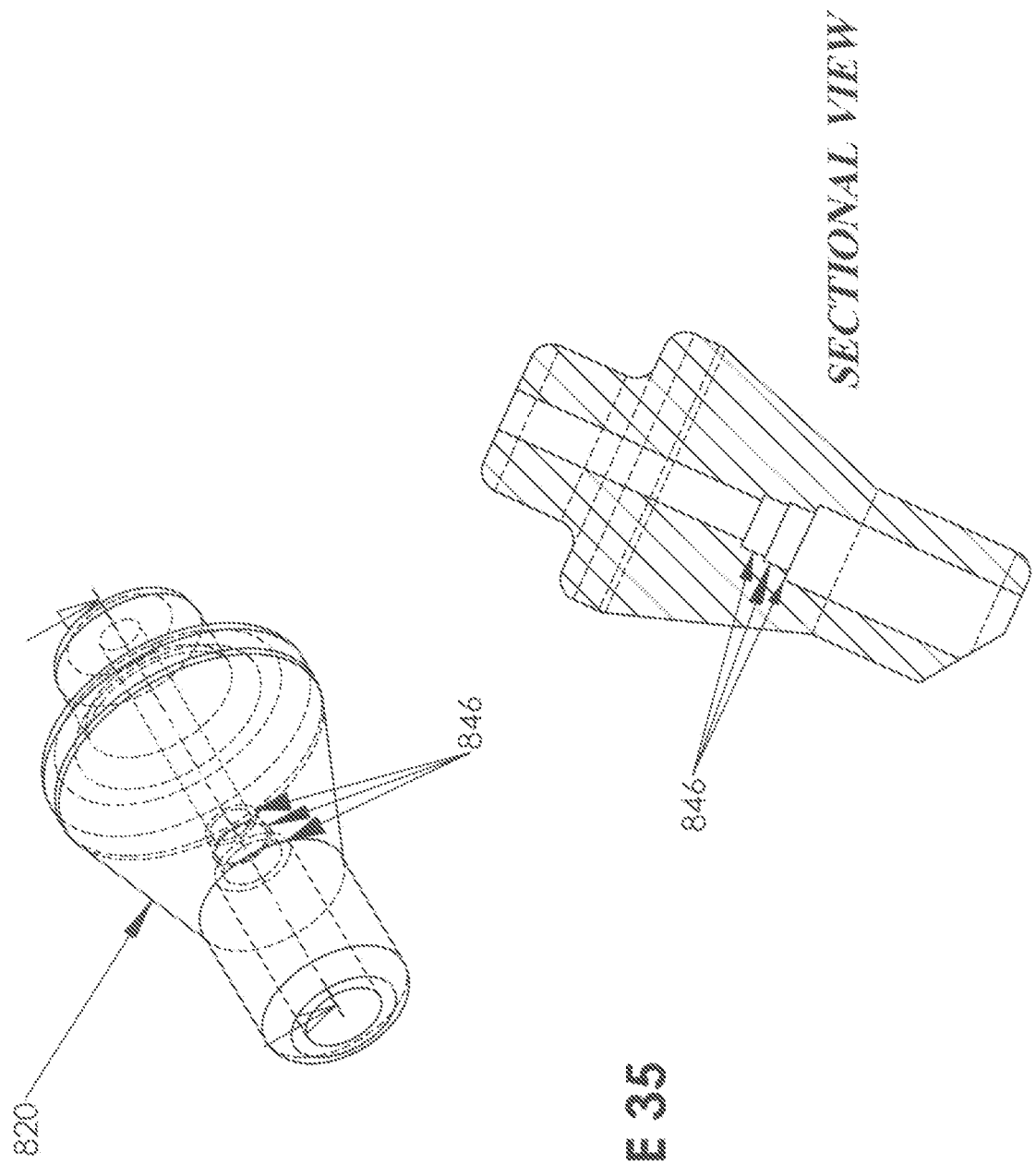

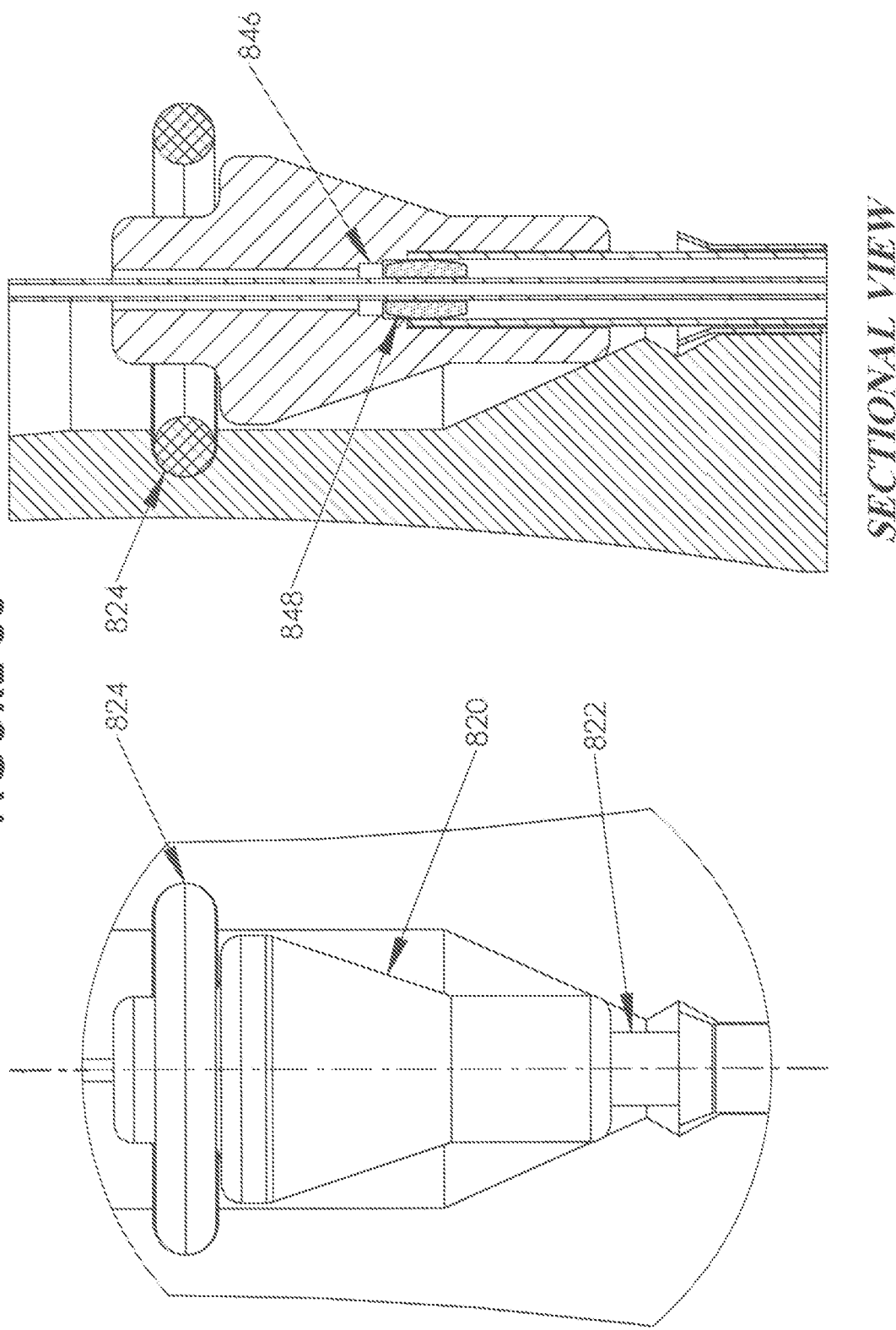

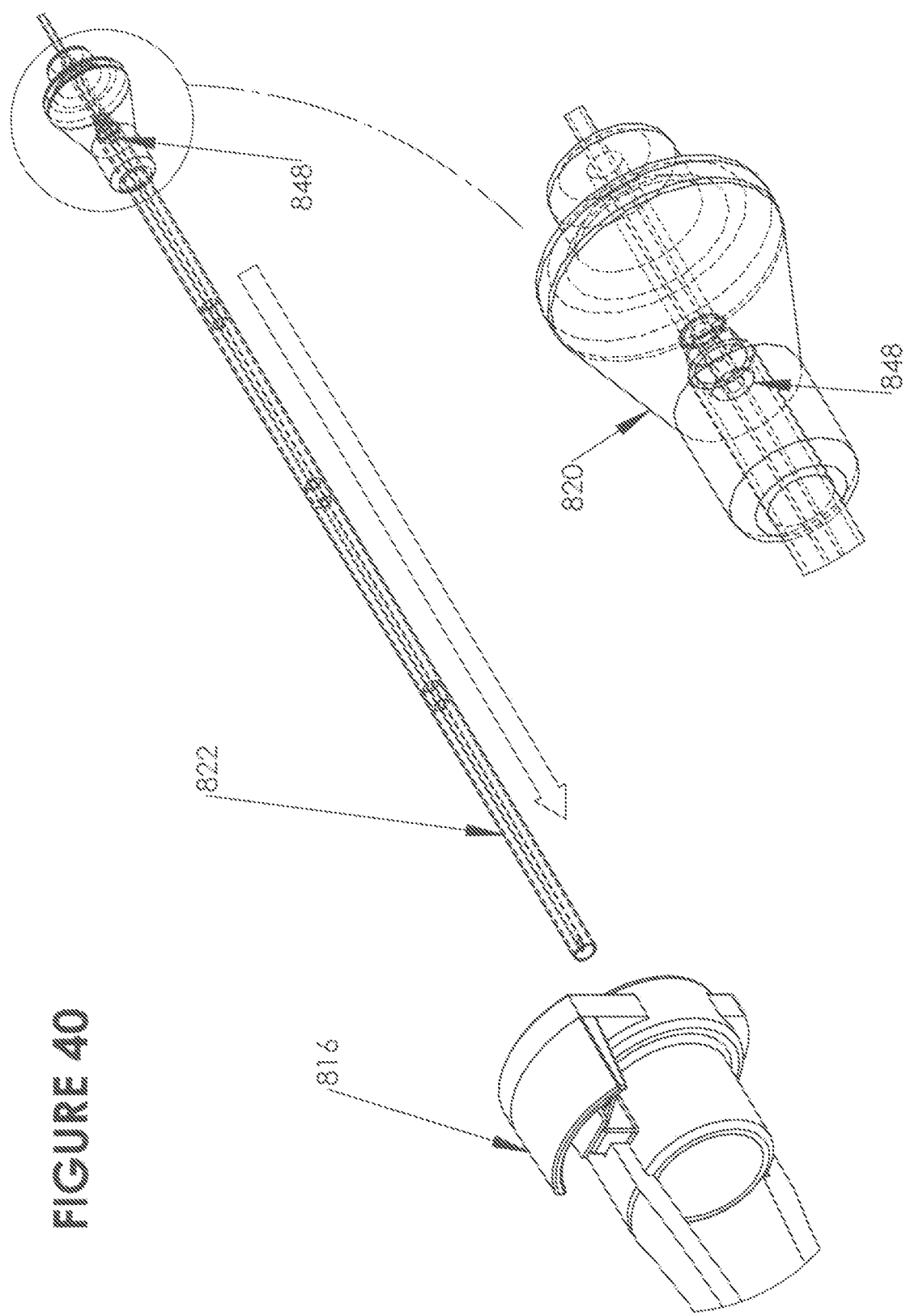

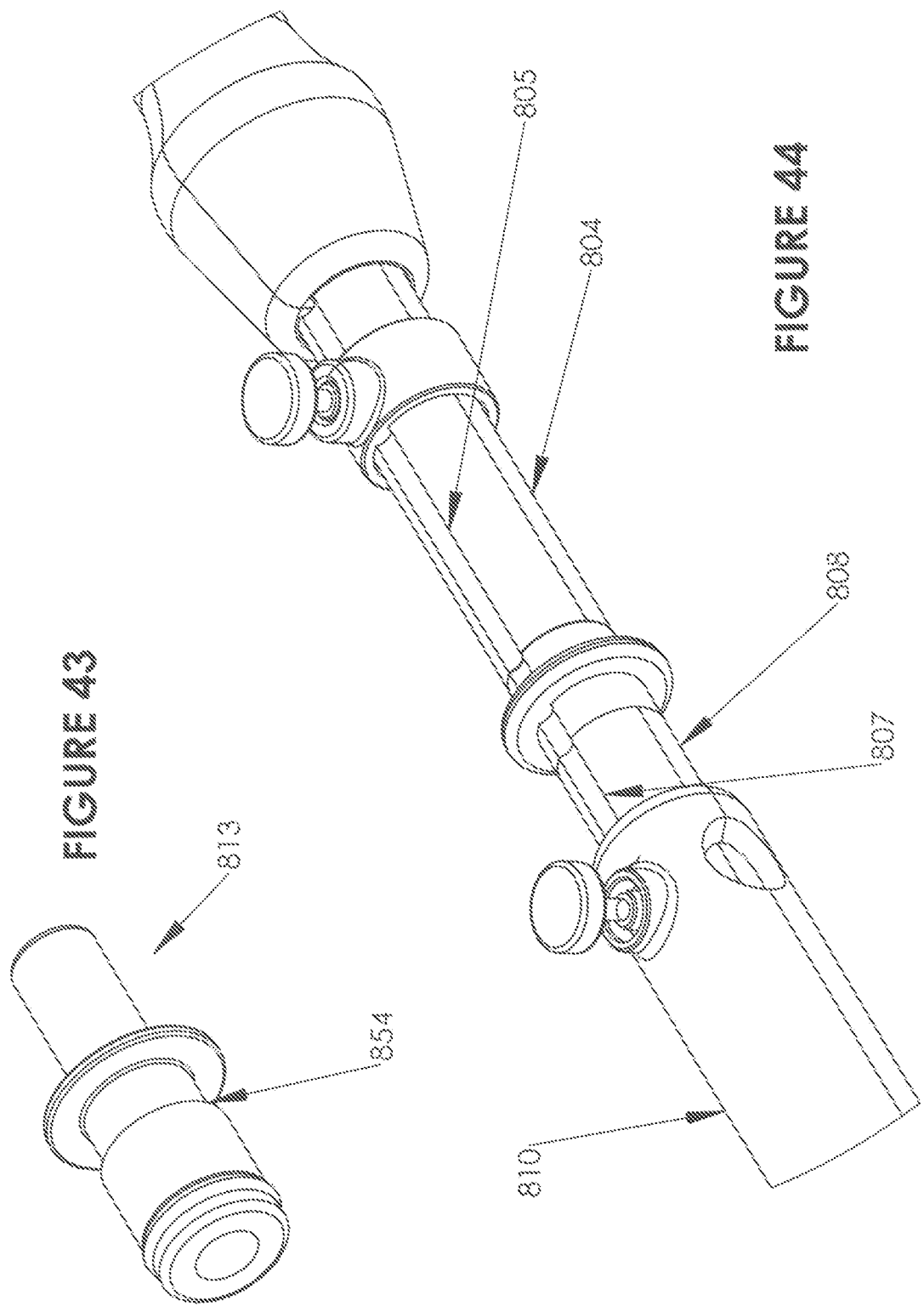

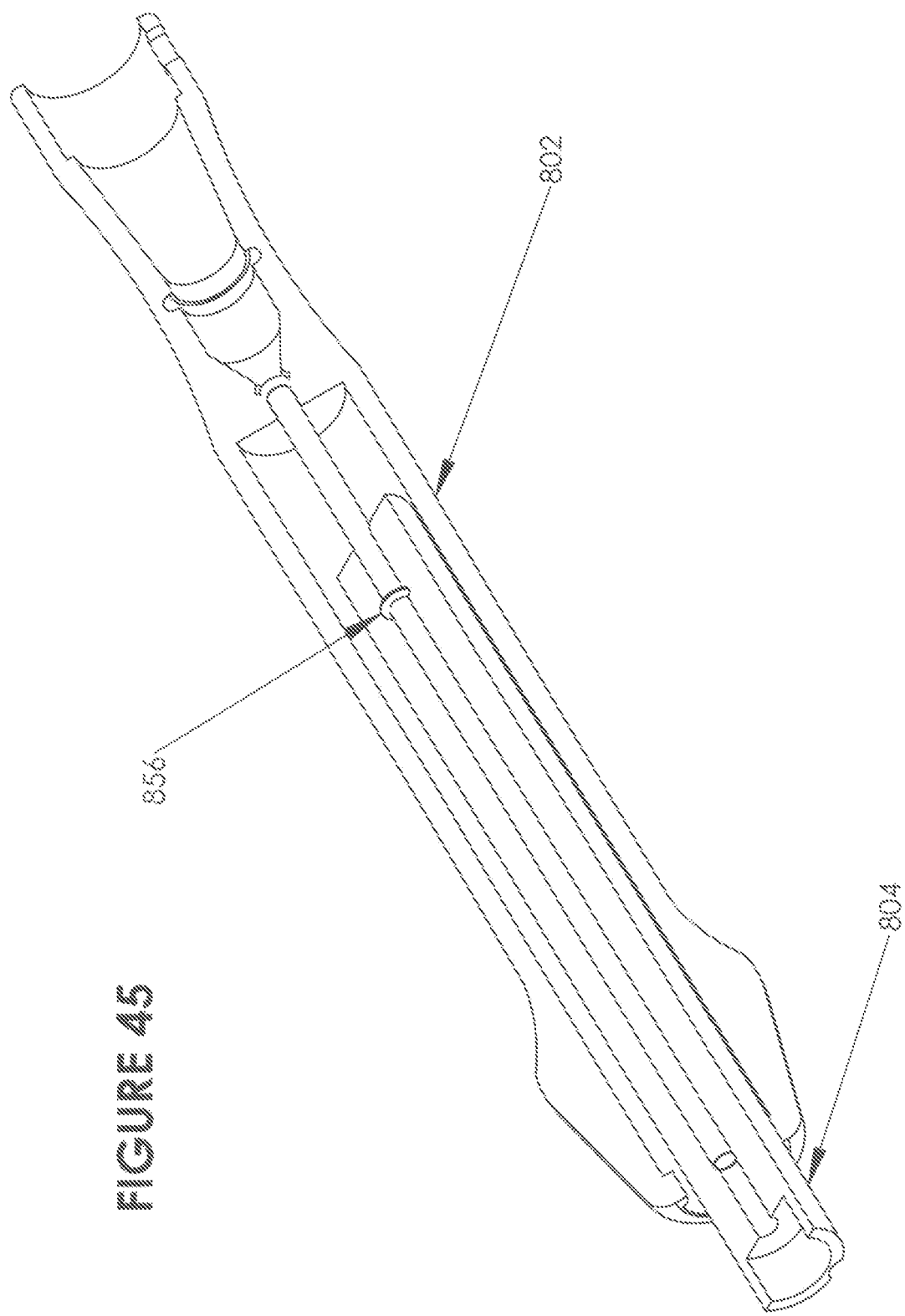

DEVICE FOR NEEDLE BIOPSY WITH INTEGRATED NEEDLE PROTECTION

CROSS-REFERENCE TO RELATED APPLICATIONS

This application is a continuation of prior U.S. patent application Ser. No. 14/630,742, filed Feb. 25, 2015, which is a continuation of U.S. patent application Ser. No. 12/607,636, filed Oct. 28, 2009, now U.S. Pat. No. 8,968,210, which is a Continuation-In-Part application of U.S. patent application Ser. No. 12/243,367, filed on Oct. 1, 2008, now U.S. Pat. No. 9,186,128, and claims the benefit of U.S. Provisional Application No. 61/117,966, filed on Nov. 26, 2008, the entire contents of each are incorporated herein by reference.

BACKGROUND

Endoscopic ultrasound procedures have been used for more than twenty five years within the field of medicine. These procedures allow clinicians to scan, locate and identify individual layers of a patient's gastrointestinal tract to determine the location of individual mucosal and submucosal layers. Once identified, appropriate therapeutic modes of treatment for malignancies and various abnormalities may be determined by a clinician.

An endoscopic ultrasound procedure may consist of several steps. For example, a clinician may sedate a patient and insert a probe via esophagogastroduodenoscopy into the patient's stomach and duodenum. An endoscope may then be passed through the patient's mouth and advanced to the level of the duodenum. From various positions between the esophagus and duodenum, organs or masses outside the gastrointestinal tract may be imaged to determine abnormalities. If any abnormalities are present, the organs or masses can be biopsied through fine needle aspiration. Organs such as the liver, pancreas and adrenal glands are easily biopsied as are any abnormal lymph nodes. A patient's gastrointestinal wall can also be imaged to determine the presence of any abnormalities. For example, abnormal thickness within a patient's gastrointestinal wall may be suggestive of inflammation or malignancy.

The quality of images produced via endoscopic ultrasounds is directly proportional to the level of frequency used. Although a high frequency ultrasound can produce a higher image quality, high frequency ultrasounds do not penetrate organ walls as well as lower frequency ultrasound. As a result, the examination of the nearby organs is not possible.

Mediastinoscopy is a prevailing method for determining the presence of nodal metastases in the mediastinum. Generally performed as an outpatient surgical procedure, mediastinoscopy is associated with a low rate of serious adverse effects and is considered to be highly accurate. Endobronchial ultrasound guided fine needle aspiration biopsy of mediastinal nodes offers a less invasive alternative for histologic sampling of the mediastinal nodes. Endobronchial ultrasound has been widely adopted by pulmonologists and is poised to replace mediastinoscopy in the future. For thoracic surgeons, endobronchial ultrasound can be easily learned and it may be important to do so if their specialty is to maintain the traditional and important role in the diagnosis and staging of thoracic malignancies.

During endobronchial ultrasound, a clinician can perform needle aspiration on lymph nodes using a bronchoscope inserted through the mouth. For an endobronchial ultrasound procedure, an endoscope fitted with an ultrasound processor and a fine-gauge aspiration needle is guided through a patient's trachea. Once appropriately positioned, the needle portion of the fine needle aspiration device is advanced into the lymph node, the sample aspirated, and device is removed from the bronchoscope.

Endoscopic ultrasounds and endoscopic bronchial ultrasounds through fine needle aspiration are presently standard modes of treatment in the field of gastrointestinal endoscopy and bronchoscopy. These procedures traditionally result in high yields of sensitivity and specificity in the management of indications of diseases such as esophageal cancer, pancreatic cancer, liver mass, non-small cell lung cancer, pancreatic mass, endobronchial mass, and intra-abdominal lymph nodes.

An endoscopic ultrasound through fine needle aspiration requires a fine needle aspiration device that is attached to the luer port or working channel of a typical echo-endoscope. Traditional devices utilize a series of push and pull handles to control the axial movement of the catheter shaft of the device and the depth of needle penetration. These device, however, suffer from several drawbacks.

For example, the means of attaching a device to an echo-endoscope is cumbersome. Devices presently utilize male fitting adapters that must be screwed onto a female luer port of an endoscope. In addition, these devices provide sub-optimal ergonomics of use. More specifically, a clinician must actuate a number of handles independently and lock respective handles in position via cap screw arrangement to secure the device. The cumulative actions required by a clinician result in significantly drawn out procedures. Further, needles commonly kink or deform during removal from a device causing numerous delays and failures. Moreover, multiple passes per procedure are required, which prolong the procedure and result in a clinician needing to reconfirm the location of a needle relative to a desired aspiration site with each new pass.

Another drawback involving a typical echoendoscope concerns the lack of needle safe preventative design features which protect the clinician from inadvertent needle penetration and the transfer of blood-borne pathogens from a patient to attending medical staff. In the case of currently available fine needle aspiration medical devices for both endoscopic ultrasound and endo-bronchial ultrasound, once a sample has been aspirated from the desired anatomical location, the fine needle aspiration catheter is removed from the echo-endoscope and handed to the clinician for sample extraction and preparation. The clinician is instructed to "re-sheath" the needle (i.e. retract the needle into the catheter sheath) prior to detachment from the echo-endoscope. However, in many instances, this does not occur. As such, the needle sharp of the device is exposed during removal and transfer of the fine needle aspiration device among medical staff in the endoscopic ultrasound and endo-bronchial ultrasound suite with increased risk of "needle sticking" and blood borne pathogen contamination and exposure to same.

Additionally, needles are commonly used in medical procedures, with biopsy being a primary field of use for such devices. In the case of Endoscopic Ultrasound (EUS) and Endo-bronchial Ultrasound (EBUS), the efficiency of the ultrasonic procedure relies on the ability to direct the needle component to the desired site of sample acquisition. Smooth cylindrical surfaces of needles are unfortunately very difficult to image using ultrasonography due to the specular (mirror-like) surface finish of the needle in the untreated state. To address this problem, various techniques have been developed to enhance the echogenicty or ultrasonic visibility of needles. Various techniques (sandblasting, surface etching and coating of surfaces) have been used to "roughen" the surface of a needle component with limited success. This surface roughening results in a scattering of rays from the ultrasound. However, some of the drawbacks of the aforementioned techniques concern the angle of incidence (sound waves from the ultrasonic transducer) and the angle of reflection (sound waves reflected back to the transducer array). It is important that the method and design of surface finish and surface deformation imparted to the needle of the biopsy device maximize the percentage of waves reflective which can be picked up by the ultrasonic array.

Therefore, a need exists for improved devices for use in endoscopic ultrasound procedures.

SUMMARY

According to an aspect of the present disclosure, a device for needle biopsy is presented. The needle biopsy device is comprised of a handle member, a proximal handle member, a distal handle member, a sheath lumen, a needle housing member, a needle, a stylet, and ergonomic design features, including a conical grip, to enhance the maneuverability and operation of the device.

According to another aspect of the present disclosure, a device for needle biopsy is presented. The needle biopsy device is comprised of a handle member, a proximal handle member, a distal handle member, a sheath lumen, a needle housing member, a needle, a needle protection adaptor, and a needle protection member.

According to another aspect of the present disclosure, a device for needle biopsy is presented. The needle biopsy device is comprised of a handle member, including an engageable member, a proximal handle member, a distal handle member, a sheath lumen, a needle housing member, a land ring, a strain relief member, a needle containing a plurality of protrusions disposed thereon, a needle protection member, a needle protection hub, and a needle protection shaft.

According to yet another aspect of the present disclosure, a device for needle biopsy is presented. The needle biopsy device is comprised of a handle member, a proximal handle member, a distal handle member, a sheath lumen, a needle housing member, and a needle including a plurality of depressions to enhance echogenicity and ultrasonic visibility.

According to yet another aspect of the present disclosure, a device for needle biopsy is presented. The needle biopsy device is comprised of a handle member, a proximal handle member, a distal handle member, a sheath lumen, a needle housing member, and, a needle including a plurality of protrusions disposed thereon and a joint permitting detachment of the distal portion of the needle.

According to another aspect of the present disclosure, a device for needle biopsy is presented. The needle biopsy device is comprised of a handle member, a proximal handle member that is configured for slideable engagement and includes at least one guide-rail along its longitudinal axis to engage at least one recessed groove to control slideable movement, a distal handle member that is configured for slideable engagement and includes at least one guide-rail along the longitudinal axis to engage at least one recessed groove to control slideable movement, a sheath lumen, a needle housing member, and a needle.

According to another aspect of the present disclosure, a device for needle biopsy is presented. The needle biopsy device is comprised of a handle member, a proximal handle member, a distal handle member, a sheath lumen, a needle housing member, a needle, and a needle lock member.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

FIG. 3 is a cross-sectional view of another embodiment of a needle protection member, according to the present disclosure;

FIG. 4 is a perspective view of an embodiment of a needle protection adapter, according to the present disclosure;

FIG. 7 is a cross-sectional view of an embodiment of a needle protection member, according to the present disclosure;

FIG. 8 is a cross-sectional view of an embodiment of a needle protection member, according to the present disclosure;

FIG. 9 is a perspective view of an embodiment of a needle protection member, according to the present disclosure;

FIG. 10 is a perspective view of an embodiment of a needle biopsy device, according to the present disclosure;

FIG. 11 is a perspective view of an embodiment of a needle protection member, according to the present disclosure;

FIG. 15 is a perspective view of an embodiment of a needle protection member, according to the present disclosure;

FIG. 16 is a perspective view of an embodiment of a needle protection member, according to the present disclosure;

FIG. 17A is a perspective view of an embodiment of a needle lock member, according to the present disclosure;

FIG. 17B is a perspective view of an embodiment of a needle lock member, according to the present disclosure;

FIG. 23C is a perspective view of an embodiment of a needle, according to the present disclosure;

FIG. 23D is a perspective view of an embodiment of a needle, according to the present disclosure;

FIG. 23E is a perspective view of an embodiment of a needle, according to the present disclosure;

FIG. 24 is a flow diagram of ultra-sound waves, according to the present disclosure;

FIG. 30 is a perspective view of an embodiment of a needle biopsy device, according to the present disclosure;

FIG. 31 is a perspective view of an embodiment of a needle biopsy device, according to the present disclosure;

FIG. 32A is a perspective view of an embodiment of a needle biopsy device, according to the present disclosure;

FIG. 32B is a perspective view of an embodiment of a needle biopsy device, according to the present disclosure;

FIG. 32C is a perspective view of an embodiment of a needle biopsy device, according to the present disclosure;

FIG. 32D is a perspective view of an embodiment of a needle biopsy device, according to the present disclosure;

FIG. 33 is a perspective view of an embodiment of a needle biopsy device, according to the present disclosure;

FIG. 34 is a perspective view of an embodiment of a needle biopsy device, according to the present disclosure;

FIG. 35 is a perspective view of an embodiment of a needle biopsy device, according to the present disclosure;

FIG. 36 is a perspective view of an embodiment of a needle biopsy device, according to the present disclosure;

FIG. 40 is a perspective view of an embodiment of a needle biopsy device, according to the present disclosure;

FIG. 43 is a perspective view of an embodiment of a needle biopsy device, according to the present disclosure;

FIG. 44 is a perspective view of an embodiment of a needle biopsy device, according to the present disclosure; and FIG. 45 is a perspective view of an embodiment of a needle biopsy device, according to the present disclosure.

DETAILED DESCRIPTION

The exemplary embodiments of the present disclosure are discussed in terms of needle biopsy devices for collecting tissue, fluid, and cell samples from a patient in conjunction with an endoscopic ultrasound or endoscopic bronchial ultrasound. It is contemplated that various embodiments of needle biopsy devices may include a modular design. For example, the needle biopsy device may include a needle housing member that detaches from the proximal handle member of the device for each individual pass or aspirated sample taken by a clinician at the site of lesion or abnormality. In addition, potential design embodiments are disclosed herewith that facilitate needle sharp safety and protection thereof, when combined with devices that incorporate an integrated catheter drive, needle advancement, needle retraction mechanism, and needle in the same device.

It is envisioned that the present disclosure finds application to a wide variety of biopsy devices for the collection of samples from a patient. It is also envisioned that the present disclosure may be employed for collection of body fluids including those employed during procedures relating to phlebotomy, digestive, intestinal, urinary, and veterinary. It is contemplated that the present disclosure may be utilized with other needle biopsy applications including, but not limited to, fluid collection, catheters, catheter introducers, spinal and epidural biopsy, aphaeresis, and dialysis.

In the discussion that follows, the term "proximal" refers to a portion of a structure that is closer to a clinician, and the term "distal" refers to a portion that is further from the clinician. According to the present disclosure, the term "clinician" refers to an individual performing sample collection, installing or removing a needle from a needle biopsy device, and may include support personnel. Reference will now be made in detail to exemplary embodiments of the disclosure, which are illustrated in the accompanying figures.

Figure 1:
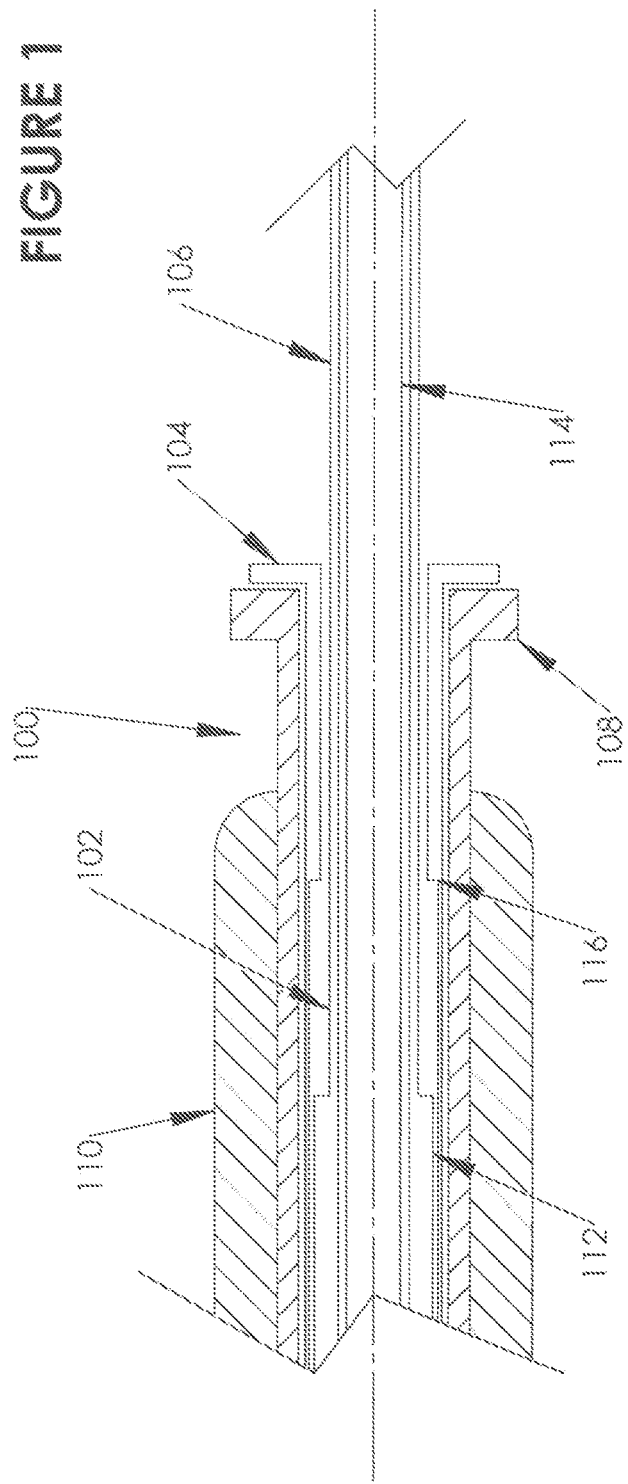
FIG. 1 is a cross-sectional view of an embodiment of a needle protection member, according to the present disclosure.
Figure 2:
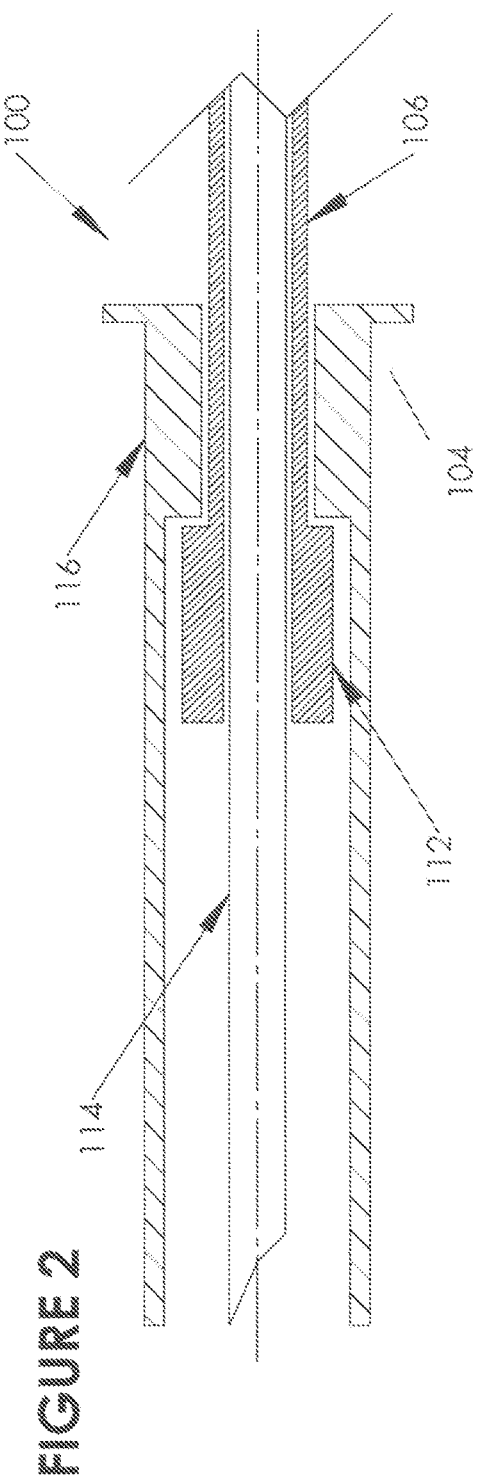
FIG. 2 is a cross-sectional view of an embodiment of a needle protection member, according to the present disclosure.

Referring now to FIGS. 1 and 2, cross-sectional views of embodiments of a needle protection member 100 utilized with a luer port 108 of an echo-endoscope 110 is presented. Needle protection member 100 is comprised of a needle protection shaft 102 and a needle protection hub 104. The length of needle protection shaft 102 may be, for example, between four (4) to twenty (20) centimeters in order to protect a clinician from inadvertent piercing by a needle 114. Needle protection hub 104 is located at the proximal portion of needle protection member 100. In an embodiment, needle protection hub 104 is comprised of at least one engagable member 116. At least one engagable member may be, for example, a flange.

Needle protection member 100 may be manufactured from a compressible material such as polyurethane, polyetheramide or copolymers thereof, silicone, neoprene rubber, polyvinylchloride or copolymers thereof, polyethylene or derivatives thereof or other commercially available, low durometer polymers materials. The material of manufacture shall provide a compressible fit between needle protection member 100 and luer port 108 at the proximal end of echo-endoscope 110.

Needle protection member 100 resides over a sheath lumen 106. Needle protection member 100 is free to move over sheath lumen 106 at the proximal end of echo-endoscope 110. In an embodiment, needle protection member 100 is secured in position against luer port 108 as a clinician attaches a needle biopsy device (not shown in Figure) to echo-endoscope 110 by means screwing the luer lock adaptor of the needle biopsy device (not shown in Figure) onto luer port 108. Needle protection member 100 is held in position once the luer lock adaptor of the needle biopsy device is tightened onto luer port 108.

Sheath lumen 106 may consist of a polymer extruded component that is rigid in nature. Sheath lumen 106 may be comprised of, for example, thermoplastic materials. The thermoplastic materials may be, but are not limited to, polyurethane, polyamide and derivatives thereof, ether block amide copolymers, polyimide, polyethylene and derivates thereof, and polytetrafluoroethylene. Sheath lumen 106 may also be comprised of a helically braided configuration of outer thermoplastic materials with a lubricious inner core.

Sheath lumen 106 incorporates at least one engagable member 112 that is complimentary to at least one engagable member 116 of needle protection member 100. Engagable member 112 represents a transition in the outer diameter of the distal portion of sheath lumen 106. The outer diameter of engagable member 112 may be, for example, of the order of 0.002" to 0.050" in outer diameter as well as of the order of 0.005"-0.020".

In an embodiment of the present disclosure, a clinician may take measures to protect from inadvertent needle piercing by retracting sheath lumen 106 in a proximal direction. During the step of retraction, engagable member 112 communicates with engagable member 116. As engagable member 112 communicates with engagable member 116, needle protection member 100 disengages from luer port 108 and covers the distal portion of needle 114. Needle protection member 100 covers needle 114 even when needle 112 is at its maximum length of extension from the distal end of catheter sheath 106.

Referring to FIG. 3, a cross-sectional view of another embodiment of needle protection member 100 is presented. Needle protection member 100 consists of a compressible and deformable element 104 at its proximal end to provide for compression when inserted inside a luer port of an echo-endoscope (not shown in Figure). Needle protection member 100 further includes a needle protection shaft 118 and a land insert 120.

Needle protection shaft 118 may be manufactured from a rigid polymer such as polyurethane, polyamide and derivatives thereof, ether block amide copolymers, polyimide, polyethylene and derivates thereof, polytetrafluoroethylene, or metal based elements such as stainless steel or derivatives thereof. In another embodiment, needle protection shaft 118 is manufactured from a stainless steel type material to provide a clinician with the ability to straighten a needle for re-insertion in the event that the needle becomes damaged as a result of continuous usage and passage during the acquisition of multiple samples. Needle protection shaft 118 may be over-molded to combine the requirements of compressibility with the rigidity of land insert 120.

Referring to FIG. 4, a perspective view of a needle protection adapter 200 is presented. Needle protection adaptor 200 is attached proximally to a luer adapter 202 and distally to a needle biopsy device 204. Needle protection adaptor 200 is comprised of a needle protection member 206, a needle protection shaft 208, an adapter member 210, and at least one engagable member 212.

Needle protection member 206 may be over-molded from thermoplastic material such as acrylonitrile butadiene styrene, polystyrene and derivatives thereof, polyetherkeytone, polyamide, polyethersulfone, polyurethane, ether block amide copolymers, polyacetal, polycarbonate and derivatives thereof. In an embodiment, needle protection shaft 208 consists of a stainless steel hypo-tube to provide rigidity and the ability to straighten a needle in the event that the needle may have become kinked during successive passages.

Adapter member 210 and engagable member 212 facilitate the engagement between luer adapter 202, needle protection adapter 200, and needle biopsy device 204. Adapter member 210 and engagable member 212 may be, for example, a screw thread or a snap-fit type of arrangement.

In an embodiment, needle protection adapter 200 is permanently attached to luer adapter 202. In another embodiment, luer adaptor 202 is connected to an echo-endoscope (not shown in Figure) via a screw thread type arrangement. Luer adapter 202 may be an over-molded component manufactured from a rigid or semi-rigid thermoplastic type polymer material such as acrylonitrile butadiene styrene, polystyrene and derivatives thereof, polyetherkeytone, polyamide, polyethersulfone, polyurethane, ether block amide copolymers, polyacetal, and derivatives thereof.

Figure 5:
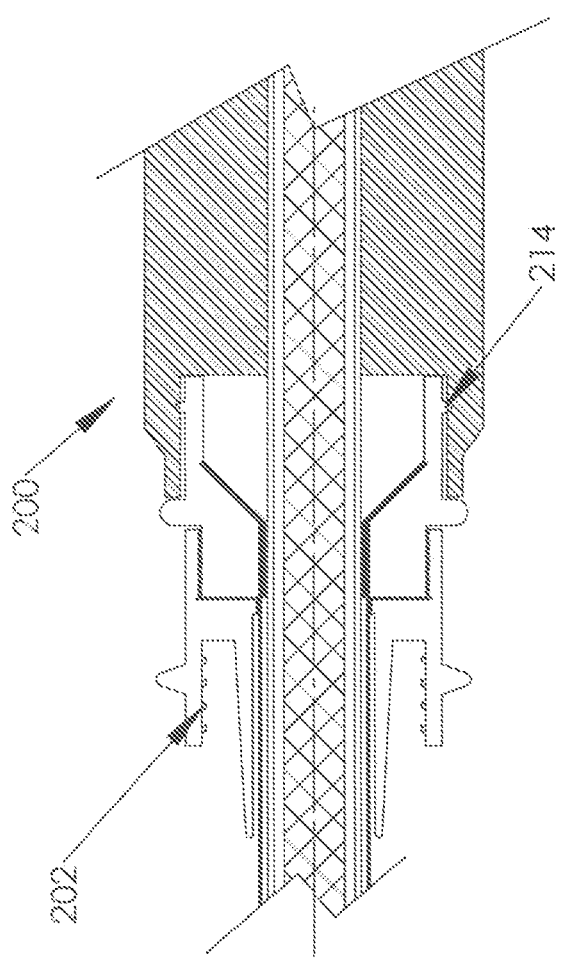
FIG. 5 is a perspective view of an embodiment of a luer adapter, according to the present disclosure.
Figure 6:
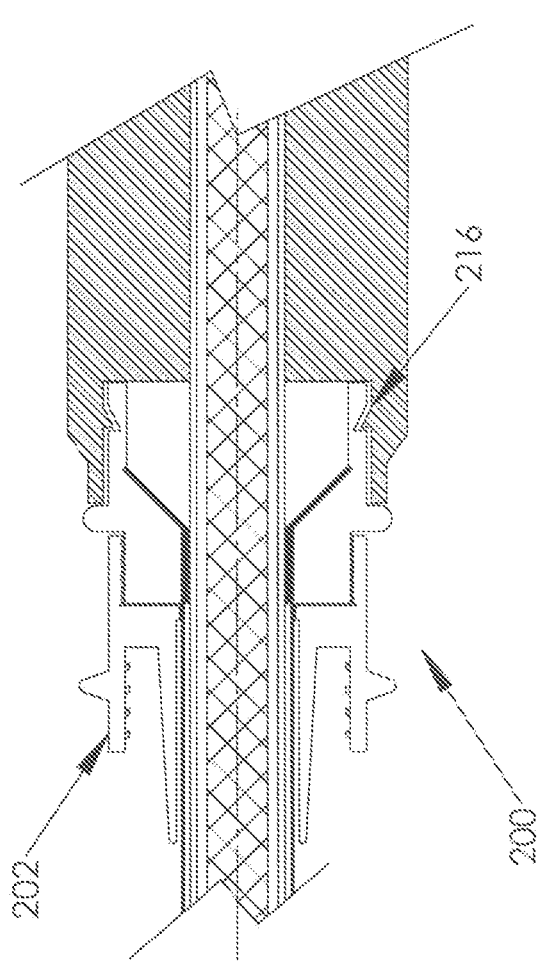
FIG. 6 is a perspective view of an embodiment of a luer adapter, according to the present disclosure.
Figure 12:
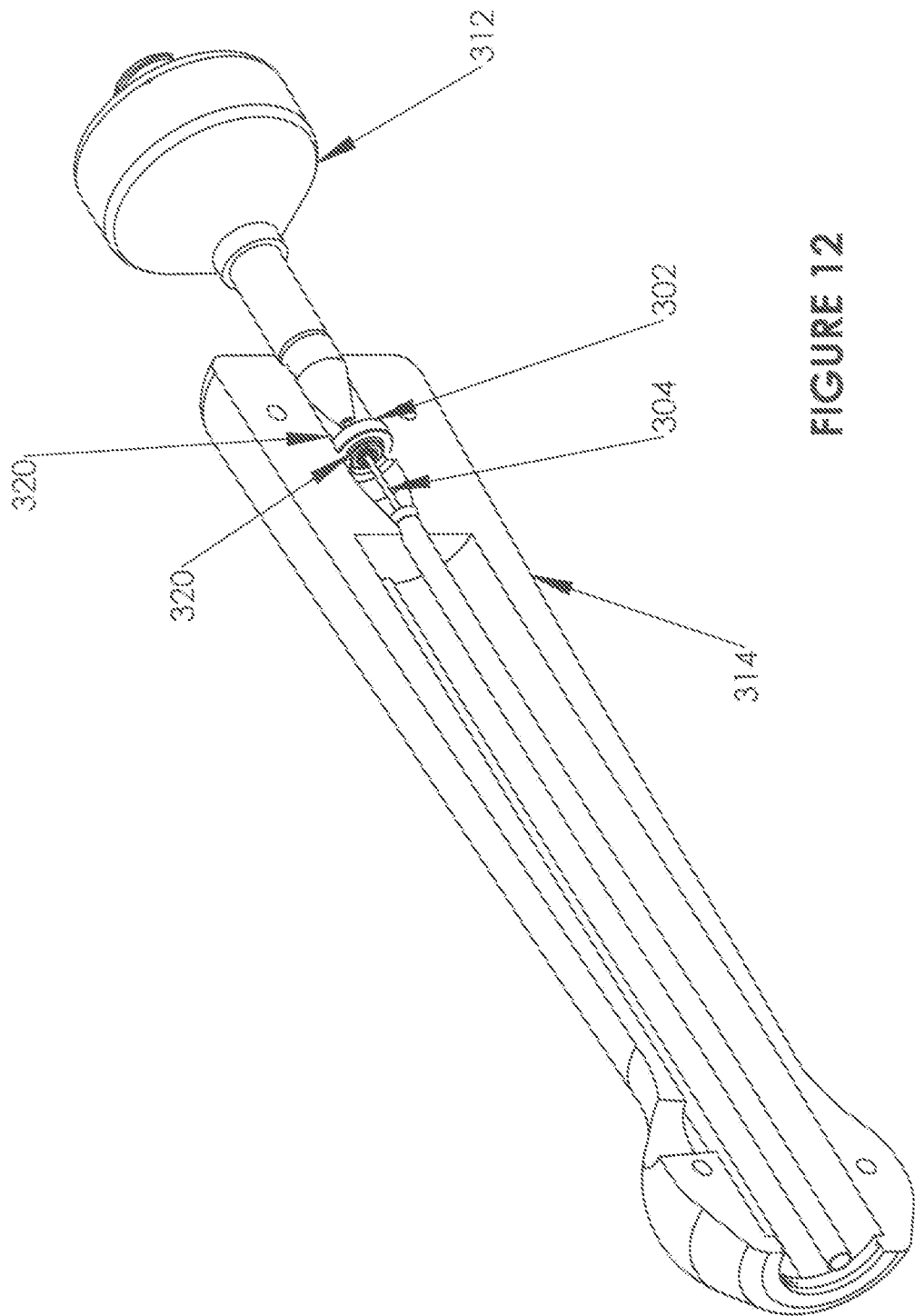
FIG. 12 is a perspective view of an embodiment of a needle protection member, according to the present disclosure.
Figure 13:
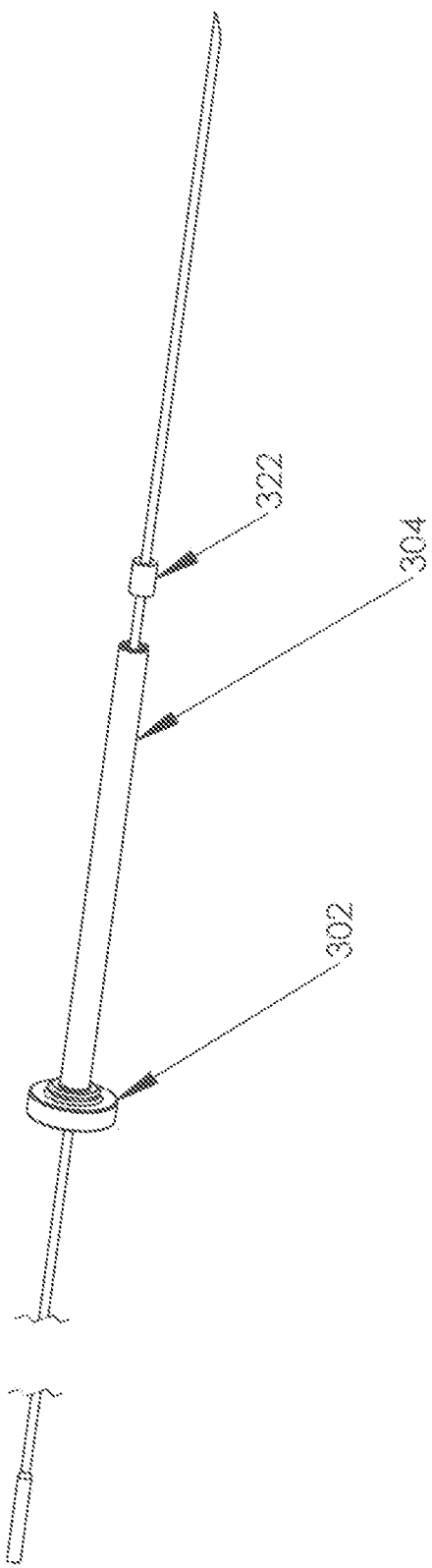
FIG. 13 is a perspective view of an embodiment of a needle protection member, according to the present disclosure.
Figure 14:
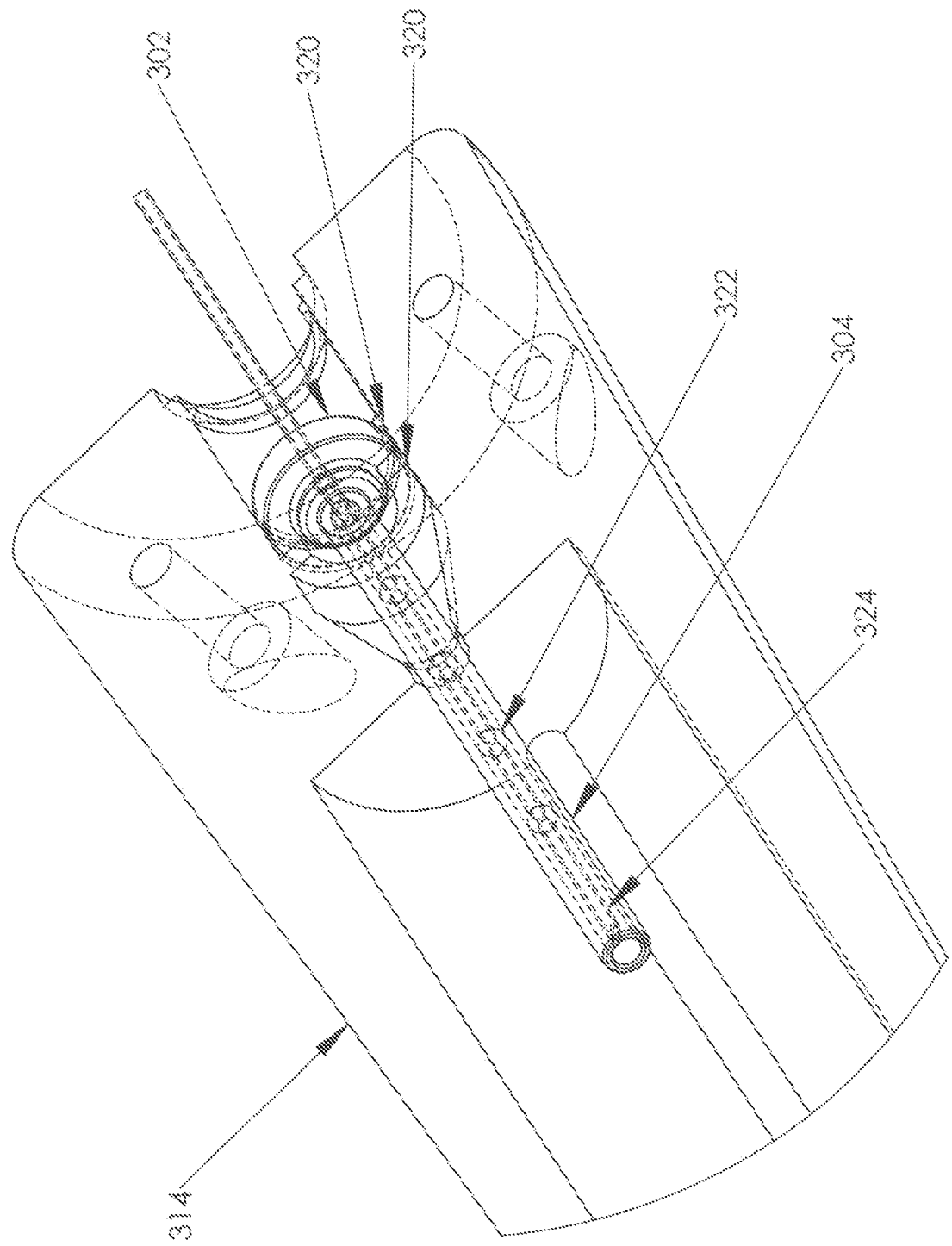
FIG. 14 is a perspective view of an embodiment of a needle protection member, according to the present disclosure.

Referring to FIGS. 5 and 6, perspective views of embodiments of luer adapter 202 are presented. Luer adapter 202 may be attached to needle protection adaptor 200 via snap fit connections 214 and 216. Snap fit connections 214 and 216 allow a clinician to disengage an echo-endoscope (not shown in Figure) from luer adapter 202 with relative ease. For example, once a sample has been aspirated from a desired anatomical site, an echo-endoscope may be detached from the distal end of luer adapter 202.

Referring to FIGS. 7 and 8, cross-sectional views of embodiments of needle protection adapter 200 are presented. Needle protection adapter 200 is comprised of a needle protection member 206 that extends from the middle portion of needle protection adapter 200 through the distal portion of needle protection adapter 200. Needle protection member 206 is comprised of a needle protection shaft 208 and at least one engagable member 222 on its internal diameter.

In an embodiment of the present disclosure, as a clinician retracts a sheath lumen 218 in a proximal direction, engagable member 222 communicates with a complimentary engagable member 220 located on the distal portion of sheath lumen 218. For example, sheath lumen 218 reaches a junction when engagable member 220 contacts engagable member 222 at the proximal end of needle protection member 206. At this juncture, a clinician may detach needle protection adapter 200 from luer adapter 202 as a needle 224 is completely protected within needle protection shaft 208. In this manner, needle protection shaft 208 can cover the distally protruding portion of needle 224 even when needle 224 is at its maximum length of extension from the distal end of needle protection member 206.

Referring to FIGS. 9 through 12, perspective views of embodiments of a needle protection member 300 and a needle biopsy device 310 are presented. Needle protection member 300 is comprised of a needle protection hub 302 and a needle protection shaft 304. Needle protection hub may be manufactured from, for example, rigid or semi-rigid thermoplastic materials such as acrylonitrile butadiene styrene, polystyrene and derivatives thereof, polyetherkeytone, polyamide, polyethersulfone, polyurethane, polyethylene, ether block amide copolymers, polyacetal, polycarbonate and derivatives thereof.

Needle biopsy device 310 is comprised of a needle housing member 312, a proximal handle member 314, a handle member 316, and a distal handle member 318. In an embodiment of the present disclosure, needle protection member 300 is pre-mounted distally on needle housing member 312. As needle housing member 312 is advanced into proximal handle member 314, needle protection hub 302 and needle protection shaft 304 are secured between engagable members 320. For example, needle protection hub 302 may be substantially secured between engagable members 320 that are snap-fit arrangements in proximal handle member 314.

Referring now to FIGS. 13 through 16, perspective views of embodiments of needle protection hub 302 and needle protection shaft 304 are presented. Needle protection hub 302 and needle protection shaft 304 may be injection molded components that are molded from a range of commercially available rigid or semi-rigid thermoplastic materials. These materials may be, are not limited to, acrylonitrile butadiene styrene, polystyrene and derivatives thereof, polyetherkeytone, polyamide, polyethersulfone, polyurethane, ether block amide copolymers, polyacetal, polycarbonate and derivatives thereof. In an embodiment, needle protection hub 302 and needle protection shaft 304 are also comprised of materials that are transparent or translucent in nature, such as polystyrene, polycarbonate, and styrene acrylonitrile. It is envisioned that the transparent or translucent function provides clinicians with visual feedback as to the location of a needle 324 relative to the distal portion of the needle protection shaft 304.

In an embodiment of the present disclosure, needle 324 includes engagable members 322 that are separated at a specific distance from the distal portion of needle 324. The location of engagable members 322 along needle 324 correspond to the maximum allowable length for needle penetration during sample acquisition. Engagable members 322 may be, for example, extruded polymeric spacers. As a clinician retracts needle 324 through needle protection shaft 322, needle protection hub 302 remains locked in proximal handle member 314 until at least one engagable member 322 engages a corresponding engagable member within needle protection hub 302. At this juncture, as the clinician applies additional retraction force, needle protection hub 302 disengages from engagement member 320 and needle 324 is encased as it is retracted from proximal handle member 314, thereby preventing inadvertent needle stick.

Referring to FIGS. 17A and 17B, perspective views of embodiments of a needle lock member are presented. In an embodiment of the present disclosure, needle lock member is comprised of a compression gasket 400, a compression fitting hub 410, and a cylindrical barrel 412. A needle 402 is partially disposed within compression gasket 400 and cylindrical barrel 412. Compression gasket 400 is partially disposed within compression fitting hub 410 and cylindrical barrel 412 is partially disposed within compression gasket 400. Compression gasket 400 may be, for example, manufactured from silicone and other soft deformable polymeric or rubber materials that can be compressed or decompressed as desired.

In an embodiment, compression gasket 400 may be in a compressed state 404 or an uncompressed state 405. Referring now to FIG. 17A, in compressed state 404, compression gasket 400 is in contact with a portion of needle 402, thereby preventing needle 402 from being advanced or retracted out of the distal end of a catheter sheath 406. At this juncture, the clinician may attach an adaptor 408 to an echo-endoscope by engaging the luer component of the working channel of the scope (not shown in Figure) with adaptor 408. Referring now to FIG. 17B, the clinician may then rotate compression fitting hub 410, thereby connecting compression fitting hub 410 onto adaptor 408. This rotational motion results in compression gasket 400 being displaced in a distal direction. This rotation also results in the displacement of cylindrical barrel 412 through compression gasket 400 at its proximal end. At this juncture, once compression fitting hub 410 and adaptor 408 are secured in place, compression gasket 400 is no longer in contact with needle 402. Needle 402 may then advance or retract freely to acquire a desired sample.

Figure 18A:
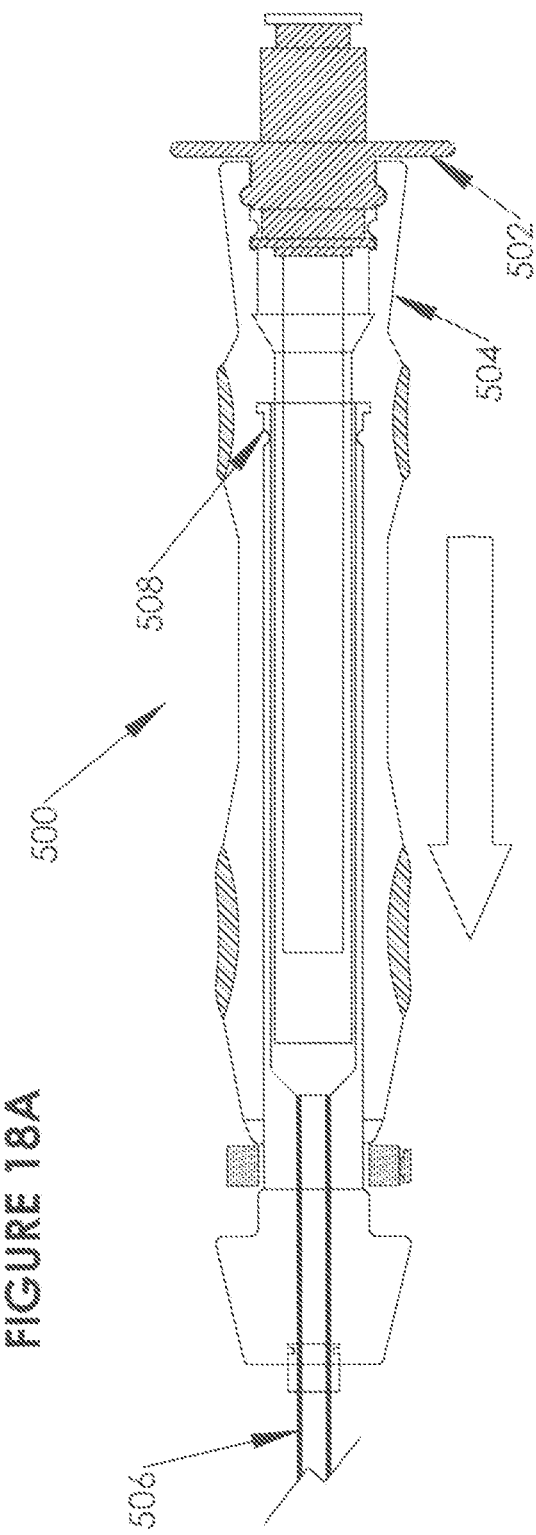
FIG. 18A is a perspective view of an embodiment of a needle protection member, according to the present disclosure.
Figure 18B:
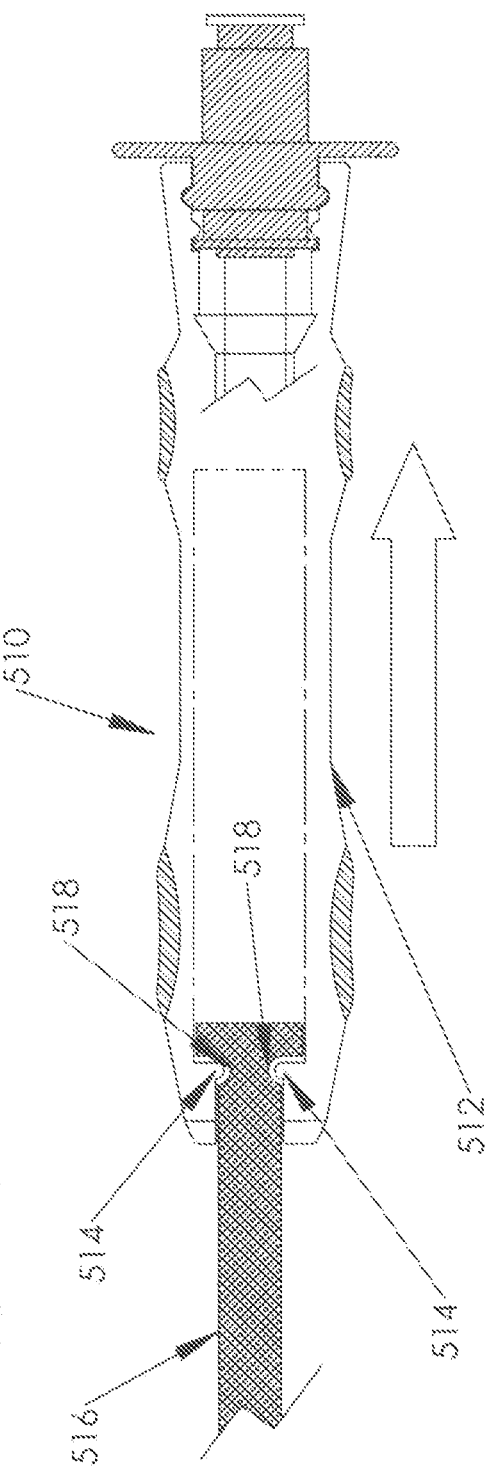
FIG. 18B is a perspective view of an embodiment of a needle protection member, according to the present disclosure.

Referring to FIGS. 18A and 18B, perspective views of embodiments of needle protection mechanisms for use with a needle biopsy device 500 and 510 are presented. Needle biopsy device 500 is comprised of a needle housing member 502, a proximal handle member 504, and a handle member 506. Needle housing member 502 includes a needle therein. Needle biopsy device 510 is comprised of a proximal handle member 512 and a handle member 516.

In an embodiment, needle housing member 502 is fully inserted into proximal handle member 504 to allow the needle to extend from the distal end of the sheath lumen (not shown in Figure). In this regard, once a clinician has acquired a tissue sample, the clinician may retract proximal handle 504 to its maximum stroke to ensure that the needle becomes housed within the distal portion of the sheath lumen. In order to facilitate this process, needle biopsy device 500 incorporates a first engagable member 508 at the proximal end of proximal handle member 504, a second engagable member 514, and a third engagable member 518 at the proximal end of the handle member 516. The use of such engagable members prevents proximal handle member 504 from moving forward without the application of force by the clinician. This feature also provides tactile feedback to alert the clinician that the needle is locked because the clinician can feel engagable members 508, 514, and 518 clicks into position. It is contemplated that this design feature also ensures that the clinician is not solely reliant on having to lock the locking slide ring in place prior to removal of sheath lumen 506. It is further contemplated that incorporating a self-locking mechanism such as engagable members 508, 514, and 518 also eliminates the need for the clinician to lock the locking slide ring in place, thereby also increasing procedural efficiency. Furthermore, by leaving the locking ring locked at a specific location on handle member 504, the clinician can maintain needle penetration settings between successive needle passes in acquiring multiple tissue samples.

Figure 19:
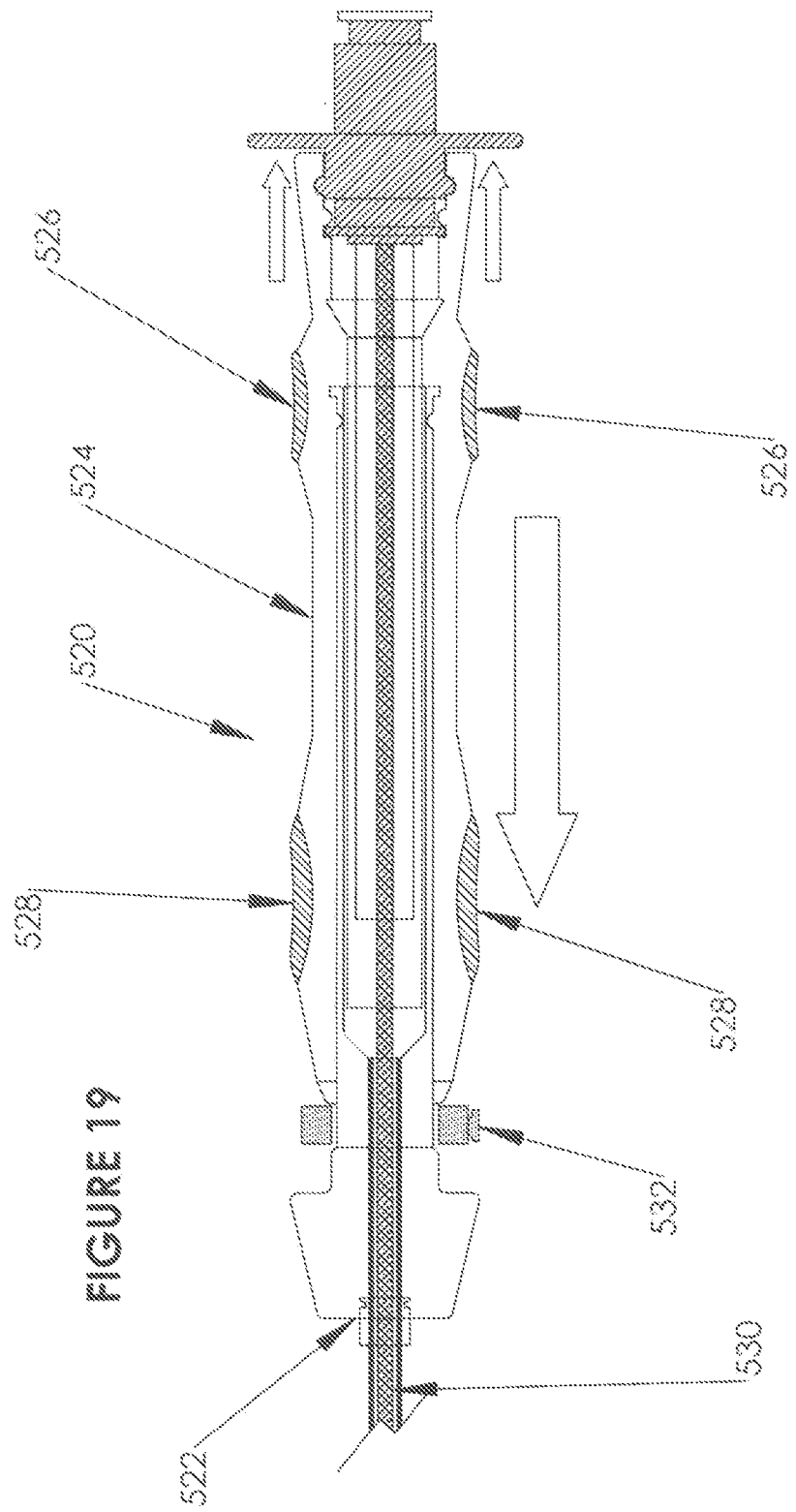
FIG. 19 is a perspective view of an embodiment of a needle biopsy device, according to the present disclosure.

Referring to FIG. 19, a perspective view of another embodiment of a needle biopsy device 520 is presented. Needle biopsy device 520 is comprised of an adaptor 522, a proximal handle member 524, ergonomic design features 526 and 528 disposed on proximal handle member 524 and distal handle member (not shown in Figure), a locking ring 532, and a needle 530. In an embodiment, needle biopsy device 520 does not facilitate catheter shaft adjustment when needle biopsy device 520 is attached to an echo-endoscope.

Proximal handle member 524 incorporates ergonomic design features 526 and 528 in order to provide a clinician with enhanced feel of needle biopsy device 520. Ergonomic features 526 and 528 may be, for example, a conical grip or depressions suitable for a thumb or forefinger. Locking ring 532 allows a clinician to lock the depth of needle extension from the end of the sheath lumen of the device. Locking ring 532 may be moved distally or proximally and can be locked in position via tightening.

Referring now to FIGS. 20A through 24, perspective views of embodiments of a design feature for needles are presented. The needle incorporates echogenic features over its length of the distal end when exposed to its maximum extension length. This functionality is achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

Figure 20A:
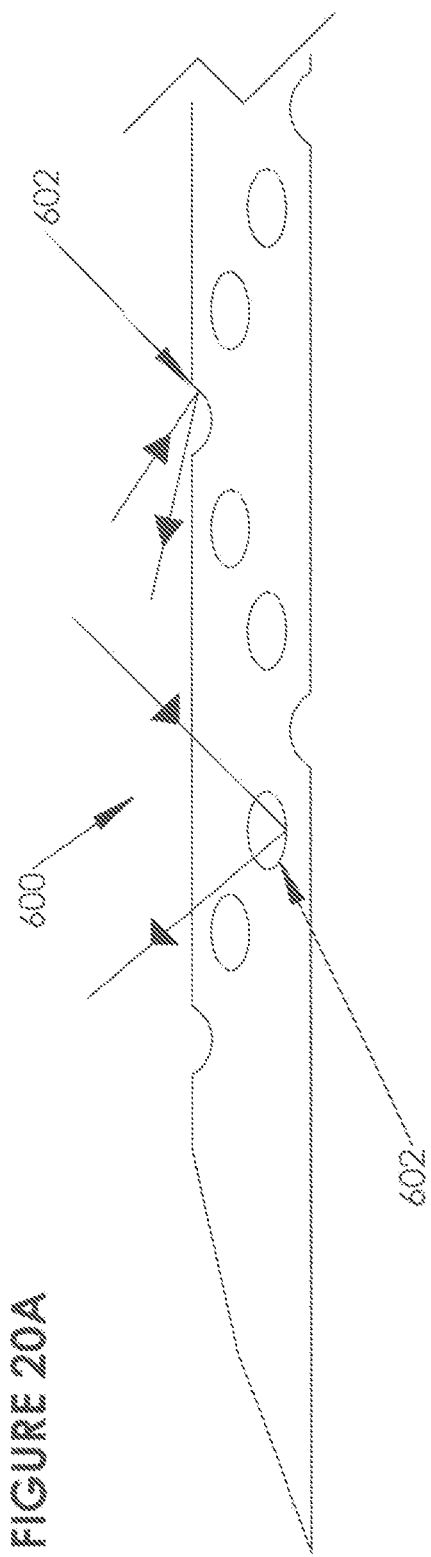
FIG. 20A is a perspective view of an embodiment of a needle, according to the present disclosure.
Figure 20D:
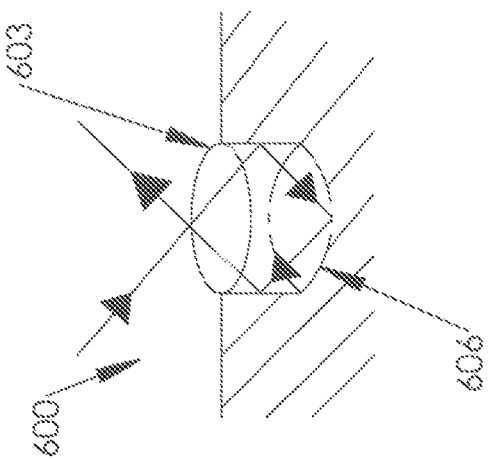
FIG. 20D is a perspective view of an embodiment of a needle, according to the present disclosure.
Figure 20C:
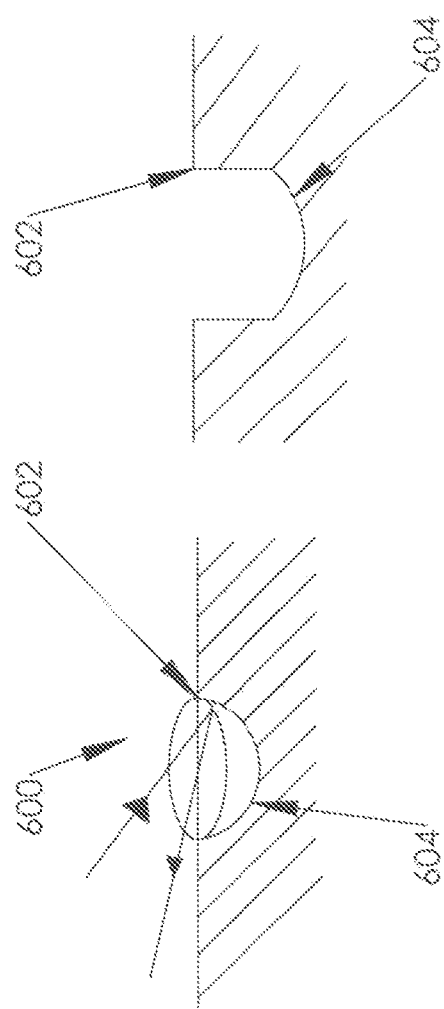
FIG. 20C is a perspective view of an embodiment of a needle, according to the present disclosure.
Figure 20B:
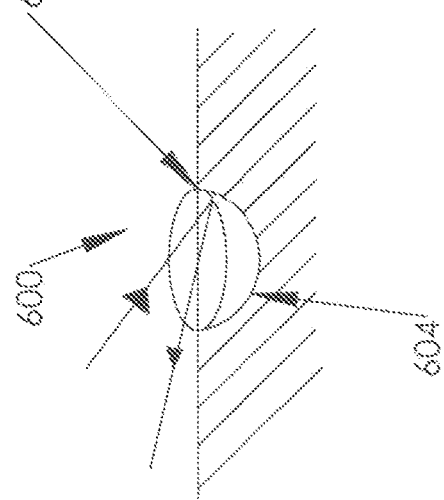
FIG. 20B is a perspective view of an embodiment of a needle, according to the present disclosure.
Figure 20G:
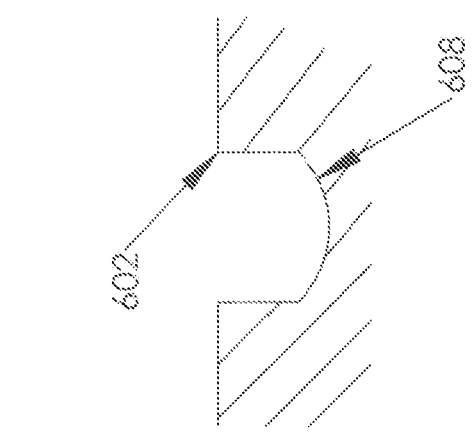
FIG. 20G is a perspective view of an embodiment of a needle, according to the present disclosure.
Figure 20F:
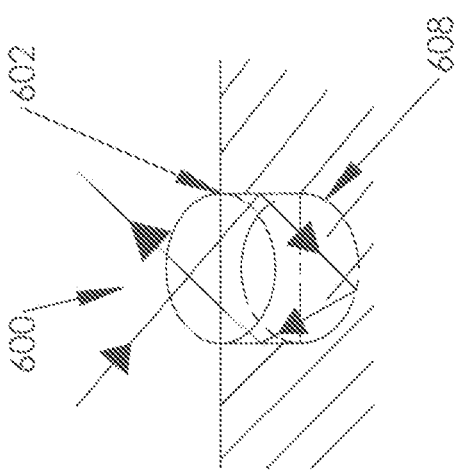
FIG. 20F is a perspective view of an embodiment of a needle, according to the present disclosure.
Figure 20E:
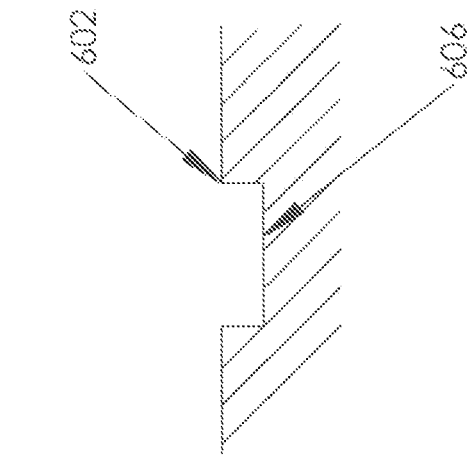
FIG. 20E is a perspective view of an embodiment of a needle, according to the present disclosure.

Referring now to FIG. 20A, a perspective view of an embodiment of a needle 600 is presented. Needle 600 is comprised of a plurality of depressions 602. Depressions 602 may be, but are not limited to, circular, concave, cylindrical, helical, oval, rectangular, and square elements that take the form of indentations on the surface of needle 600. Depressions 602 may be arranged in a helical (spiral) fashion around the circumference of the distal needle end. These indentations may extend to the extreme end of the bevel or may end at a specific distance from the bevel of needle 600. The length of the distal end of needle 600 containing these depressions may be, for example, from one to twenty centimeters. In another embodiment, the length is between five to ten centimeters. Referring to FIGS. 20B and 20C, depression 602 have a concave detail 604. Referring to FIGS. 20D and 20E, depressions 602 have a square base edge 606. Referring to FIGS. 20F and 20G, depressions 602 have a hemispherical base detail 608.

Figure 21:
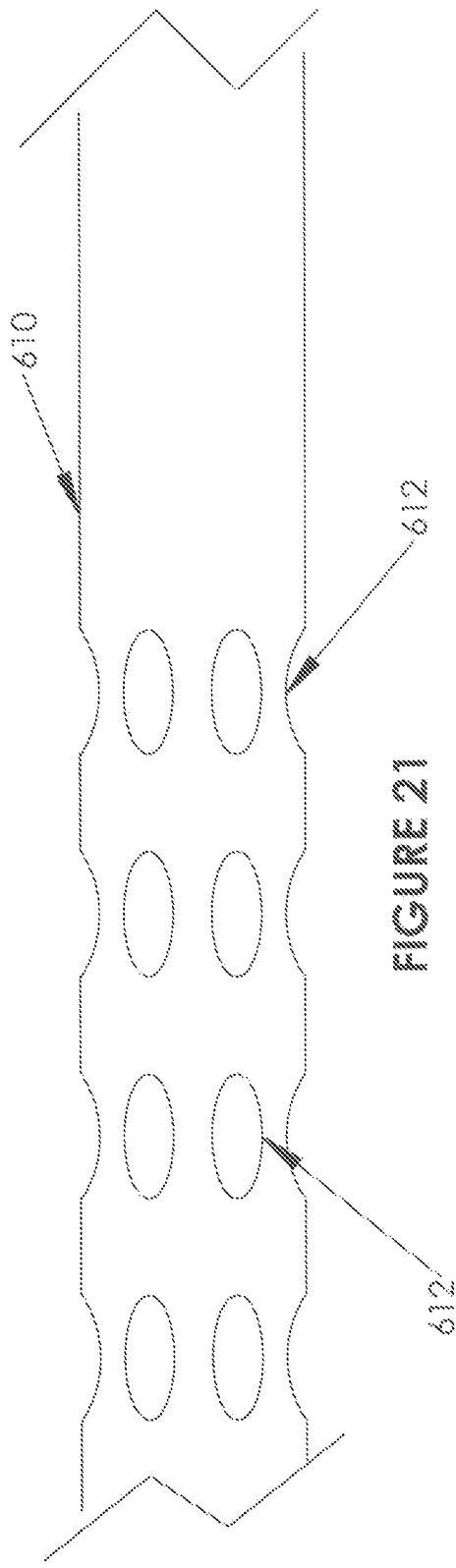
FIG. 21 is a perspective view of an embodiment of a needle, according to the present disclosure.
Figure 22:
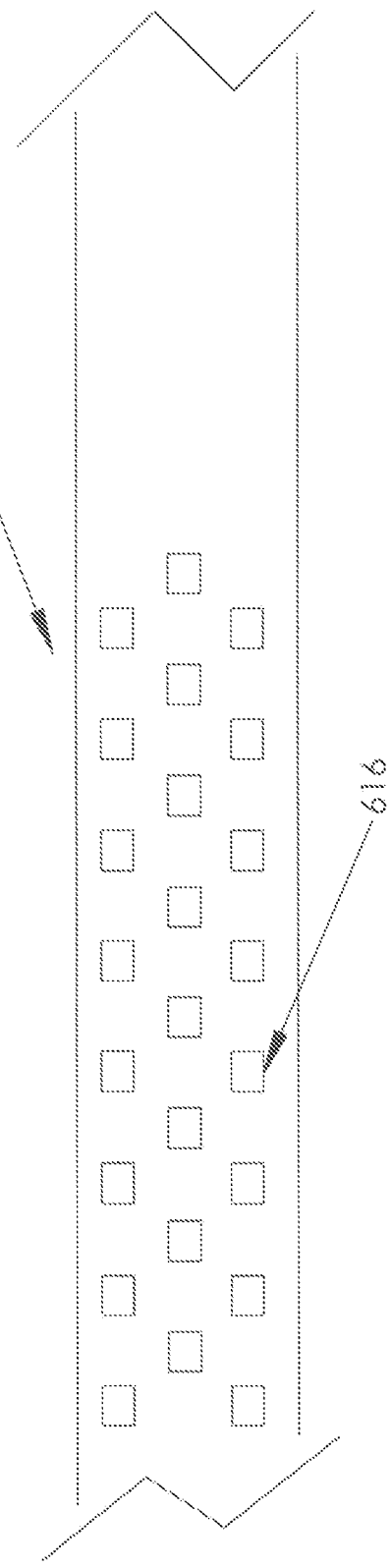
FIG. 22 is a perspective view of an embodiment of a needle, according to the present disclosure.
Figure 23A:
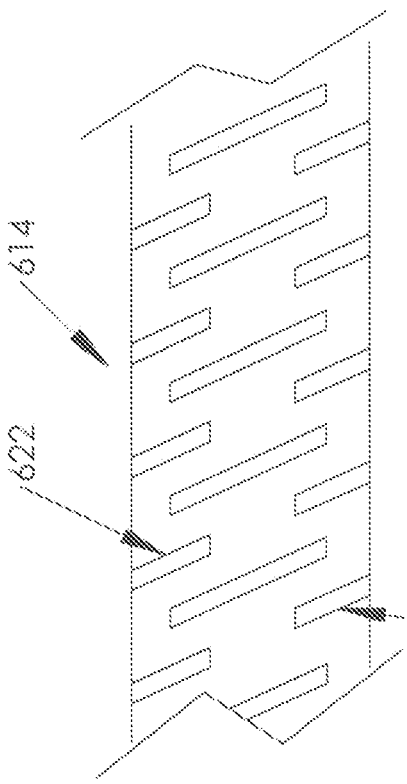
FIG. 23A is a perspective view of an embodiment of a needle, according to the present disclosure.
Figure 23B:
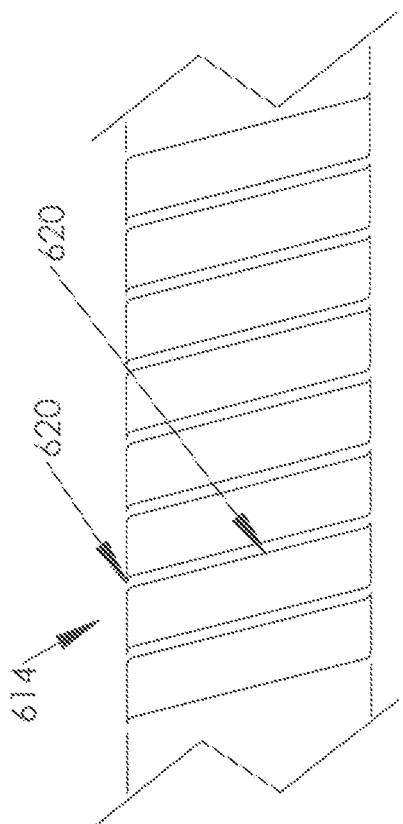
FIG. 23B is a perspective view of an embodiment of a needle, according to the present disclosure.

Referring now to FIG. 21, a perspective view of another embodiment of a needle 610 is presented. Needle 610 is comprised of elliptical depressions 612 around the circumference of the distal end of needle 610. Referring to FIG. 22, a perspective view of an embodiment of a needle 614 having square depressions 616 is presented. Depressions 616 may extend to the extreme end of the bevel or may end at a specific distance from the bevel of needle 614. Referring to FIGS. 23A and 23B, embodiments of needle 614 including spiral depressions 620 and helical depressions 622 are presented. Referring to FIGS. 23C, a depression 624 has a concave detail. Referring to FIGS. 23D, a depression 626 has a square base edge. Referring to FIGS. 23E, a depression 628 has a hemispherical base detail.

Referring now to FIG. 24, a diagram of ultrasound waves impinging upon a needle depression at angles of $\alpha 1$ 630 and $\beta 1$ 632 respectively are presented. In an embodiment, a wave strikes the base of the depression and is reflected upwards at angle of reflection of $\alpha 2$ 634 and $\beta 2$ 636 respectively, which are equal to the angles of incidence of $\alpha 1$ 630 and $\beta 1$ 632 respectively. This reflected beam is reflected a second time off the adjacent wall of the depression at an angle of reflection of $\alpha 3$ 638 and $\beta 3$ 640 respectively, which are equal to the angles of incidence, $\alpha 1$ 630 and $\beta 1$ 632 respectively and the angles of first reflection $\alpha 2$ 634 and $\beta 2$ 636 respectively. In this manner, the reflected wave becomes reflected along the same angle of incidence as the initially propagated incident beam back to the transducer of the ultrasound device. In an embodiment, a square edge depression design may provide for more efficient remittance of ultrasound waves during the procedure.

Figure 25:
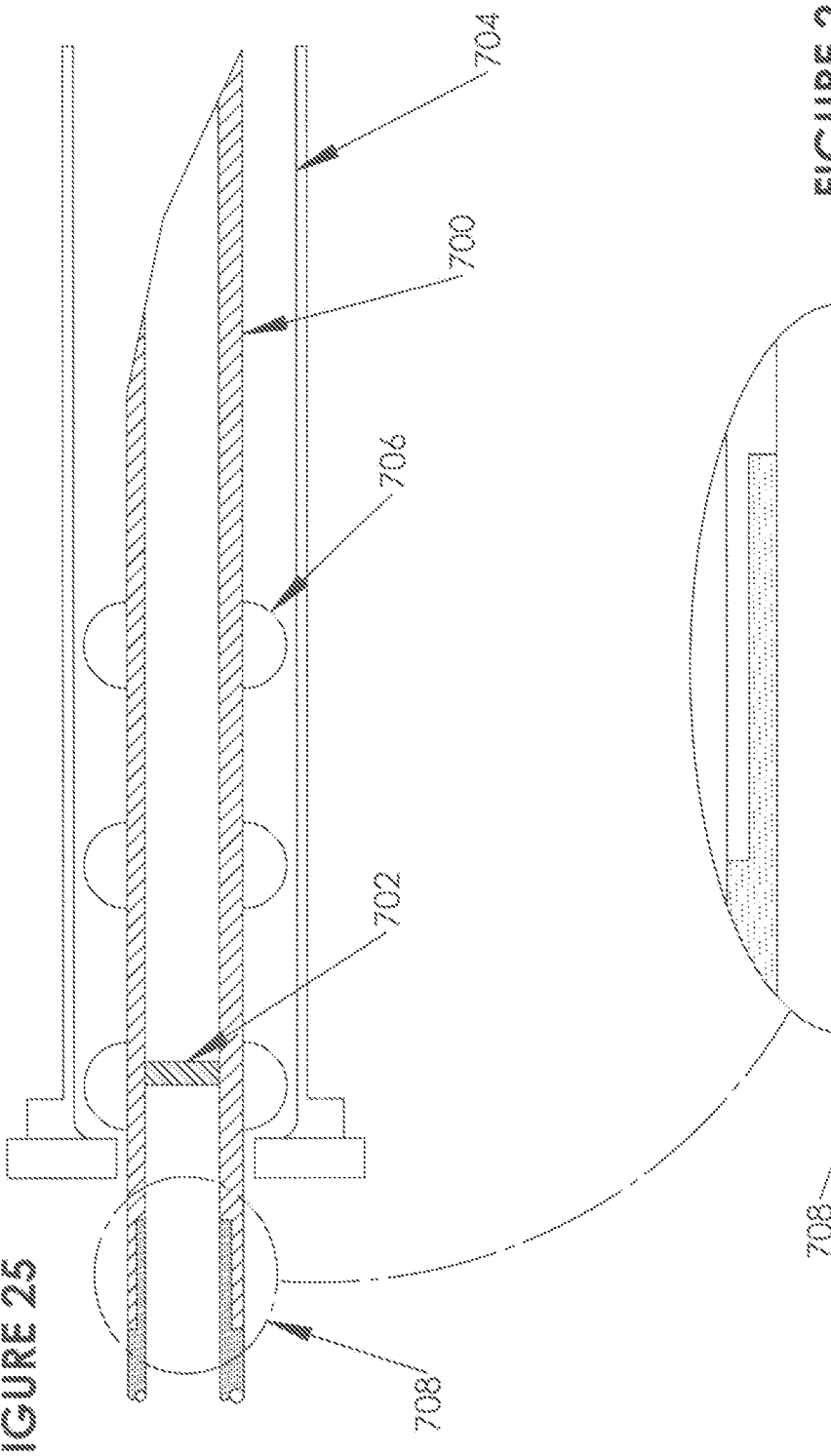
FIG. 25 is a perspective view of an embodiment of a needle, according to the present disclosure.
Figure 26:
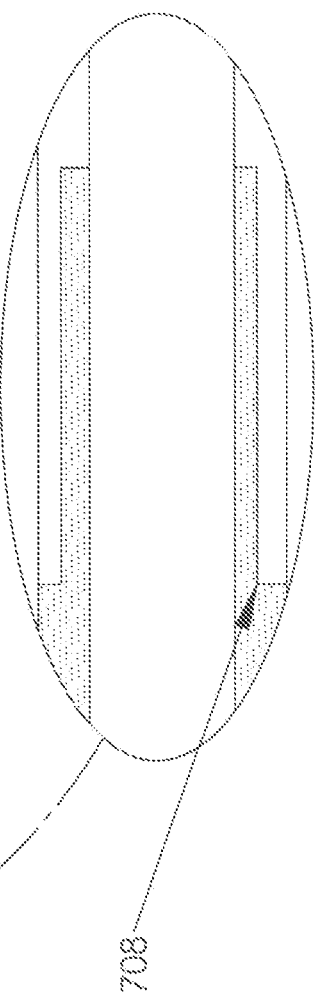
FIG. 26 is a perspective view of an embodiment of a needle, according to the present disclosure.
Figure 27:
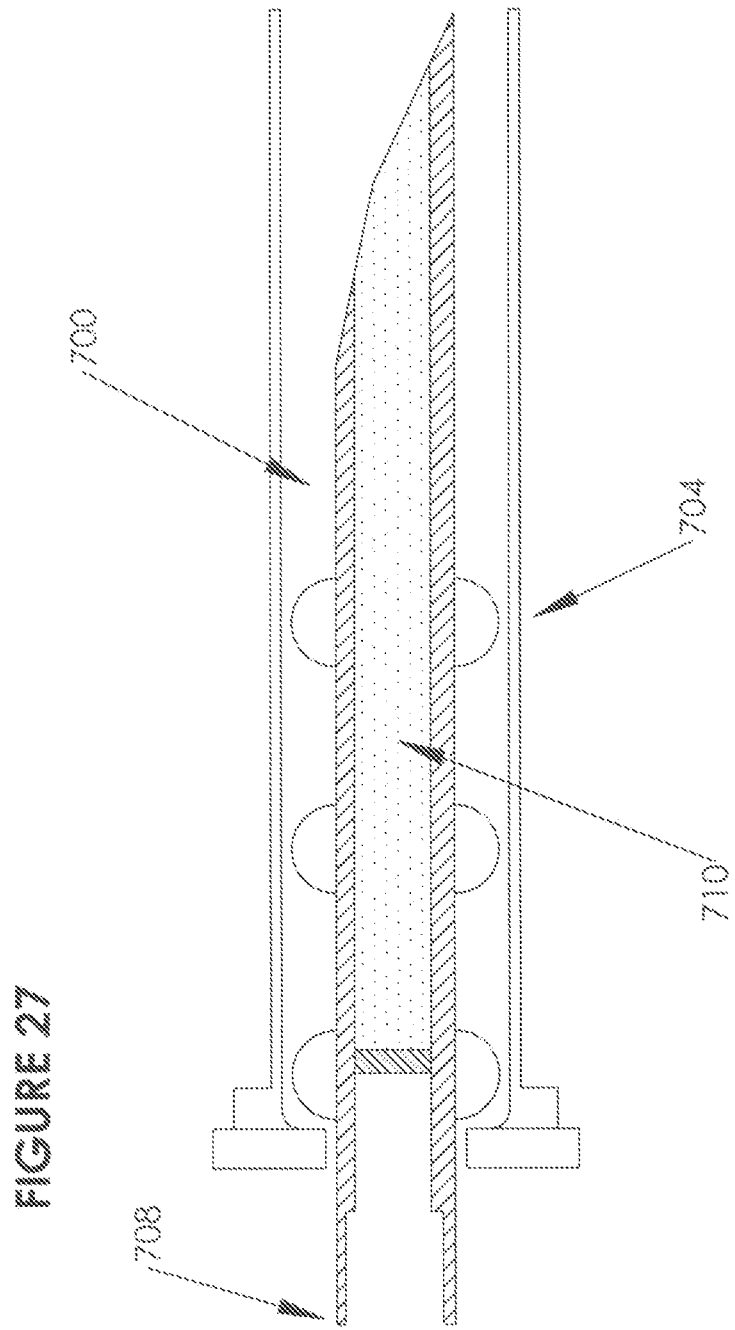
FIG. 27 is a perspective view of an embodiment of a needle, according to the present disclosure.

Referring now to FIGS. 25 through 27, perspective views of an embodiment of another design feature for a needle 700 are presented. Needle 700 is comprised of a filter element 702, at least one protrusion 706, a joint 708, and is housed within a needle protection member 704.

In an embodiment of the present disclosure, joint 708 permits a clinician to detach the distal portion of needle 700 from the main body of needle 700. Joint 708 may be, for example, a lap, snap-fit, or adhesive joint arrangement. It is envisioned that joint 708 shall not compromise the pushability or kink resistance of needle 700 during sample extraction.

Filter element 702 acts as a membrane to capture cells acquired during an aspiration process. During a procedure, post-aspiration, a clinician may detach the needle housing member from the handle of the needle biopsy device at the proximal handle end. Once completely retracted, the sharp end of needle 700 is protected by needle protector 704. Once a clinician detaches needle 700 at joint 708, he or she may safely insert needle 700 into a vile for laboratory analysis. In this manner, the efficiency of a fine-needle aspiration procedure may be improved by eliminating sample prep time in the EUS or EBUS suite, which is normally taken up with waiting for the sample to be removed from needle 700 before a successive needle pass may be made.

Figure 28:
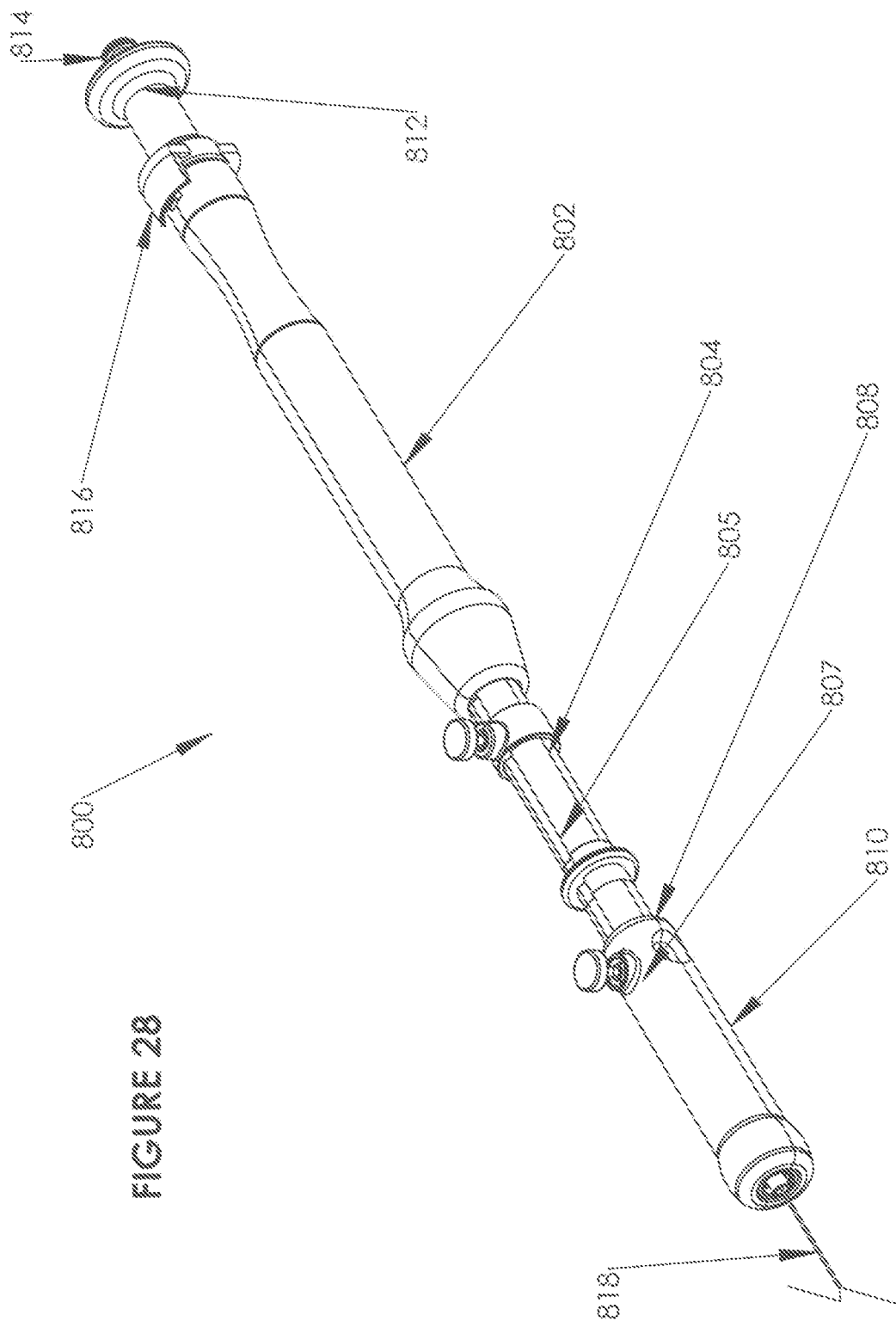
FIG. 28 is a perspective view of an embodiment of a needle biopsy device, according to the present disclosure.
Figure 29:
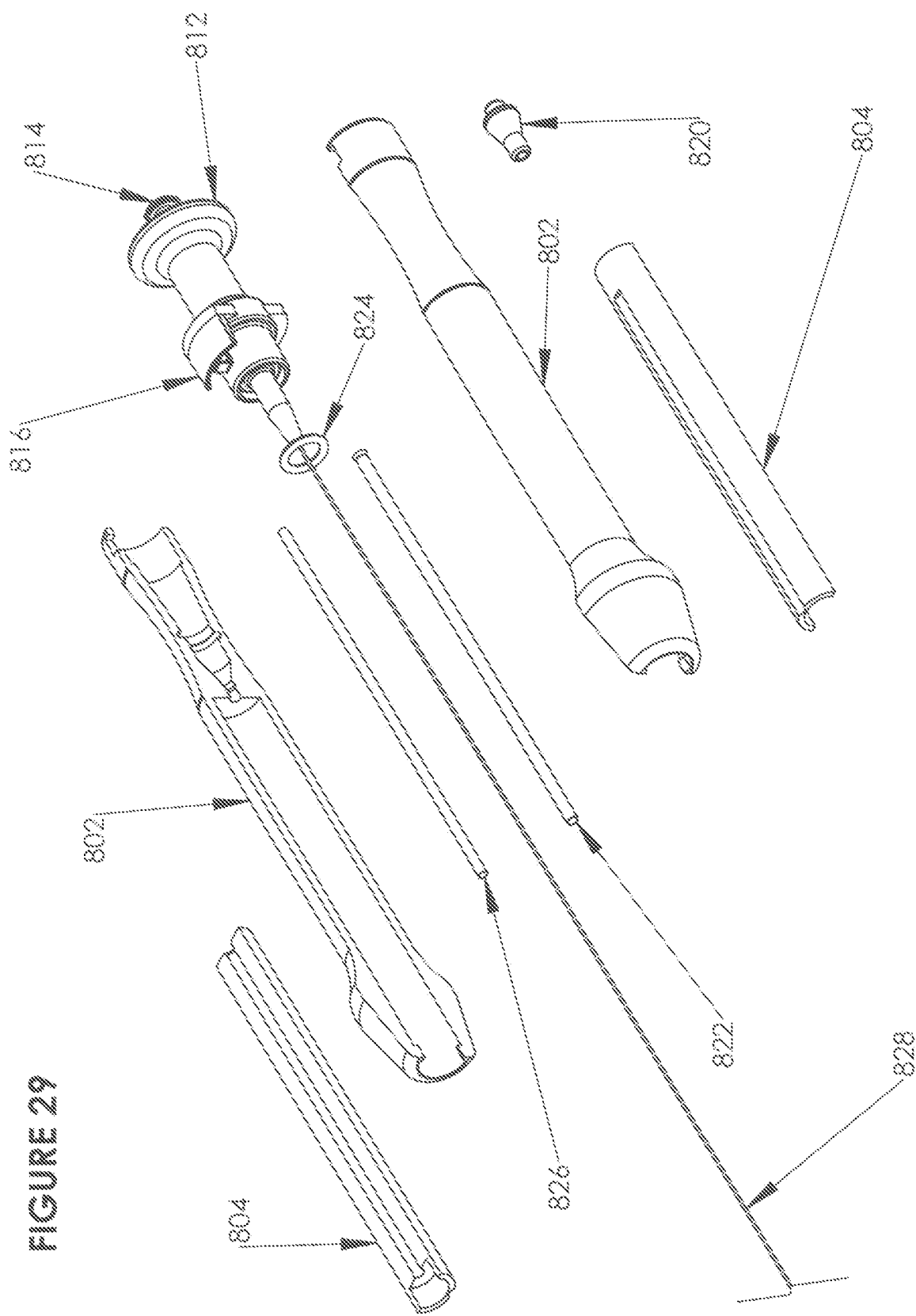
FIG. 29 is a perspective view of an embodiment of a needle biopsy device, according to the present disclosure.

Referring now to FIGS. 28 through 45, various embodiments of a needle biopsy device with an exchangeable needle housing member are presented. Referring to FIGS. 28 and 29, a needle biopsy device 800 is presented. Needle biopsy device 800 is comprised of a proximal handle member 802, a proximal inner handle member 804, a proximal guide-rail 805, a stop member 806, a distal guide-rail 807, a distal inner handle member 808, a distal handle member 810, a needle housing member 812, a stylet 814, a release member 816, a sheath lumen 818, a needle protection hub 820, a needle protection shaft 822, a ring engagable member 824, a proximal inner handle shaft 826, and a needle 828.

Proximal handle member 802 is used to provide a slideable method to advance and retract needle 828 along proximal inner handle member 804. For example, proximal guide-rail 805 located at the distal end of the proximal inner handle member 804 provides recess grooves to allow movement of needle 828 into and out of a tumerous location.

Distal handle member 810 is used to provide a slideable method to adjust the protrusion depth of sheath lumen 818 relative to the extended length of needle 828 along distal inner handle member 808.

In an embodiment, needle housing member 812 is preloaded with an integrated needle protection mechanism (not shown in Figure). It is contemplated that once a clinician has acquired a cellular sample, needle housing member 812 may be unlocked from proximal handle member 802 by depressing release member 816. Release member 816, may be, for example, an external push-button hinge. The act of manipulating release member 816 allows a clinician to unlock needle housing member 812 and retract the needle from device 800.

Referring to FIGS. 30 and 31, a perspective view of an embodiment of proximal handle member 802 is presented. Proximal handle member 802 is comprised of recessed portions 830 to allow for the positioning of ring engagable member 824 and proximal guide rails 805. Proximal handle member 802 is free to slide forward and backward along proximal guide rail 805, thus allowing the clinician to advance or retract the needle during a procedure. It is contemplated that the distal handle member (not shown in Figure) is free to slide forward and backward along the distal guide-rail, allowing to clinician to adjust the depth of sheath lumen 818 extension beyond the end of an echo-endoscope.

Referring to FIGS. 32A through 32D, perspective views of components of the handle members are presented. Distal handle member 810 is comprised of at least one bore recess 834, a locking engagement bore 836, and a luer recess 838. In an embodiment, a threaded spacer may be inserted into bore recess 834 and secured in position. The step of securing may be performed by, for example, a mechanical press-fit or via the use of adhesive.

Proximal inner handle member 804 and distal inner handle member 808 are separated by a stop member 806. Stop member 806 acts as a divider to control the advancement and retraction of the handle member components along proximal inner handle member 804 and distal inner handle member 808. In an embodiment, stop member 806 is secured to a proximal member recess 840. It is contemplated that stop member 806 does not interfere with the functionality of a tapered passage 842 for needle exchange and a land bore 844.

Referring now to FIG. 33, a perspective view of an embodiment of needle housing member 812 is presented. Needle housing member 812 is comprised of a land ring 813 and a stylet 814. Land ring 813 functions in conjunction with release member 816. The functional aspects of land ring 813 are described in further detail below.

Referring now to FIG. 34, a cross-sectional view of an embodiment of needle housing member 812 is presented. Needle housing member 812 is comprised of ring engagable member 824, a needle luer hub 840, an inner housing 842, a needle strain relief member 844. In an embodiment, inner housing 842 incorporates a shelf that engages and disengages with release member 816 (as shown in FIG. 29). This design feature provides the clinician with a smooth locking response when securing the needle housing member to the assembly of release member 816. Needle luer hub 840 may be secured to needle housing member 812 via various securing means, such as adhesive bonding, welding, brazing or soldering techniques. Inner housing 842 serves as a coupler to hold needle strain relief member 844 in position.

Figure 37:
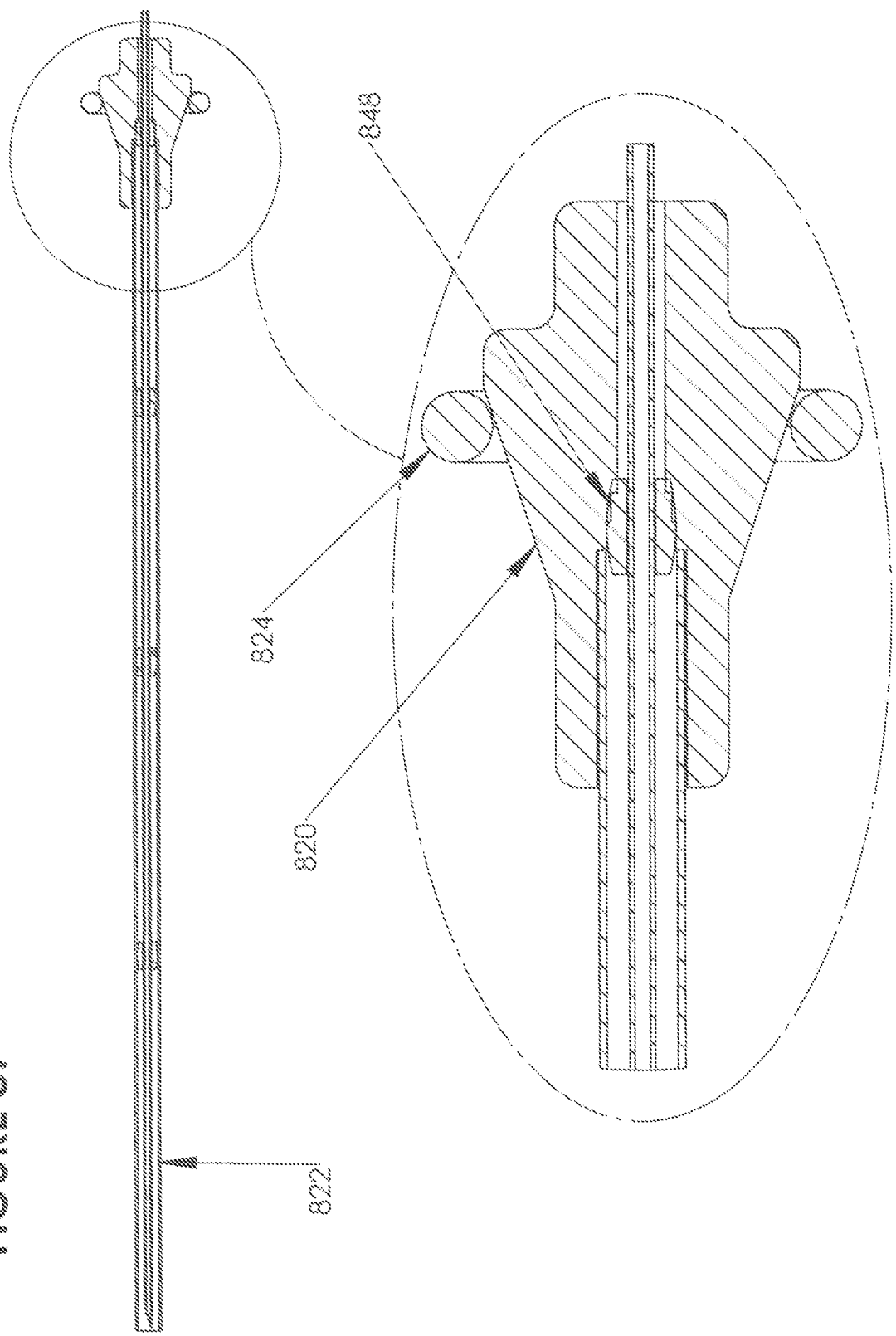
FIG. 37 is a perspective view of an embodiment of a needle biopsy device, according to the present disclosure.

Referring now to FIGS. 35 through 37, perspective views of embodiments of needle protection hub 820 for use with needle housing member 812 are presented. Needle protection hub 820 includes an engagable member 846. Engagable member 846 communicates with protrusions 848 at the distal end of the needle. As a needle is continually retracted, the most proximal protrusion 848 interfaces with engagable member 846 and becomes mechanically locked thereto. At this juncture, as the clinician retracts the needle housing member from the proximal handle, needle protection hub 820 remains locked to protrusion 848, thus encasing the sharp bevel of the needle and protecting the clinician after the needle has been removed from the patient.

Needle protection hub 820 may be manufactured from, for example, a rigid, non-deformable metallic, thermoplastic or thermoset materials such as aluminum, stainless steel, acrylonitrile butadiene styrene (ABS), styrene acrylonitrile (SAN) or rigid derivatives thereof, polyamide, polyethylene, polyurethane, and polycarbonate. In an embodiment, these materials shall have a durometer in the range of 35-120 Shore D, but more preferably in the range of 80-110 Shore D.

It is envisioned that engagable members 846 may be manufactured from a range of low durometer, thermoplastic or thermoset materials such as, but not limited to, polyurethane and derivatives thereof, polyether amide block copolymers, polyamide, styrene butadiene rubber and/or alternate derivatives of styrene based polymers, neoprene, and polyethylene and derivatives thereof. In an embodiment, the materials of manufacture shall have a durometer in the range of 70-120 Shore A, but more preferably in the range of 70-90 Shore A.

Figure 38B:
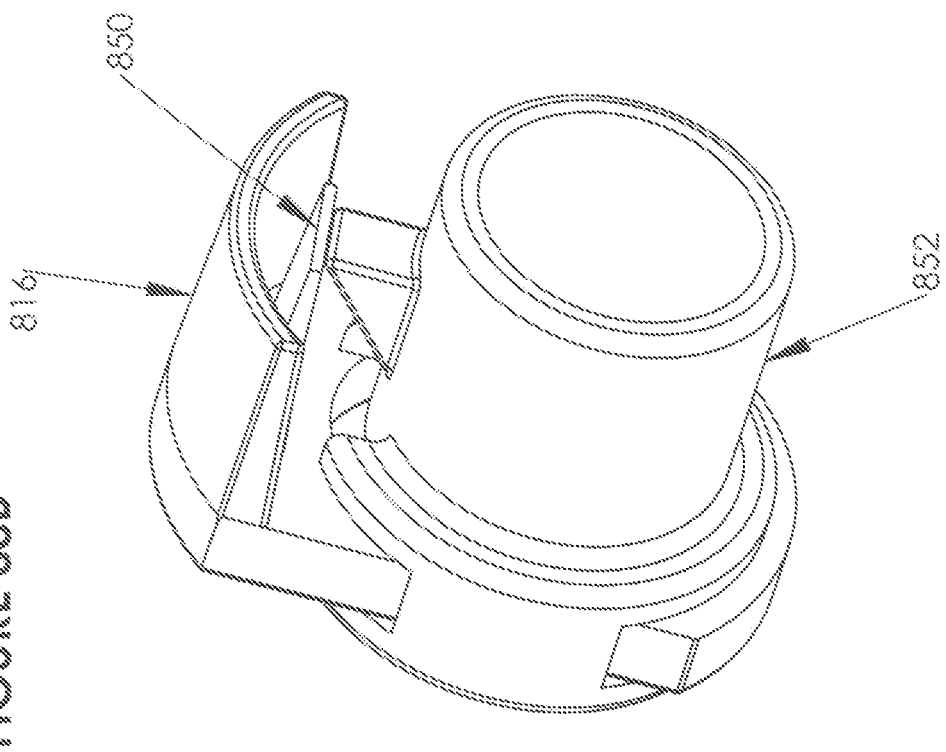
FIG. 38B is a perspective view of an embodiment of a needle biopsy device, according to the present disclosure.
Figure 38A:
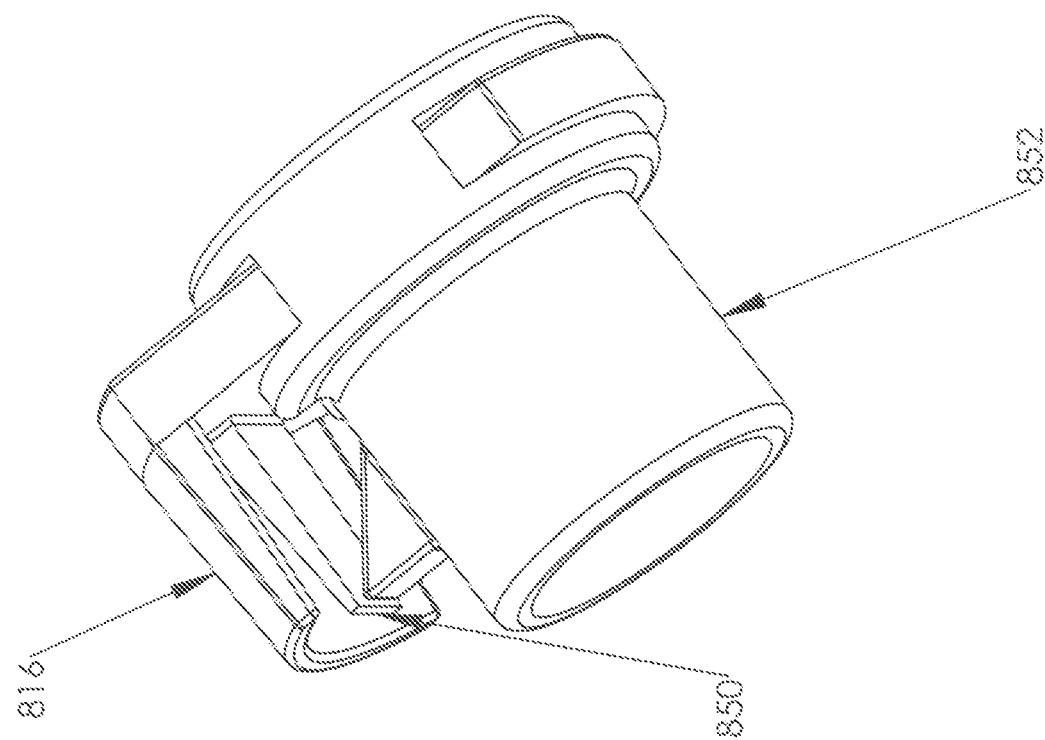
FIG. 38A is a perspective view of an embodiment of a needle biopsy device, according to the present disclosure.
Figure 39B:
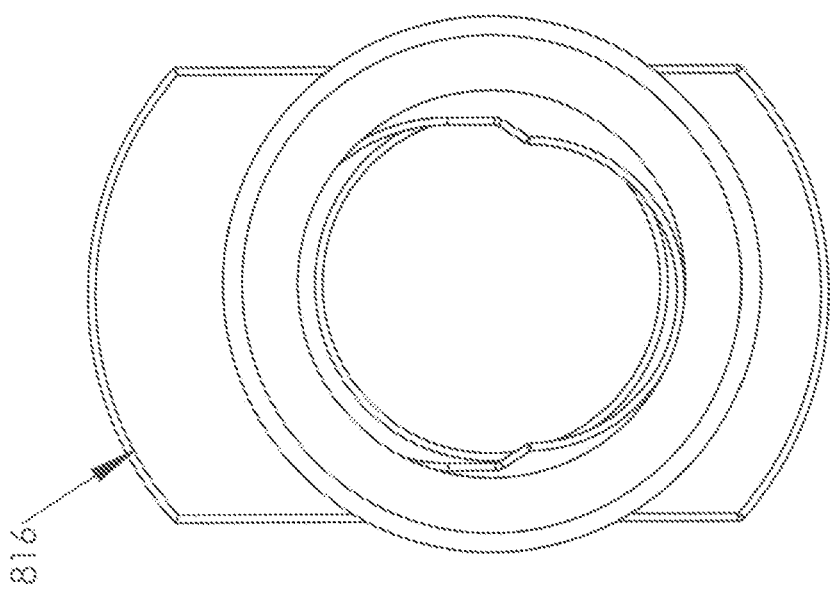
FIG. 39B is a perspective view of an embodiment of a needle biopsy device, according to the present disclosure.
Figure 39A:
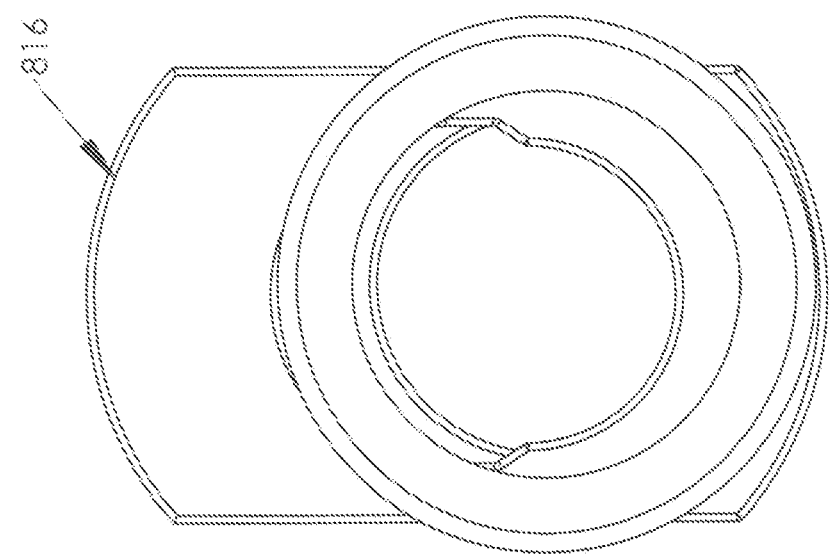
FIG. 39A is a perspective view of an embodiment of a needle biopsy device, according to the present disclosure.

Referring now to FIGS. 38A through 39B, various views of an embodiment of release member 816 are presented. Release member 816 represents a mechanism to attach the needle housing member to the proximal handle member of the needle biopsy device. Release member 816 may be, for example, a push-button, that activates the use of a hinge member 850 to provide for a return to the "Home" position once external force is not applied to release member 816. Hinge member 850 can elastically deform to provide for the opening and closing of the "lock" during removal of the needle housing member. In an embodiment, release member 816 incorporates an external coupler housing 852 and a push button 816 design mechanism. Referring now to FIGS. 39A and 39B, release member 816 illustrates release member 816 in the CLOSED and OPEN positions during a typical actuation cycle.

Referring now to FIGS. 38A and 38B, release member 816 and external coupler housing 852 may be manufactured from a range of rigid, non-deformable, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture have a durometer in the range of 35-120 Shore D, but more preferably in the range of 80-110 Shore D.

Hinge member 850 may be manufactured from a range of rigid, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture shall be capable of deformation in bending under the application of an applied load, such as is encountered during a typical "Open and Close" cycle for the needle biopsy device without crazing, fatigue or cracking.

Figure 41:
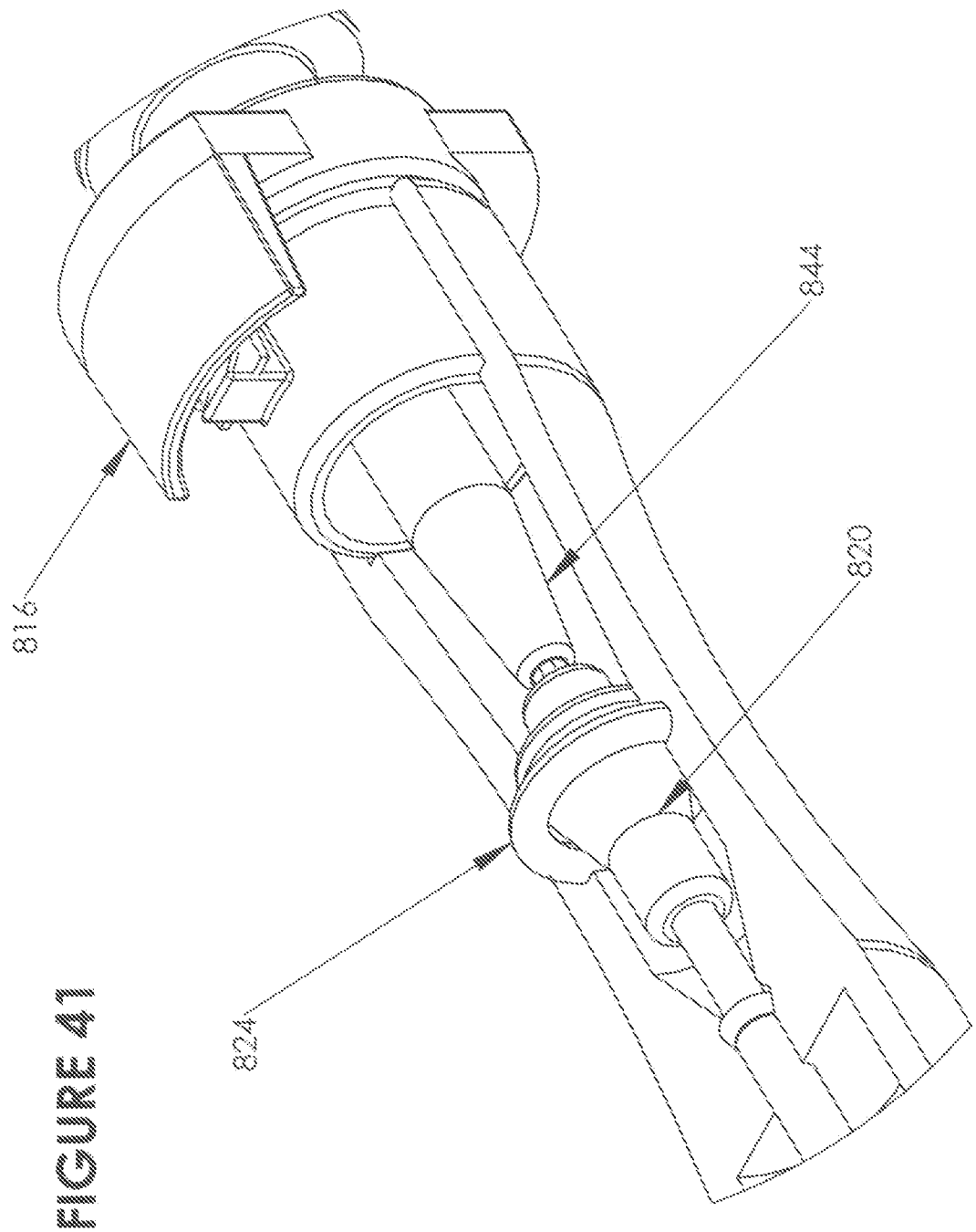
FIG. 41 is a perspective view of an embodiment of a needle biopsy device, according to the present disclosure.
Figure 42:
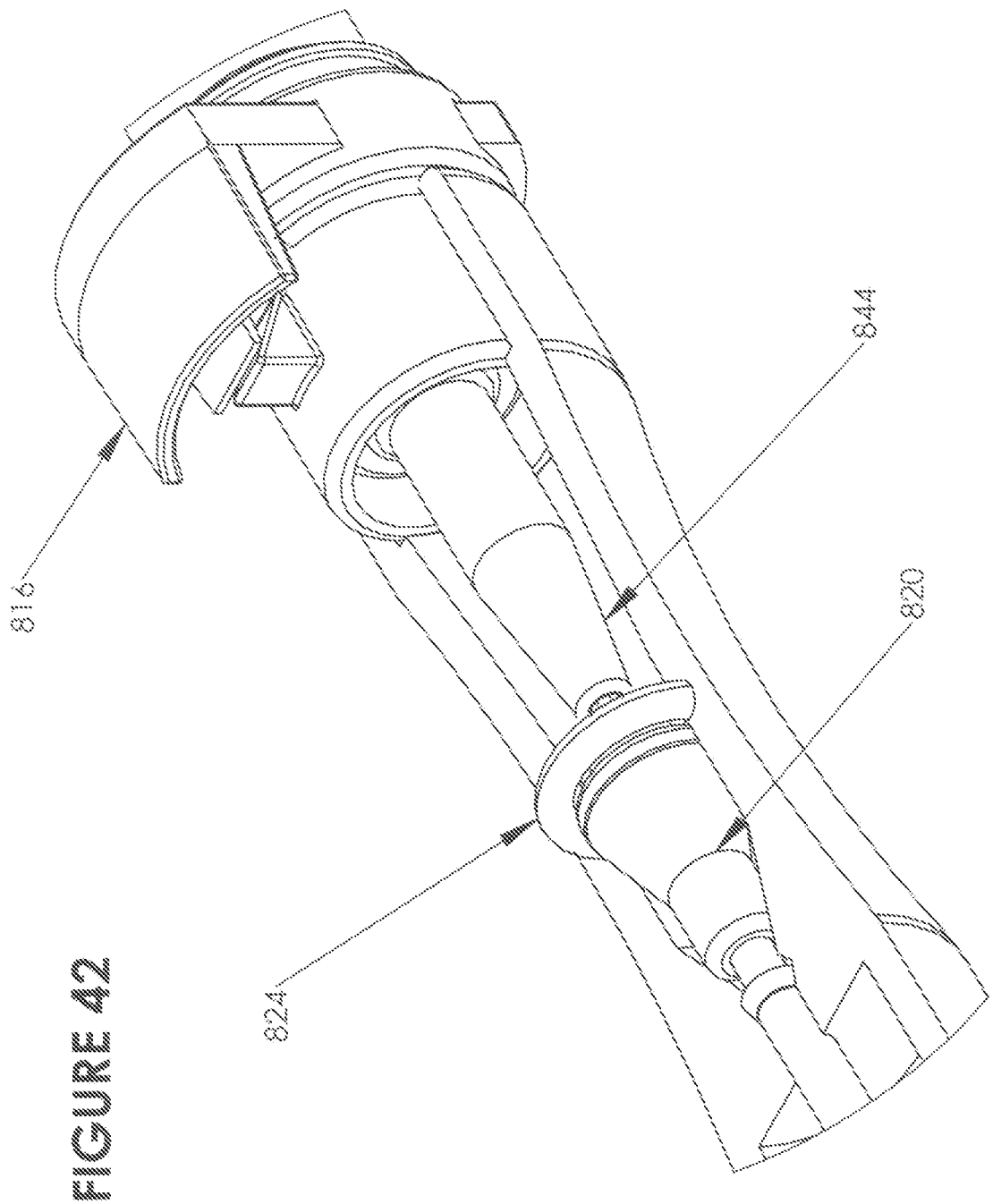
FIG. 42 is a perspective view of an embodiment of a needle biopsy device, according to the present disclosure.

Referring to FIGS. 40 through 42, perspective views of embodiments of needle protection member 820 in use with a needle biopsy device are presented. In an embodiment, the needle housing member is pre-mounted with needle protection hub 820 and needle protection shaft 822. Thereafter, the needle housing member is inserted into the proximal end of the proximal handle member with release member 816. The needle housing member is continually advanced until the taper portion of needle protection hub 820 is seated against ring engagable member 824. The application of additional force pushes needle protection hub 820 forward and ring engagable member 824 deforms until comes to rest. At this juncture, needle protection hub 820 is locked in position and does not move. In addition, the land ring of the needle housing member actuates the release member 816 until release member 816 crosses a "land ring" detail on the external surface of a coupler. At equilibrium, release member 816 is in its fully extended state and the coupler is locked in position.

An intended functionality of release member 816 is to prevent the needle housing member from being removed from the proximal handle member without applying force to release member 816. For example, once a sample has been aspirated from an intended site, release member 816 is actuated and the needle retracted. The needle is continually retracted until the most proximal engageable member 848 engages with needle protection hub 820. Retracting the needle still further with the application of additional force can cause the proximal radius of the taper to contact the ring engagable member 824. Ring engagable member 840 elastically distends and needle protection hub 820 traverses ring engagable member 840. As a result, the needle housing member can now be fully retracted from the device with the distal sharp of the needle protected from inadvertent sticking. Additionally, follow-up samples may be acquired using the same or a virgin needle housing member. Once the needle housing member has been loaded and locked into the coupler, the needle sub-assembly may be rotated. It is envisioned that the ability to core tissue during acquisition, by rotating and advancing and retracting the needle in short strokes, may be provided for.

Referring to FIG. 43, a perspective view of an embodiment of a coupler 854 is presented. In an embodiment, coupler 854 may utilize an O-Ring to provide for smooth locking of the needle housing member to the release member mechanism. In another embodiment, the O-Ring may be removed and the needle housing member may be utilized without such a component.

Referring now to FIG. 44, a perspective view of an embodiment of the needle biopsy device is presented. Proximal inner handle member 804 and distal inner handle member 808 provide for use of locking adjustment mechanisms, such threaded thumb screws to provide a frictional lock to the proximal and distal inner handle member components to lock both needle penetration depth and sheath lumen penetration depths respectively.

Referring now to FIG. 45, a perspective view of an embodiment of a ring engagable member 856 incorporated as part of the proximal inner handle member 804 is presented. In an embodiment, ring engagable member 856 is located in a recessed circular slot in the proximal inner handle member 804. During advancement and retraction of proximal handle member 802 in distal and proximal directions, the proximal inner handle member 804 slides distal and proximal to the inner member across ring expandable member 856. In this instance, ring expandable member 856 provides frictional force resistance between the proximal inner handle member 804 and proximal handle member 802. It is envisioned that when the clinician removes his/her hand from proximal handle member 802, ring expandable member 856 creates sufficient frictional force with the proximal inner handle member 804 that proximal handle member 802 remains at its location and is fixed to proximal inner handle member 804. In this way, the clinician may stop advancement or retraction of the proximal handle member 802 and the handle remains at that location.

Ring expandable member 856 may be manufactured from a range of low durometer, deformable, thermoplastic or thermoset materials such as, but not limited to polyurethane and derivatives thereof, polyether amide block copolymers, polyamide, styrene butadiene rubber and/or alternate derivatives of styrene based polymers, neoprene, and polyethylene and derivatives thereof. In an embodiment, the materials of manufacture have a durometer in the range of 70-120 Shore A, but more preferably in the range of 70-90 Shore A. Such O-Ring components are readily available from a range of companies such as McMaster-Carr by means of an example.

It will be understood that various modifications may be made to the embodiments disclosed herein. Therefore, the above description should not be construed as limiting, but merely as exemplifications of the various embodiments of the invention. Those skilled in the art will envision other modifications within the scope and spirit of the claims appended hereto.

What is claimed is:

1. A needle biopsy device comprising:
   a release member disposed at a proximal end of a handle and comprising an engageable portion that releasably engages a needle housing member disposed within the handle;
   a needle protection hub disposed within the handle and coupled to the needle housing member;
   a needle comprising a protrusion proximate to a distal end of the needle; and a needle protection shaft disposed within the handle and coupled to the needle protection hub, wherein the needle protection shaft comprises a lumen with an inner diameter larger than an outer diameter of the protrusion of the needle,
   wherein the protrusion of the needle is slideably disposed within the needle protection shaft as the needle is withdrawn in a proximal direction,
   wherein the protrusion of the needle is configured to traverse a protruded portion disposed within the handle in response to depressing the release member of the handle and withdrawing the needle in the proximal direction such that the protrusion of the needle locks onto a protruded portion of the needle protection hub and the release member disengages from the needle housing member, thereby withdrawing the needle from the lumen of the handle after the release member disengages from the needle housing member.

2. The needle biopsy device of claim 1, further comprising: a sheath disposed at a distal end of the handle, coaxial with an axial lumen of the handle, and extending distally from the distal end of the handle.

3. The needle biopsy device of claim 1, wherein the protrusion comprises a distal taper and a proximal taper.

4. The needle biopsy device of claim 1, further comprising: a stylet disposed within the needle.

5. The needle biopsy device of claim 1, wherein the release member comprises a deflecting hinge.

6. The needle biopsy device of claim 5, wherein depression of the release member causes the needle housing member to release from the release member of the handle.

7. The needle biopsy device of claim 1, further comprising: the needle housing member coupled to a proximal end of the needle.

8. The needle biopsy device of claim 7, wherein the needle housing member further comprises: one or more indentations configured to limit rotation of the needle housing member with respect to the handle when the needle housing member engages the release member of the handle.

9. The needle biopsy device of claim 7, wherein the release member further comprises: a cylindrical section that partially overlaps an axial lumen of the handle such that the cylindrical section is configured to releasably engage the needle housing member.

10. The needle biopsy device of claim 7, wherein the needle housing member is removed from the handle in the proximal direction when the release member disengages from the needle housing member.

11. The needle biopsy device of claim 7, wherein the protruded portion disposed within the handle further comprises an O-ring disposed distal to the release member.

12. The needle biopsy device of claim 11, wherein the O-ring is disposed within an axial lumen of the handle.

13. The needle biopsy device of claim 11, wherein the needle protection hub is coupled to a proximal end of the needle protection shaft, wherein the needle protection hub comprises a taper portion configured to seat against the O-ring.

14. The needle biopsy device of claim 13, wherein the needle housing member is removed from the handle in the proximal direction when the protrusion of the needle engages the needle protection hub.

15. The needle biopsy device of claim 13, wherein the needle protection hub disengages from the O-ring when the protrusion of the needle engages the needle protection hub.

16. The needle biopsy device of claim 13, wherein the needle protection shaft extends beyond the distal end of the needle when the protrusion of the needle engages the needle protection hub.

17. The needle biopsy device of claim 13, wherein the O-ring is configured to engage a proximal end of the needle protection hub when the needle housing member is inserted into the handle.

18. The needle biopsy device of claim 17, wherein the O-ring is configured to circumscribe the proximal end of the needle protection hub when the needle housing member engages the release member of the handle in a locked configuration.

19. The needle biopsy device of claim 13, wherein a distal end of the needle housing member contacts a proximal end of the needle protection hub when the needle housing member engages the release member of the handle.

20. The needle biopsy device of claim 19, wherein the needle protection hub seats against the O-ring when the needle housing member engages the release member of the handle.

* * * * *